(12) United States Patent
Hall et al.

(10) Patent No.: US 10,428,075 B2
(45) Date of Patent: *Oct. 1, 2019

(54) COELENTERAZINE ANALOGUES

(71) Applicant: PROMEGA CORPORATION, Madison, WI (US)

(72) Inventors: Mary Hall, Waunakee, WI (US); Thomas Kirkland, Atascadero, CA (US); Thomas Machleidt, Madison, WI (US); Anton Shakhmin, Grover Beach, CA (US); Joel R. Walker, San Luis Obispo, CA (US)

(73) Assignee: PROMEGA CORPORATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/982,514

(22) Filed: May 17, 2018

(65) Prior Publication Data

US 2018/0334463 A1 Nov. 22, 2018

Related U.S. Application Data

(63) Continuation of application No. 15/661,582, filed on Jul. 27, 2017, now Pat. No. 10,000,500.

(60) Provisional application No. 62/367,689, filed on Jul. 28, 2016.

(51) Int. Cl.
    C07D 487/04 (2006.01)
    A61K 49/00 (2006.01)
    C07D 519/00 (2006.01)
    C09K 11/06 (2006.01)
    C12Q 1/66 (2006.01)

(52) U.S. Cl.
    CPC ........ *C07D 487/04* (2013.01); *A61K 49/0021* (2013.01); *C07D 519/00* (2013.01); *C09K 11/06* (2013.01); *C12Q 1/66* (2013.01); *C12Y 113/12005* (2013.01); *C12Y 113/12013* (2013.01); *C09K 2211/1011* (2013.01); *C09K 2211/1018* (2013.01)

(58) Field of Classification Search
    None
    See application file for complete search history.

(56) References Cited

U.S. PATENT DOCUMENTS

| | | |
|---|---|---|
| 8,026,363 B2 | 9/2011 | Satoshi |
| 8,471,015 B2 | 6/2013 | Inouye |
| 8,765,921 B2 | 7/2014 | Inouye et al. |
| 8,772,484 B2 | 7/2014 | Inouye et al. |
| 8,871,931 B2 | 10/2014 | Inouye |
| 8,883,432 B2 | 11/2014 | Inouye et al. |
| 8,975,403 B2 | 3/2015 | Inouye et al. |
| 9,075,058 B2 | 7/2015 | Inouye et al. |
| 9,151,739 B2 | 10/2015 | Inouye et al. |
| 2009/0075309 A1 | 3/2009 | Gambhir et al. |
| 2011/0244481 A1 | 10/2011 | Inouye et al. |
| 2011/0288280 A1 | 11/2011 | Hosoya et al. |
| 2012/0035070 A1 | 2/2012 | Inouye et al. |
| 2012/0107849 A1 | 5/2012 | Klaubert et al. |
| 2012/0117667 A1 | 5/2012 | Klaubert et al. |
| 2014/0302539 A1 | 10/2014 | Inouye et al. |
| 2014/0316137 A1 | 10/2014 | Inouye et al. |
| 2015/0119575 A1 | 4/2015 | Inouye et al. |
| 2015/0266833 A1 | 9/2015 | Inouye et al. |
| 2015/0344936 A1 | 12/2015 | Inouye et al. |

FOREIGN PATENT DOCUMENTS

| | | |
|---|---|---|
| WO | WO 2007096764 | 8/2007 |
| WO | WO 2010121003 | 10/2010 |
| WO | WO 2011007314 | 1/2011 |
| WO | WO 2012040105 | 3/2012 |
| WO | WO 2012061530 | 5/2012 |
| WO | WO 2014145512 | 9/2014 |

OTHER PUBLICATIONS

Anton Shakhmin et al: "Three Efficient Methods for Preparation of Coelenterazine Analogues", Chemistry—A European Journal, 2016, vol. 22, No. 30, pp. 10369-10375.

International Search Report and Written Opinion for Application No. PCT/US2017/044150 dated Dec. 11, 2017 (18 pages).

Phakhodee et al., "Suzuki-Miyaura coupling for general synthesis of dehydrocoelenterazine applicable for 6-position analogs directing toward bioluminescence studies," Tetrahedron, 2011; 67(6):1150-1157.

Ikeda et al., "Design of luciferase-displaying protein nanoparticles for use as highly sensitive immunoassay detection probes," Analyst, 2016; 141:6557-6563.

Devillers et al., "Imidazolopyrazinones as potential antioxidants," Bioorganic & Medicinal Chemistry Letters, 2001; 11(17):2305-2309.

Hosoya et al., "Concise Synthesis of v-Coelenterazines," Org. Lett, 2015; 17(15):3888-3891.

Kojima et al., "Improved Syntheses of Watasenia Preluciferin (Coelenterazine) and Watasenia Luciferin (Coelenterazine Disulfate), and Site Specific Syntheses of the Coelenterazine Monosulfates,"ITE Letters on Batteries, New Technologies & Medicine, 2001; 2(3):393-397.

Nishihara et al., "Bioluminescent coelenterazine derivatives with imidazopyrazinone C-6 extended substitution," Chem Commun 2015;51(2):391-4.

Shrestha et al., "Strategies for Large-Scale Synthesis of Coelenterazine for in Vivo Applications," Synthesis 2014; 46(05): 646-652.

*Primary Examiner* — Heidi Reese

(74) *Attorney, Agent, or Firm* — Casimir Jones, S.C.; Anne M. Reynolds

(57) ABSTRACT

Described are coelenterazine analogues, methods for making the analogues, kits comprising the analogues, and methods of using the compounds for the detection of luminescence in luciferase-based assays.

14 Claims, 18 Drawing Sheets

COELENTERAZINE ANALOGUES

RELATED APPLICATIONS

This application is a continuation of U.S. application Ser. No. 15/661,582, filed Jul. 27, 2017, which claims the benefit of U.S. provisional application Ser. No. 62/367,689, filed Jul. 28, 2016, which is incorporated herein by reference in its entirety.

TECHNICAL FIELD

The present disclosure relates to coelenterazine analogues, methods for making coelenterazine analogues, and methods of using coelenterazine analogues in luciferase-based assays.

BACKGROUND

Bioluminescent assays are used extensively in the investigation of cellular physiology, especially processes associated with gene expression. In particular, luciferase reporter enzymes are quite valuable tools in this field, and, to date, there has been intense protein engineering to obtain small and environmentally insensitive luciferases that may be useful in bioluminescent assays. There exist a number of efficient luciferase reporters enabling whole-cell biosensor measurements, drug discovery through high-throughput screening, and in vivo imaging, which also permits the study of protein-protein interactions in living cells, apoptosis, and cell viability. Luciferases that use coelenterazine and coelenterazine analogues as substrates are among the most widely used systems due to their brightness and acceptance in whole cell applications.

SUMMARY OF THE INVENTION

Many known coelenterazine analogues have deficiencies, which limit their effectiveness as luciferase substrates and usefulness in luciferase-based assays. These deficiencies include cell toxicity, light sensitivity, thermodynamic instability, low aqueous solubility, and low cell permeability. Accordingly, there exists a need for coelenterazine analogues with improved properties and methods for synthesizing the analogues.

In one aspect, disclosed are compounds of formula (I),

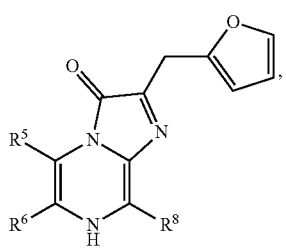

(I)

or a tautomer, or a salt thereof, wherein $R^5$ is hydrogen, halogen, hydroxy, cyano, nitro, amino, alkylamino, dialkylamino, alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl;

$R^6$ is alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; or $R^5$ and $R^6$ together with the atoms to which they are attached, form a 5- or 6-membered partially unsaturated or fully unsaturated ring, the 5- or 6-membered ring optionally containing 1, 2 or 3 heteratoms or heteroatom groups each independently selected from the group consisting of O, N, S, NO, SO and $SO_2$ as ring members, the 5- or 6-membered ring optionally fused to an aryl, heteroaryl, heterocycle, or cycloalkyl, the 5- or 6-membered ring substituted with 0, 1, 2, 3, or 4 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl; and $R^8$ is alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl;

wherein said alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl;

provided that the following compounds are excluded from formula (I):
8-benzyl-2-(furan-2-ylmethyl)-6-phenylimidazo[1,2-a]pyrazin-3 (7H)-one; and
8-benzyl-2-(furan-2-ylmethyl)-6-(4-hydroxyphenyl)imidazo[1,2-a]pyrazin-3 (7H)-one.

In another aspect, disclosed are compounds of formula (II),

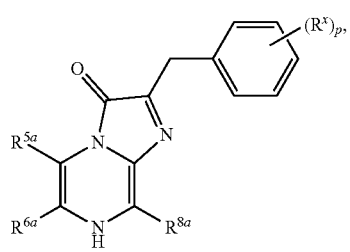

(II)

or a tautomer, or a salt thereof, wherein $R^x$ is halogen, hydroxy, cyano, nitro, amino, alkylamino, dialkylamino, alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl;

p is 0, 1, 2, 3, 4, or 5;

$R^{5a}$ is hydrogen, halogen, hydroxy, cyano, nitro, amino, alkylamino, dialkylamino, alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl;

$R^{6a}$ is alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; or $R^{5a}$ and $R^{6a}$ together with the atoms to which they are attached, form a 5- or 6-membered partially unsaturated or fully unsaturated ring, the 5- or 6-membered ring optionally containing 1, 2 or 3 heteratoms or heteroatom groups each independently selected from the group consisting of O, N, S, NO, SO and $SO_2$ as ring members, the 5- or 6-membered ring optionally fused to an aryl, heteroaryl, heterocycle, or cycloalkyl, the 5- or 6-membered ring substituted with 0, 1, 2, 3, or 4 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl; and $R^{8a}$ is alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl;

wherein said alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl;

provided that $R^x$ is not 4-hydroxy when p is 1, $R^{5a}$ is not hydrogen, or $R^{8a}$ is not benzyl, or any combination thereof.

Also disclosed are methods of making the compounds, kits comprising the compounds, and methods of using the compounds as luciferase substrates in luciferase-based assays.

DETAILED DESCRIPTION

Figure 1A:
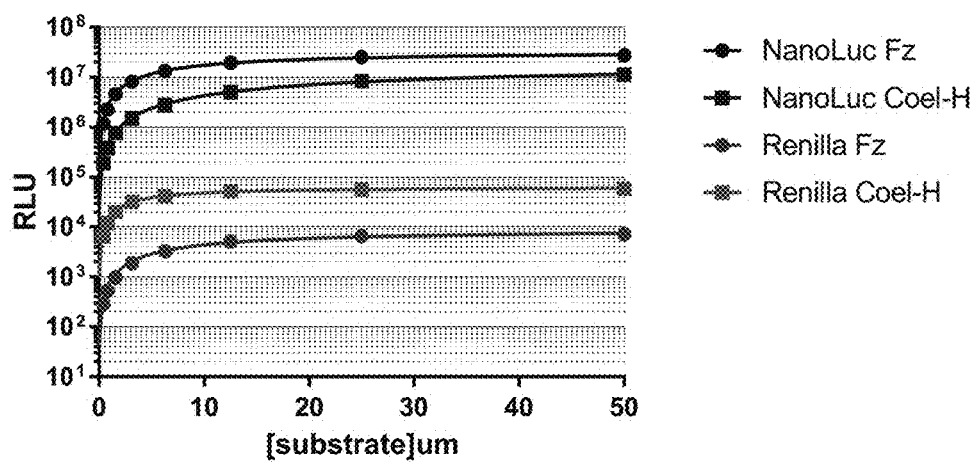
FIGS. 1A-1D show luminescence screening with Nanoluc® Luciferase and *Renilla* Luciferase.
Figure 1B:
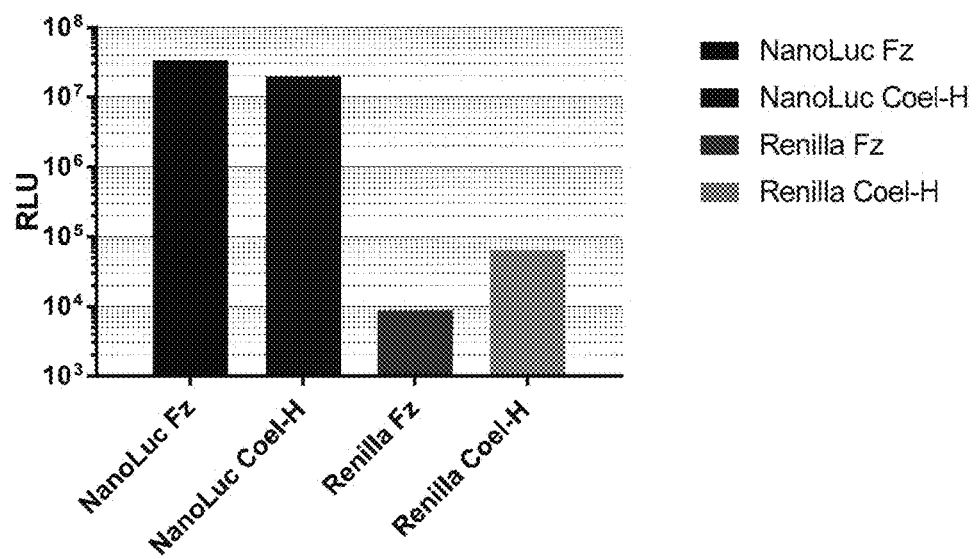
Figure 1C:
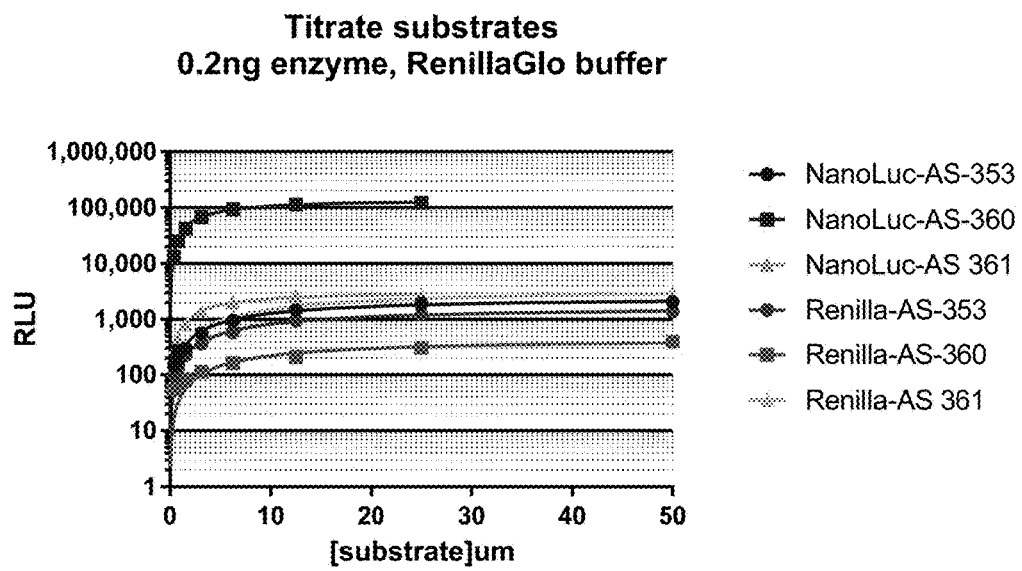
Figure 1D:
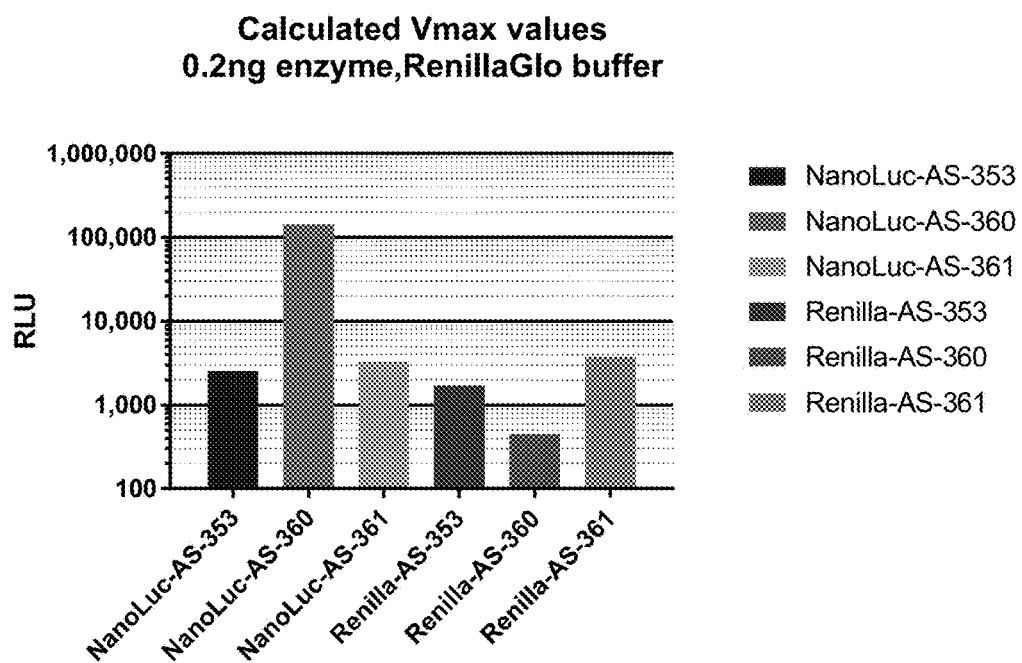

Disclosed herein are coelenterazine analogues. The coelenterazine analogues can be compounds of formula (I) or formula (II) and can be useful substrates for proteins that utilize coelenterazine ("coelenterazine-utilizing enzymes") to produce luminescence, including, but not limited to, luciferases and photoproteins found in various marine organisms such as cnidarians (e.g., *Renilla* luciferase), jellyfish (e.g., aequorin from the *Aequorea* jellyfish) and decapods luciferases (e.g., luciferase complex of *Oplophorus gracilirostris*).

The compounds of formula (I) and formula (II) may produce red-shifted bioluminescent light. Known substrates for the coelenterazine utilizing enzymes, such as the NANOLUC® bioluminescent enzyme, generate bioluminescent light with a peak of about 460 nM. However, the compounds disclosed herein (e.g., compounds of formula (I) and (II)) can provide wavelength shifts of the bioluminescent light from 460-596 nM. Unlike blue light, red light is not attenuated in tissue, therefore bioluminescent systems that generate red light are preferred for in vivo imaging applications. Thus, the compounds of formula (I) and (II) may be useful for in vivo luminescent imaging applications as well as in other applications that utilize bioluminescence.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; *Smith and March March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a hydrocarbon chain containing from 2 to 10 carbon atoms with at least one carbon-carbon double bond. In some embodiments, the alkenyl group may be substituted with an aryl group, such as a phenyl.

The term "alkynyl" as used herein, means a hydrocarbon chain containing from 2 to 10 carbon atoms with at least one carbon-carbon triple bond. In some embodiments, the alkynyl group may be substituted with an aryl group, such as a phenyl.

The term "alkoxyalkyl" as used herein, refers to an alkoxy group, as defined herein, appended to the parent molecular moiety through an alkyl group, as defined herein.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and —$CH_2CH_2CH_2CH_2CH_2$—.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings.

The term "cycloalkyl" as used herein, refers to a carbocyclic ring system containing three to ten carbon atoms, zero heteroatoms and zero double bonds. Representative examples of cycloalkyl include, but are not limited to, monocyclic cycloalkyl such as cyclopropyl, cyclobutyl, cyclopentyl, cyclohexyl, cycloheptyl, cyclooctyl, cyclononyl and cyclodecyl. The cycloalkyl groups described herein can be appended to the parent molecular moiety through any substitutable carbon atom. "Cycloalkyl" also includes carbocyclic ring systems in which a cycloalkyl group is appended to the parent molecular moiety and is fused to an aryl group as defined herein.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "alkoxyfluoroalkyl" as used herein, refers to an alkoxy group, as defined herein, appended to the parent molecular moiety through a fluoroalkyl group, as defined herein.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "haloalkoxy" as used herein, means at least one haloalkyl group, as defined herein, is appended to the parent molecular moiety through an oxygen atom.

The term "heteroalkyl" as used herein, means an alkyl group, as defined herein, in which one or more of the carbon atoms has been replaced by a heteroatom selected from S, Si, O, P and N. The heteroatom may be oxidized. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered aromatic monocyclic rings have three double bonds. The bicyclic heteroaryl groups are exemplified by a monocyclic heteroaryl ring fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4(1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings.

The term "hydroxyl" as used herein, means an —OH group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituted" refers to a group that may be further substituted with one or more non-hydrogen substituent groups. Exemplary substituent groups are halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds
Disclosed are compounds of formula (I):

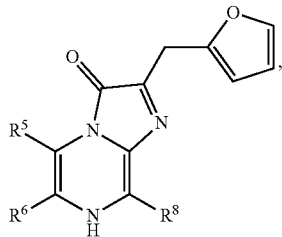

(I)

or tautomers, or salts thereof (e.g., pharmaceutically acceptable salts), wherein $R^5$ is hydrogen, halogen, hydroxy, cyano, nitro, amino, alkylamino, dialkylamino, alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; $R^6$ is alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; or $R^5$ and $R^6$ together with the atoms to which they are attached, form a 5- or 6-membered partially unsaturated or fully unsaturated ring, the 5- or 6-membered ring optionally containing 1, 2 or 3 heteroatoms or heteroatom groups each independently selected from the group consisting of O, N, S, NO, SO and $SO_2$ as ring members, the 5- or 6-membered ring optionally fused to an aryl, heteroaryl, heterocycle, or cycloalkyl, the 5- or 6-membered ring substituted with 0, 1, 2, 3, or 4 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl; and $R^8$ is alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; wherein said alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl; provided that the following compounds are excluded from formula (I): 8-benzyl-2-(furan-2-ylmethyl)-6-phenylimidazo[1,2-a]pyrazin-3(7H)-one; and 8-benzyl-2-(furan-2-ylmethyl)-6-(4-hydroxyphenyl)imidazo[1,2-a]pyrazin-3 (7H)-one.

In certain embodiments according to formula (I), $R^5$ is hydrogen, $C_1$-$C_6$alkyl, $C_{2-6}$ alkenyl, $C_{2-6}$alkynyl (e.g., $C_2$alkynyl), phenyl, cyano, amino, $C_1$-$C_6$alkylamino, $C_1$-$C_6$dialkylamino (e.g., dimethylamino), or $C_1$-$C_6$alkoxy (e.g., methoxy), wherein the phenyl is optionally substituted with 1-3 substituents independently selected from the group consisting of halogen, nitro, cyano, $C_1$-$C_6$alkyl, $C_1$-$C_6$haloalkyl, amino, $C_1$-$C_6$alkylamino, $C_1$-$C_6$dialkylamino, hydroxy, and $C_1$-$C_6$alkoxy; $R^6$ is phenyl, naphthyl, tricyclic aryl, biphenyl (e.g., 1,4-biphenyl), or heteroaryl (e.g., a monocyclic or bicyclic ring system), wherein the phenyl, naphthyl, biphenyl, tricyclic aryl, and heteroaryl are independently optionally substituted with 1-3 substituents independently selected from the group consisting of halogen (e.g., fluoro), nitro, cyano, $C_1$-$C_6$alkyl (e.g., methyl), $C_1$-$C_6$haloalkyl, amino, $C_1$-$C_6$alkylamino, $C_1$-$C_6$dialkylamino, hydroxy, and $C_1$-$C_6$alkoxy (e.g., methoxy); or $R^5$ and $R^6$ together with the atoms to which they are attached, form a 5- or 6-membered partially unsaturated or fully unsaturated carbocyclic ring, the 5- or 6-membered carbocyclic ring being optionally fused to a phenyl, the 5- or 6-membered carbocyclic ring being optionally substituted with 1-3 substituents independently selected from the group consisting of oxo, halogen, nitro, cyano, $C_1$-$C_6$alkyl, $C_1$-$C_6$haloalkyl, amino, $C_1$-$C_6$alkylamino, $C_1$-$C_6$dialkylamino, hydroxy, and $C_1$-$C_6$alkoxy; and $R^8$ is $C_1$-$C_3$alkyl substituted with phenyl, $C_2$alkenyl substituted with phenyl, $C_2$alkynyl substituted with phenyl, phenyl, cycloalkyl, naphthyl, biphenyl, tricyclic aryl, heteroaryl (e.g., a monocyclic or bicyclic ring system), or heterocycle, wherein each phenyl, cycloalkyl, naphthyl, biphenyl, tricyclic aryl, heteroaryl, and heterocycle in $R^8$ is independently optionally substituted with 1-3 substituents independently selected from the group consisting of oxo, halogen (e.g., fluoro, chloro, bromo), nitro, cyano, $C_1$-$C_6$alkyl (e.g., methyl), $C_1$-$C_6$haloalkyl (e.g., $CF_3$), amino, $C_1$-$C_6$alkylamino, $C_1$-$C_6$dialkylamino (e.g., dimethylamino), hydroxy, and $C_1$-$C_6$alkoxy.

In other embodiments, $R^5$ is hydrogen, $C_{2-6}$alkynyl, phenyl, cyano, $C_1$-$C_6$dialkylamino, or $C_1$-$C_6$alkoxy, wherein the phenyl is optionally substituted with 1-3 substituents independently selected from the group consisting of halogen, nitro, cyano, $C_1$-$C_6$alkyl, $C_1$-$C_6$haloalkyl, amino, $C_1$-$C_6$alkylamino, $C_1$-$C_6$dialkylamino, hydroxy, and $C_1$-$C_6$alkoxy; $R^6$ is phenyl, naphthyl, tricyclic aryl, biphenyl, or heteroaryl, wherein the phenyl, naphthyl, biphenyl, tricyclic aryl, and heteroaryl are independently optionally substituted with 1-3 substituents independently selected from the group consisting of halogen, nitro, cyano, $C_1$-$C_6$alkyl, $C_1$-$C_6$haloalkyl, amino, $C_1$-$C_6$alkylamino, $C_1$-$C_6$dialkylamino, hydroxy, and $C_1$-$C_6$alkoxy; or $R^5$ and $R^6$ together with the atoms to which they are attached, form a 6-membered partially unsaturated or fully unsaturated carbocyclic ring, the 6-membered carbocyclic ring being optionally fused to a phenyl, the 6-membered carbocyclic ring being optionally substituted with 1-3 substituents independently selected from the group consisting of oxo, halogen, nitro, cyano, $C_1$-$C_6$alkyl, $C_1$-$C_6$haloalkyl, amino, $C_1$-$C_6$alkylamino, $C_1$-$C_6$dialkylamino, hydroxy, and $C_1$-$C_6$alkoxy; and $R^8$ is $C_1$-$C_3$alkyl substituted with phenyl, $C_2$alkenyl substituted with phenyl, $C_2$alkynyl substituted with phenyl, phenyl, monocyclic cycloalkyl, naphthyl, biphenyl, tricyclic aryl, heteroaryl, or heterocycle, wherein each phenyl, monocyclic cycloalkyl, naphthyl, biphenyl, tricyclic aryl, heteroaryl, and heterocycle in $R^8$ is independently optionally substituted with 1-3 substituents independently selected from the group consisting of oxo, halogen, nitro, cyano, $C_1$-$C_6$alkyl, $C_1$-$C_6$haloalkyl, amino, $C_1$-$C_6$alkylamino, $C_1$-$C_6$dialkylamino, hydroxy, and $C_1$-$C_6$alkoxy.

In still further embodiments, $R^5$ is hydrogen, $C_{2-6}$alkynyl, phenyl, cyano, $C_1$-$C_6$dialkylamino, or $C_1$-$C_6$alkoxy; $R^6$ is phenyl, naphthyl, tricyclic aryl, biphenyl, or heteroaryl, wherein the phenyl, naphthyl, biphenyl, tricyclic aryl, and heteroaryl are independently optionally substituted with 1-3 substituents independently selected from the group consisting of halogen, cyano, $C_1$-$C_6$alkyl, amino, hydroxy, and $C_1$-$C_6$alkoxy; or $R^5$ and $R^6$ together with the atoms to which they are attached, form a 6-membered partially unsaturated or fully unsaturated carbocyclic ring, the 6-membered carbocyclic ring being optionally fused to a phenyl; and $R^8$ is $C_1$-$C_3$alkyl substituted with phenyl, $C_2$alkenyl substituted with phenyl, $C_2$alkynyl substituted with phenyl, phenyl, monocyclic cycloalkyl, naphthyl, biphenyl, tricyclic aryl, heteroaryl, or heterocycle, wherein each phenyl, monocyclic cycloalkyl, naphthyl, biphenyl, tricyclic aryl, heteroaryl, and heterocycle is independently optionally substituted with 1-3 substituents independently selected from the group consisting of oxo, halogen, nitro, cyano, $C_1$-$C_6$alkyl, $C_1$-$C_6$haloalkyl, amino, $C_1$-$C_6$alkylamino, $C_1$-$C_6$dialkylamino, hydroxy, and $C_1$-$C_6$alkoxy.

In certain embodiments, $R^5$ is hydrogen, cyano, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, or phenyl.

In certain embodiments, $R^5$ is hydrogen.

In certain embodiments, $R^6$ is aryl, bicyclic aryl, tricyclic aryl, biphenyl, heteroaryl, bicyclic heteroaryl, or tricyclic heteroaryl; substituted with 0, 1, 2, or 3 substituents, each independently selected from the group consisting of halogen, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^6$ is phenyl, bicyclic aryl, tricyclic aryl, biphenyl, monocyclic heteroaryl, bicyclic heteroaryl, or tricyclic heteroaryl; substituted with 0, 1, 2, or 3 substituents, each independently selected from the group consisting of halogen, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^6$ is

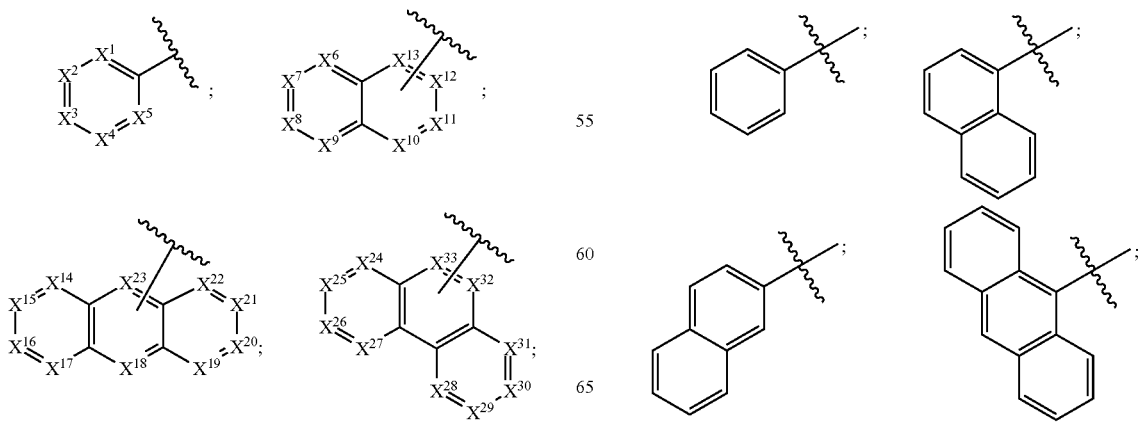

wherein $X^1$-$X^{43}$ are each independently $CR^{11}$ or N, wherein $R^{11}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $X^6$-$X^{13}$ is C where the $R^6$ attaches to the parent molecular formula; provided that one of $X^{14}$-$X^{23}$ is C where the $R^6$ attaches to the parent molecular formula; provided that one of $X^{24}$-$X^{33}$ is C where the $R^6$ attaches to the parent molecular formula; provided that one of $X^{34}$-$X^{38}$ is C to attach to the ring containing $X^{39}$-$X^{43}$; $Y^1$, $Y^5$, $Y^{15}$, and $Y^{22}$ are O, S, or $NR^{12}$, wherein $R^{12}$ is hydrogen, $C_1$-$C_6$-alkyl, or $C_1$-$C_6$-haloalkyl; $Y^{30}$ is N; $Y^2$-$Y^4$, $Y^6$-$Y^{14}$, $Y^{16}$-$Y^{21}$, and $Y^{23}$-$Y^{29}$ are each independently $CR^{13}$ or N, wherein $R^{13}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $Y^9$-$Y^{14}$ is C where the $R^6$ attaches to the parent molecular formula; provided that one of $Y^{16}$-$Y^{21}$ is C where the $R^6$ attaches to the parent molecular formula; and provided that one of $Y^{23}$-$Y^{29}$ is C where the $R^6$ attaches to the parent molecular formula.

In certain embodiments, $R^6$ is selected from the group consisting of:

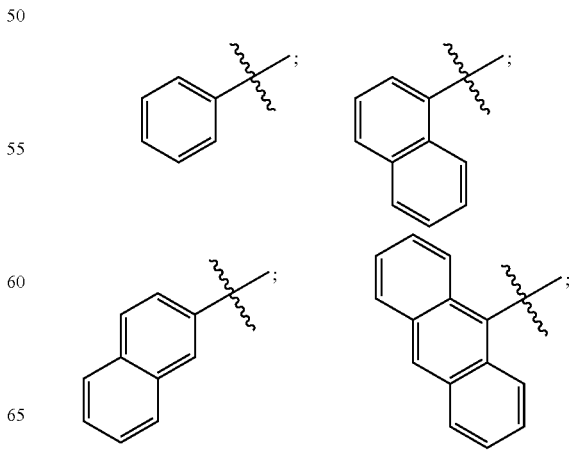

-continued

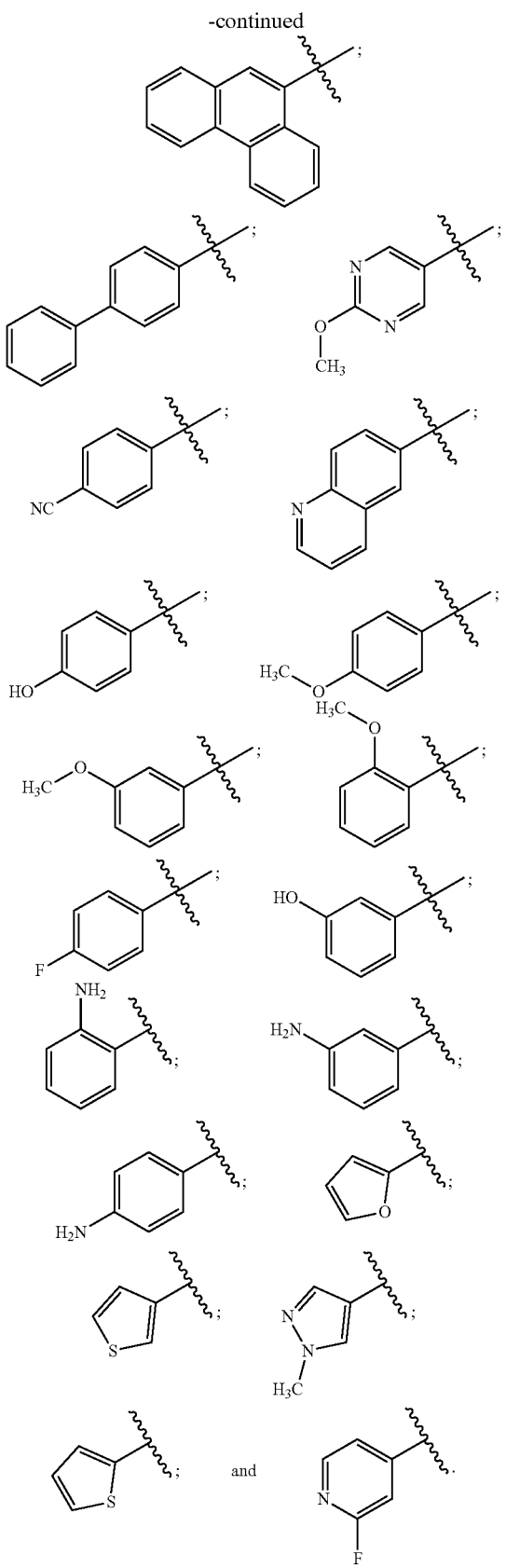

In certain embodiments, $R^5$ and $R^6$ together with the atoms to which they are attached, form a 6-membered partially unsaturated or fully unsaturated ring, the 6-membered ring optionally containing 1, 2 or 3 heteroatoms or heteroatom groups each independently selected from the group consisting of O, N, S, NO, SO and $SO_2$ as ring members, the 6-membered ring optionally fused to an aryl, 5- or 6-membered heteroaryl, 5- or 6-membered heterocycle, or 5-, 6- or 7-membered cycloalkyl, the 6-membered ring and the optionally fused ring each independently substituted with 0, 1, 2, 3, or 4 substituents each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, $R^5$ and $R^6$ together with the atoms to which they are attached, form a ring system selected from the group consisting of:

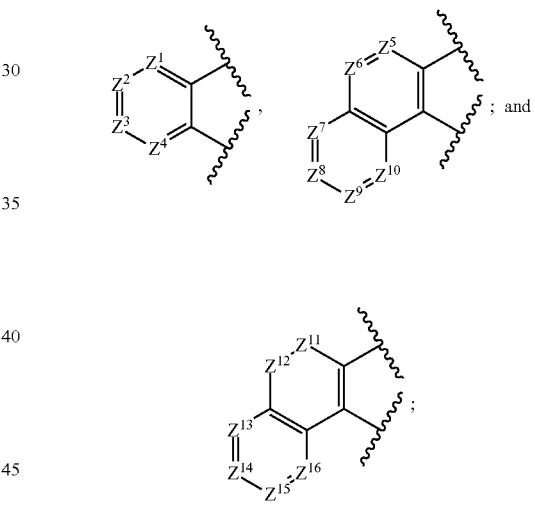

wherein $Z^1$-$Z^{10}$ and $Z^{13}$-$Z^{16}$ are each independently $CR^{14}$ or N, wherein $R^{14}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; and $Z^{11}$ and $Z^{12}$ are each independently $CR^{15}R^{16}$, $NR^{17}$, O, or S; wherein $R^{15}$ and $R^{16}$, at each occurrence, are each independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; and $R^{17}$, at each occurrence, is independently selected from the group consisting of hydrogen, $C_1$-$C_6$-alkyl, and $C_1$-$C_6$-haloalkyl.

In certain embodiments, $R^5$ and $R^6$ together with the atoms to which they are attached, form a ring system selected from the group consisting of:

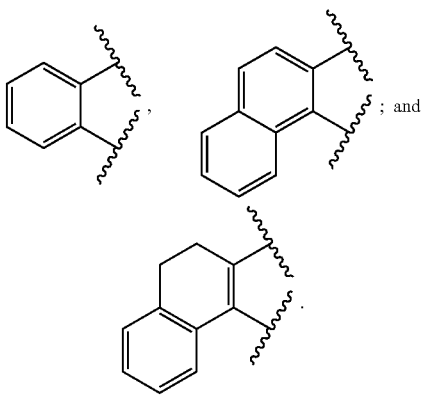

In certain embodiments, $R^8$ is aryl, bicyclic aryl, tricyclic aryl, biphenyl, heteroaryl, bicyclic heteroaryl, tricyclic heteroaryl, heterocycle, or cycloalkyl; substituted with 0, 1, 2, or 3 substituents, each independently selected from the group consisting of halogen, =O, =S, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^8$ is phenyl, bicyclic aryl, tricyclic aryl, biphenyl, monocyclic heteroaryl, bicyclic heteroaryl, tricyclic heteroaryl, heterocycle, or cycloalkyl; substituted with 0, 1, 2, or 3 substituents, each independently selected from the group consisting of halogen, =O, =S, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^8$ is

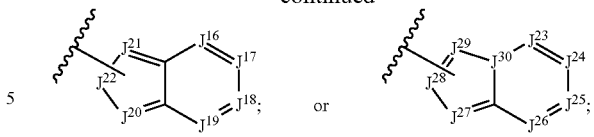

wherein $E^1$-$E^{43}$ are each independently $CR^{21}$ or N, wherein $R^{21}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $E^6$-$E^{13}$ is C where the $R^8$ attaches to the parent molecular formula; provided that one of $E^{14}$-$E^{23}$ is C where the $R^8$ attaches to the parent molecular formula; provided that one of $E^{24}$-$E^{33}$ is C where the $R^8$ attaches to the parent molecular formula; provided that one of $E^{34}$-$E^{38}$ is C to attach to the ring containing $E^{39}$-$E^{43}$; $J^1$, $J^5$, $J^{15}$, and $J^{22}$ are O, S, or $NR^{22}$, wherein $R^{22}$ is hydrogen, $C_1$-$C_6$-alkyl, or $C_1$-$C_6$-haloalkyl; $J^{30}$ is N; $J^2$-$J^4$, $J^6$-$J^{14}$, $J^{16}$-$J^{21}$, and $J^{23}$-$J^{29}$ are each independently $CR^{23}$ or N, wherein $R^{23}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $J^9$-$J^{14}$ is C where the $R^8$ attaches to the parent molecular formula; provided that one of $J^{16}$-$J^{21}$ is C where the $R^8$ attaches to the parent molecular formula; and provided that one of $J^{23}$-$J^{29}$ is C where the $R^8$ attaches to the parent molecular formula.

In certain embodiments, $R^8$ is selected from the group consisting of:

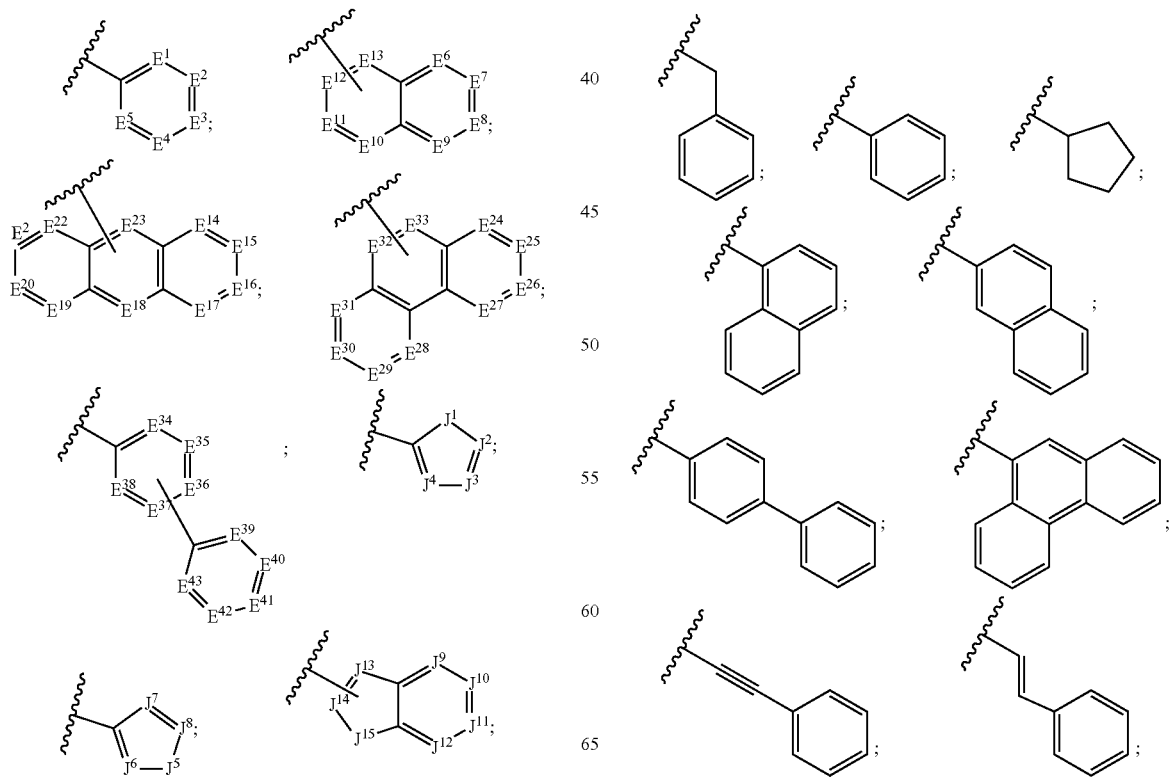

-continued
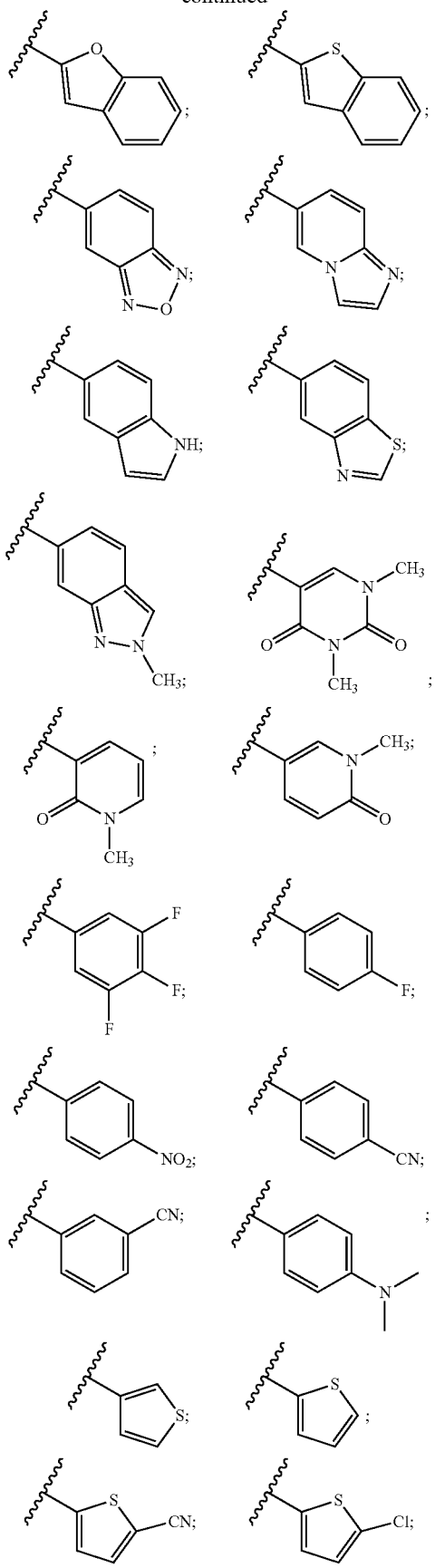
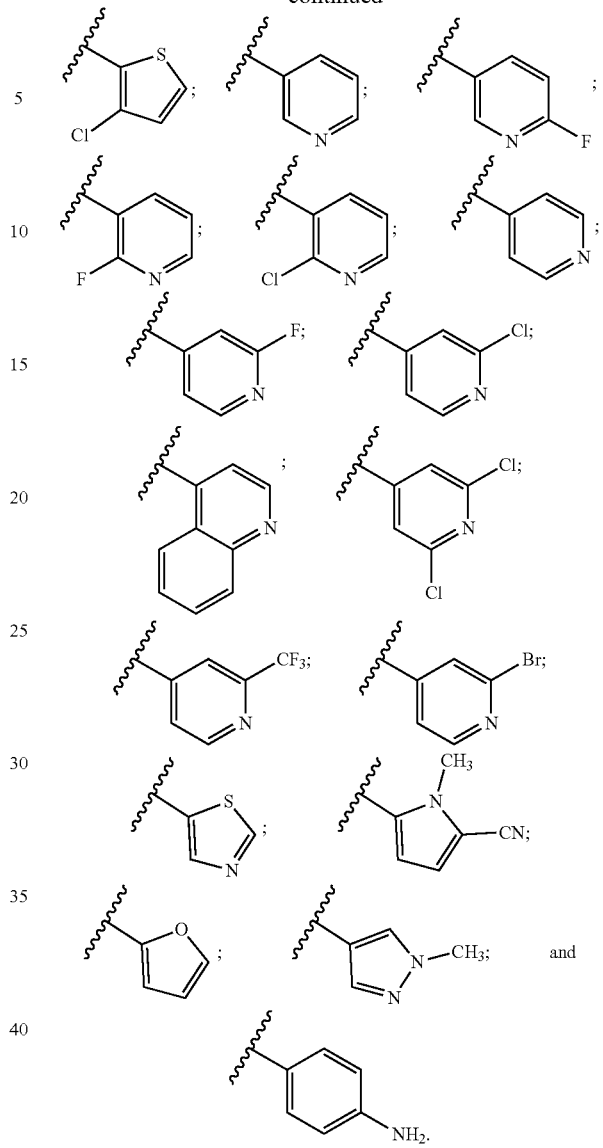
In certain embodiments, the compound of formula (I) is the compound of formula (I-a):
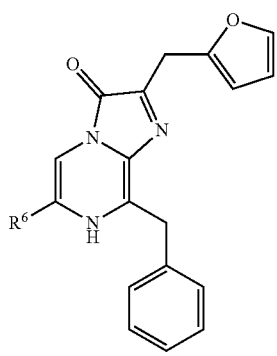
(I-a)
wherein $R^6$ is alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; wherein said alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl; provided that the following compounds are excluded from formula (I-a): 8-benzyl-2-(furan-2-ylmethyl)-6-phenylimidazo[1,2-a]pyrazin-3(7H)-one; and 8-benzyl-2-(furan-2-ylmethyl)-6-(4-hydroxyphenyl)imidazo[1,2-a]pyrazin-3 (7H)-one.

In certain embodiments, $R^6$ is aryl, bicyclic aryl, tricyclic aryl, biphenyl, heteroaryl, bicyclic heteroaryl, or tricyclic heteroaryl; substituted with 0, 1, 2, or 3 substituents, each independently selected from the group consisting of halogen, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^6$ is phenyl, bicyclic aryl, tricyclic aryl, biphenyl, monocyclic heteroaryl, bicyclic heteroaryl, or tricyclic heteroaryl; substituted with 0, 1, 2, or 3 substituents, each independently selected from the group consisting of halogen, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^6$ is

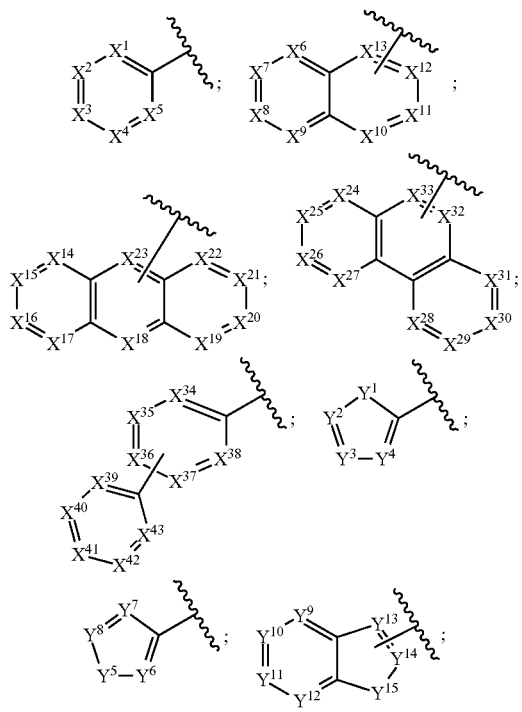

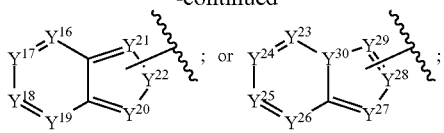

wherein $X^1$-$X^{43}$ are each independently $CR^1$ or N, wherein $R^{11}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $X^6$-$X^{13}$ is C where the $R^6$ attaches to the parent molecular formula; provided that one of $X^{14}$-$X^{23}$ is C where the $R^6$ attaches to the parent molecular formula; provided that one of $X^{24}$-$X^{33}$ is C where the $R^6$ attaches to the parent molecular formula; provided that one of $X^{34}$-$X^{38}$ is C to attach to the ring containing $X^{39}$-$X^{43}$; $Y^1$, $Y^5$, $Y^{15}$, and $Y^{22}$ are O, S, or $NR^{12}$, wherein $R^{12}$ is hydrogen, $C_1$-$C_6$-alkyl, or $C_1$-$C_6$-haloalkyl; $Y^{30}$ is N; $Y^2$-$Y^4$, $Y^6$-$Y^{14}$, $Y^{16}$-$Y^{21}$, and $Y^{23}$-$Y^{29}$ are each independently $CR^{13}$ or N, wherein $R^{13}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $Y^9$-$Y^{14}$ is C where the $R^6$ attaches to the parent molecular formula; provided that one of $Y^{16}$-$Y^{21}$ is C where the $R^6$ attaches to the parent molecular formula; and provided that one of $Y^{23}$-$Y^{29}$ is C where the $R^6$ attaches to the parent molecular formula.

In certain embodiments, $R^6$ is selected from the group consisting of:

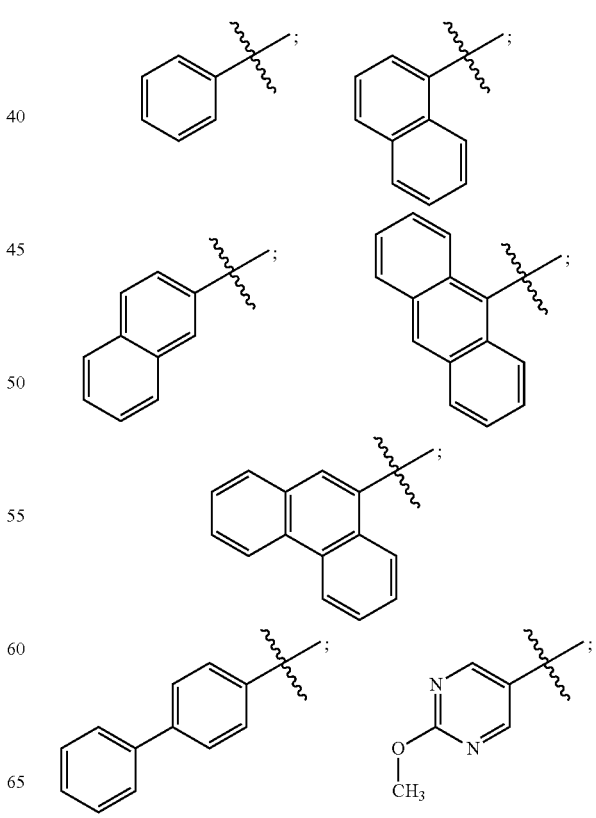

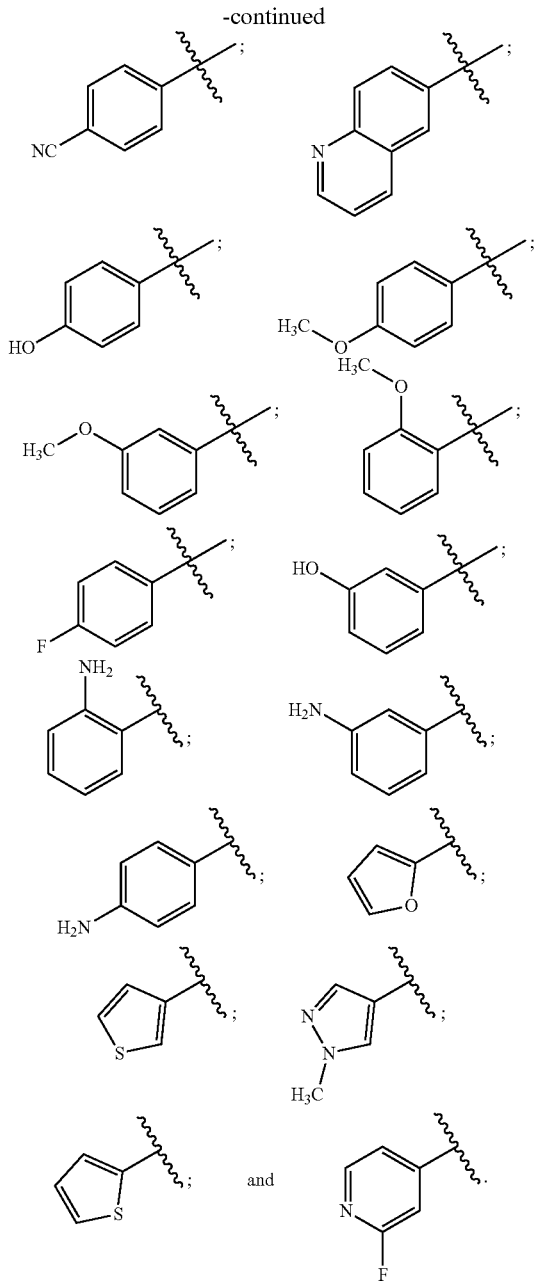

Representative compounds of formula (I-a) include, but are not limited to: 8-benzyl-2-(furan-2-ylmethyl)-6-(naphthalen-1-yl)imidazo[1,2-a]pyrazin-3 (7H)-one; 8-benzyl-2-(furan-2-ylmethyl)-6-(naphthalen-2-yl)imidazo[1,2-a]pyrazin-3 (7H)-one; 6-(anthracen-9-yl)-8-benzyl-2-(furan-2-ylmethyl)imidazo[1,2-a]pyrazin-3 (7H)-one; 8-benzyl-2-(furan-2-ylmethyl)-6-(phenanthren-9-yl)imidazo[1,2-a]pyrazin-3 (7H)-one; 6-([1,1'-biphenyl]-4-yl)-8-benzyl-2-(furan-2-ylmethyl)imidazo[1,2-a]pyrazin-3 (7H)-one; 8-benzyl-2-(furan-2-ylmethyl)-6-(2-methoxypyrimidin-5-yl)imidazo[1,2-a]pyrazin-3 (7H)-one; 4-(8-benzyl-2-(furan-2-ylmethyl)-3-oxo-3,7-dihydroimidazo[1,2-a]pyrazin-6-yl)benzonitrile; 8-benzyl-2-(furan-2-ylmethyl)-6-(quinolin-6-yl)imidazo[1,2-a]pyrazin-3 (7H)-one; 8-benzyl-2-(furan-2-ylmethyl)-6-(4-methoxyphenyl)imidazo[1,2-a]pyrazin-3 (7H)-one; 8-benzyl-2-(furan-2-ylmethyl)-6-(3-methoxyphenyl)imidazo[1,2-a]pyrazin-3 (7H)-one; 8-benzyl-2-(furan-2-ylmethyl)-6-(2-methoxyphenyl)imidazo[1,2-a]pyrazin-3 (7H)-one; 8-benzyl-6-(4-fluorophenyl)-2-(furan-2-ylmethyl)imidazo[1,2-a]pyrazin-3 (7H)-one; 8-benzyl-2-(furan-2-ylmethyl)-6-(3-hydroxyphenyl)imidazo[1,2-a]pyrazin-3 (7H)-one; 6-(2-aminophenyl)-8-benzyl-2-(furan-2-ylmethyl)imidazo[1,2-a]pyrazin-3 (7H)-one; 6-(3-aminophenyl)-8-benzyl-2-(furan-2-ylmethyl)imidazo[1,2-a]pyrazin-3 (7H)-one; 6-(4-aminophenyl)-8-benzyl-2-(furan-2-ylmethyl)imidazo[1,2-a]pyrazin-3 (7H)-one; and pharmaceutically acceptable salts thereof.

In certain embodiments, the compound of formula (I) is the compound of formula (I-b):

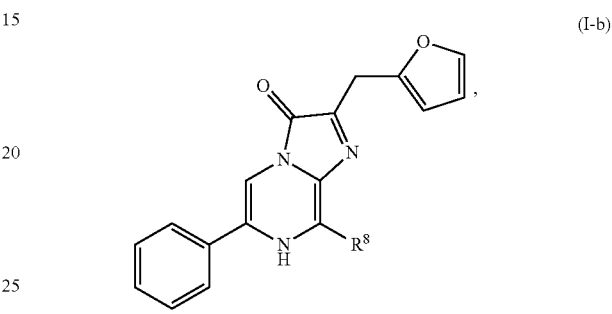

(I-b)

wherein $R^8$ is alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl;

wherein said alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl; provided that the following compound is excluded from formula (I-b): 8-benzyl-2-(furan-2-ylmethyl)-6-phenylimidazo[1,2-a]pyrazin-3 (7H)-one.

In certain embodiments, $R^8$ is $C_1$-$C_3$alkyl substituted with phenyl, $C_2$alkenyl substituted with phenyl, $C_2$alkynyl substituted with phenyl, phenyl, cycloalkyl, naphthyl, biphenyl, tricyclic aryl, heteroaryl (e.g., a monocyclic or bicyclic ring system), or heterocycle, wherein each phenyl, cycloalkyl, naphthyl, biphenyl, tricyclic aryl, heteroaryl, and heterocycle in $R^8$ is independently optionally substituted with 1-3 substituents independently selected from the group consisting of oxo, halogen (e.g., fluoro, chloro, bromo), nitro, cyano, $C_1$-$C_6$alkyl (e.g., methyl), $C_1$-$C_6$haloalkyl (e.g., $CF_3$), amino, $C_1$-$C_6$alkylamino, $C_1$-$C_6$dialkylamino (e.g., dimethylamino), hydroxy, and $C_1$-$C_6$alkoxy.

In certain embodiments, $R^8$ is aryl, bicyclic aryl, tricyclic aryl, biphenyl, heteroaryl, bicyclic heteroaryl, tricyclic heteroaryl, heterocycle, or cycloalkyl; substituted with 0, 1, 2, or 3 substituents, each independently selected from the group consisting of halogen, =O, =S, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^8$ is phenyl, bicyclic aryl, tricyclic aryl, biphenyl, monocyclic heteroaryl, bicyclic heteroaryl, tricyclic heteroaryl, heterocycle, or cycloalkyl; substituted with 0, 1, 2, or 3 substituents, each independently selected from the group consisting of halogen, =O, =S, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^8$ is

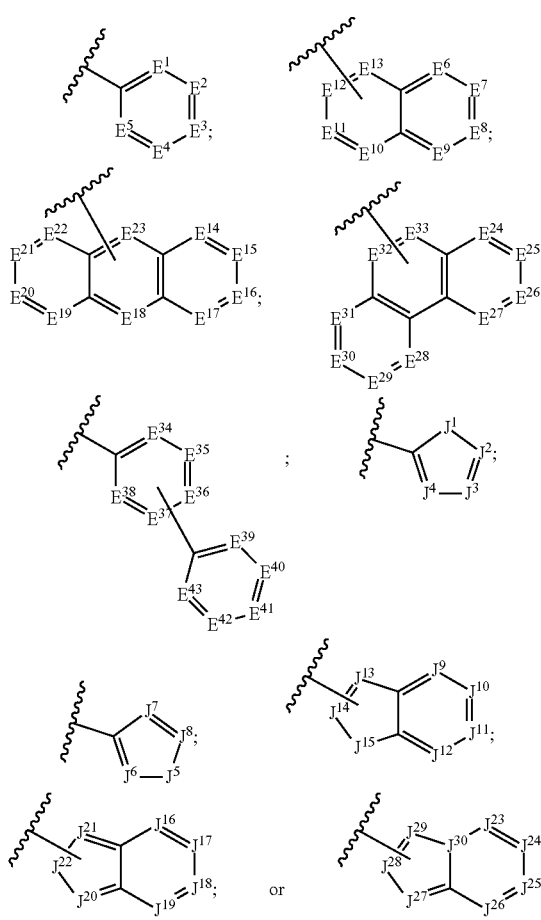

wherein $E^1$-$E^{43}$ are each independently $CR^{21}$ or N, wherein $R^{21}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $E^6$-$E^{13}$ is C where the $R^8$ attaches to the parent molecular formula; provided that one of $E^{14}$-$E^{23}$ is C where the $R^8$ attaches to the parent molecular formula; provided that one of $E^{24}$-$E^{33}$ is C where the $R^8$ attaches to the parent molecular formula; provided that one of $E^{34}$-$E^{38}$ is C to attach to the ring containing $E^{39}$-$E^{43}$; $J^1$, $J^5$, $J^{15}$, and $J^{22}$ are O, S, or $NR^{22}$, wherein $R^{22}$ is hydrogen, $C_1$-$C_6$-alkyl, or $C_1$-$C_6$-haloalkyl; $J^{30}$ is N; $J^2$-$J^4$, $J^6$-$J^{14}$, $J^{16}$-$J^{21}$, and $J^{23}$-$J^{29}$ are each independently $CR^{23}$ or N, wherein $R^{23}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $J^9$-$J^{14}$ is C where the $R^8$ attaches to the parent molecular formula; provided that one of $J^{16}$-$J^{21}$ is C where the $R^8$ attaches to the parent molecular formula; and provided that one of $J^{23}$-$J^{29}$ is C where the $R^8$ attaches to the parent molecular formula.

In certain embodiments, $R^8$ is selected from the group consisting of:

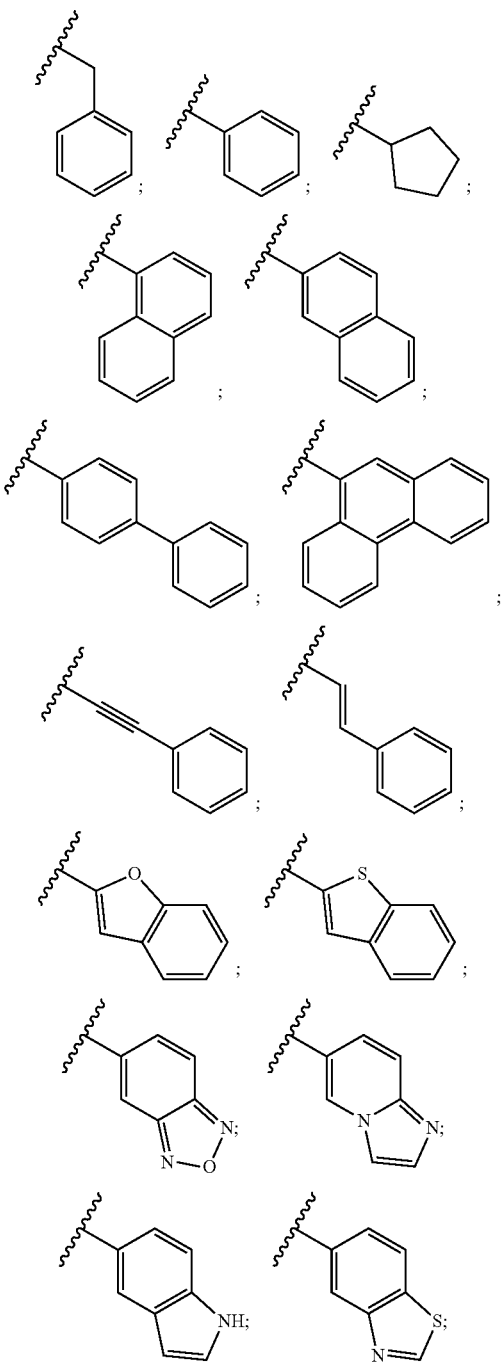

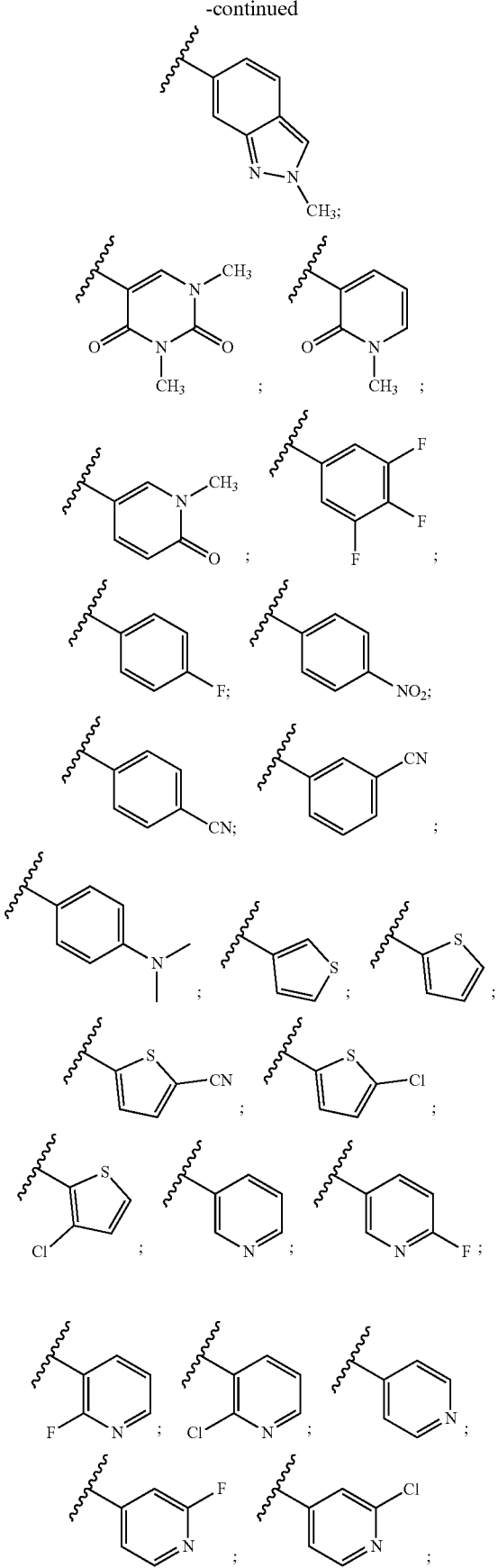
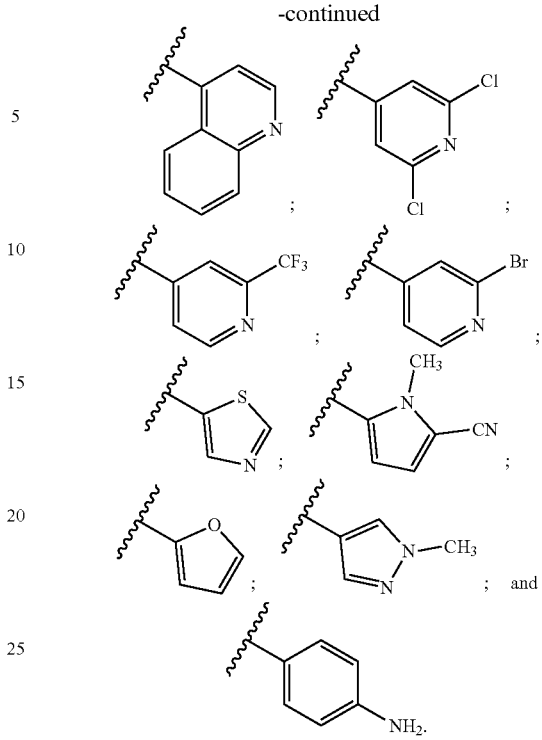

Representative compounds of formula (I-b) include, but are not limited to: 2-(furan-2-ylmethyl)-6,8-diphenylimidazo[1,2-a]pyrazin-3 (7H)-one; 8-cyclopentyl-2-(furan-2-ylmethyl)-6-phenylimidazo[1,2-a]pyrazin-3 (7H)-one; 2-(furan-2-ylmethyl)-8-(naphthalen-1-yl)-6-phenylimidazo[1,2-a]pyrazin-3 (7H)-one; 2-(furan-2-ylmethyl)-8-(naphthalen-2-yl)-6-phenylimidazo[1,2-a]pyrazin-3 (7H)-one; 8-([1,1'-biphenyl]-4-yl)-2-(furan-2-ylmethyl)-6-phenylimidazo[1,2-a]pyrazin-3 (7H)-one; 2-(furan-2-ylmethyl)-8-(phenanthren-9-yl)-6-phenylimidazo[1,2-a]pyrazin-3 (7H)-one; 2-(furan-2-ylmethyl)-6-phenyl-8-(phenylethynyl)imidazo[1,2-a]pyrazin-3 (7H)-one; (E)-2-(furan-2-ylmethyl)-6-phenyl-8-styrylimidazo[1,2-a]pyrazin-3 (7H)-one; 8-(benzofuran-2-yl)-2-(furan-2-ylmethyl)-6-phenylimidazo[1,2-a]pyrazin-3 (7H)-one; 8-(benzo[b]thiophen-2-yl)-2-(furan-2-ylmethyl)-6-phenylimidazo[1,2-a]pyrazin-3 (7H)-one; 8-(benzo[c][1,2,5]oxadiazol-5-yl)-2-(furan-2-ylmethyl)-6-phenylimidazo[1,2-a]pyrazin-3 (7H)-one; 2-(furan-2-ylmethyl)-8-(imidazo[1,2-a]pyridin-6-yl)-6-phenylimidazo[1,2-a]pyrazin-3 (7H)-one; 2-(furan-2-ylmethyl)-8-(1H-indol-5-yl)-6-phenylimidazo[1,2-a]pyrazin-3 (7H)-one; 8-(benzo[d]thiazol-5-yl)-2-(furan-2-ylmethyl)-6-phenylimidazo[1,2-a]pyrazin-3 (7H)-one; 2-(furan-2-ylmethyl)-8-(2-methyl-2H-indazol-6-yl)-6-phenylimidazo[1,2-a]pyrazin-3 (7H)-one; 5-(2-(furan-2-ylmethyl)-3-oxo-6-phenyl-3,7-dihydroimidazo[1,2-a]pyrazin-8-yl)-1,3-dimethylpyrimidine-2,4(1H,3H)-dione; 2-(furan-2-ylmethyl)-8-(1-methyl-2-oxo-1,2-dihydropyridin-3-yl)-6-phenylimidazo[1,2-a]pyrazin-3(7H)-one; 2-(furan-2-ylmethyl)-8-(1-methyl-6-oxo-1,6-dihydropyridin-3-yl)-6-phenylimidazo[1,2-a]pyrazin-3(7H)-one; 2-(furan-2-ylmethyl)-6-phenyl-8-(3,4,5-trifluorophenyl)imidazo[1,2-a]pyrazin-3 (7H)-one; 8-(4-fluorophenyl)-2-(furan-2-ylmethyl)-6-phenylimidazo[1,2-a]pyrazin-3 (7H)-one; 2-(furan-2-ylmethyl)-8-(4-nitrophenyl)-6-phenylimidazo[1,2-a]pyrazin-3 (7H)-one; 4-(2-(furan-2-ylmethyl)-3-oxo-6-phenyl-3,7-dihydroimidazo[1,2-a]pyrazin-8-yl)benzonitrile;

3-(2-(furan-2-ylmethyl)-3-oxo-6-phenyl-3,7-dihydroimidazo[1,2-a]pyrazin-8-yl)benzonitrile; 8-(4-(dimethylamino)phenyl)-2-(furan-2-ylmethyl)-6-phenylimidazo[1,2-a]pyrazin-3 (7H)-one; 2-(furan-2-ylmethyl)-6-phenyl-8-(thiophen-3-yl)imidazo[1,2-a]pyrazin-3 (7H)-one; 2-(furan-2-ylmethyl)-6-phenyl-8-(thiophen-2-yl)imidazo[1,2-a]pyrazin-3 (7H)-one; 5-(2-(furan-2-ylmethyl)-3-oxo-6-phenyl-3,7-dihydroimidazo[1,2-a]pyrazin-8-yl)thiophene-2-carbonitrile; 8-(5-chlorothiophen-2-yl)-2-(furan-2-ylmethyl)-6-phenylimidazo[1,2-a]pyrazin-3 (7H)-one; 8-(3-chlorothiophen-2-yl)-2-(furan-2-ylmethyl)-6-phenylimidazo[1,2-a]pyrazin-3 (7H)-one; 2-(furan-2-ylmethyl)-6-phenyl-8-(pyridin-3-yl)imidazo[1,2-a]pyrazin-3 (7H)-one; 8-(6-fluoropyridin-3-yl)-2-(furan-2-ylmethyl)-6-phenylimidazo[1,2-a]pyrazin-3 (7H)-one; 8-(2-fluoropyridin-3-yl)-2-(furan-2-ylmethyl)-6-phenylimidazo[1,2-a]pyrazin-3 (7H)-one; 8-(2-chloropyridin-3-yl)-2-(furan-2-ylmethyl)-6-phenylimidazo[1,2-a]pyrazin-3(7H)-one; 2-(furan-2-ylmethyl)-6-phenyl-8-(pyridin-4-yl)imidazo[1,2-a]pyrazin-3 (7H)-one; 8-(2-fluoropyridin-4-yl)-2-(furan-2-ylmethyl)-6-phenylimidazo[1,2-a]pyrazin-3 (7H)-one; 8-(2-chloropyridin-4-yl)-2-(furan-2-ylmethyl)-6-phenylimidazo[1,2-a]pyrazin-3 (7H)-one; 2-(furan-2-ylmethyl)-6-phenyl-8-(quinolin-4-yl)imidazo[1,2-a]pyrazin-3 (7H)-one; 8-(2,6-dichloropyridin-4-yl)-2-(furan-2-ylmethyl)-6-phenylimidazo[1,2-a]pyrazin-3 (7H)-one; 2-(furan-2-ylmethyl)-6-phenyl-8-(2-(trifluoromethyl)pyridin-4-yl)imidazo[1,2-a]pyrazin-3 (7H)-one; 8-(2-bromopyridin-4-yl)-2-(furan-2-ylmethyl)-6-phenylimidazo[1,2-a]pyrazin-3 (7H)-one; 2-(furan-2-ylmethyl)-6-phenyl-8-(thiazol-5-yl)imidazo[1,2-a]pyrazin-3 (7H)-one; 5-(2-(furan-2-ylmethyl)-3-oxo-6-phenyl-3,7-dihydroimidazo[1,2-a]pyrazin-8-yl)-1-methyl-1H-pyrrole-2-carbonitrile; and pharmaceutically acceptable salts thereof.

In certain embodiments, the compound of formula (I) is the compound of formula (I-c),

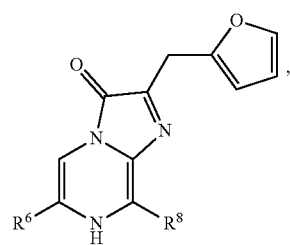

(I-c)

wherein $R^6$ is alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; and $R^8$ is alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; wherein said alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl; provided that the following compounds are excluded from formula (I-c): 8-benzyl-2-(furan-2-ylmethyl)-6-phenylimidazo[1,2-a]pyrazin-3(7H)-one; and 8-benzyl-2-(furan-2-ylmethyl)-6-(4-hydroxyphenyl)imidazo[1,2-a]pyrazin-3 (7H)-one.

In certain embodiments, $R^6$ is phenyl, naphthyl, tricyclic aryl, biphenyl (e.g., 1,4-biphenyl), or heteroaryl (e.g., a monocyclic or bicyclic ring system), wherein the phenyl, naphthyl, biphenyl, tricyclic aryl, and heteroaryl are independently optionally substituted with 1-3 substituents independently selected from the group consisting of halogen (e.g., fluoro), nitro, cyano, $C_1$-$C_6$alkyl (e.g., methyl), $C_1$-$C_6$haloalkyl, amino, $C_1$-$C_6$alkylamino, $C_1$-$C_6$dialkylamino, hydroxy, and $C_1$-$C_6$alkoxy (e.g., methoxy); and $R^8$ is $C_1$-$C_3$alkyl substituted with phenyl, $C_2$alkenyl substituted with phenyl, $C_2$alkynyl substituted with phenyl, phenyl, cycloalkyl, naphthyl, biphenyl, tricyclic aryl, heteroaryl (e.g., a monocyclic or bicyclic ring system), or heterocycle, wherein each phenyl, cycloalkyl, naphthyl, biphenyl, tricyclic aryl, heteroaryl, and heterocycle in $R^8$ is independently optionally substituted with 1-3 substituents independently selected from the group consisting of oxo, halogen (e.g., fluoro, chloro, bromo), nitro, cyano, $C_1$-$C_6$alkyl (e.g., methyl), $C_1$-$C_6$haloalkyl (e.g., $CF_3$), amino, $C_1$-$C_6$alkylamino, $C_1$-$C_6$dialkylamino (e.g., dimethylamino), hydroxy, and $C_1$-$C_6$alkoxy.

In certain embodiments, $R^6$ is aryl, bicyclic aryl, tricyclic aryl, biphenyl, heteroaryl, bicyclic heteroaryl, or tricyclic heteroaryl; substituted with 0, 1, 2, or 3 substituents, each independently selected from the group consisting of halogen, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^6$ is phenyl, bicyclic aryl, tricyclic aryl, biphenyl, monocyclic heteroaryl, bicyclic heteroaryl, or tricyclic heteroaryl; substituted with 0, 1, 2, or 3 substituents, each independently selected from the group consisting of halogen, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^6$ is

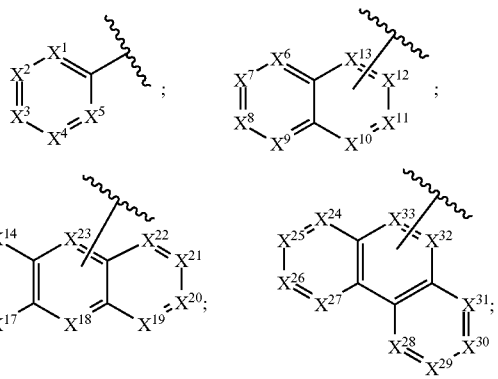

-continued

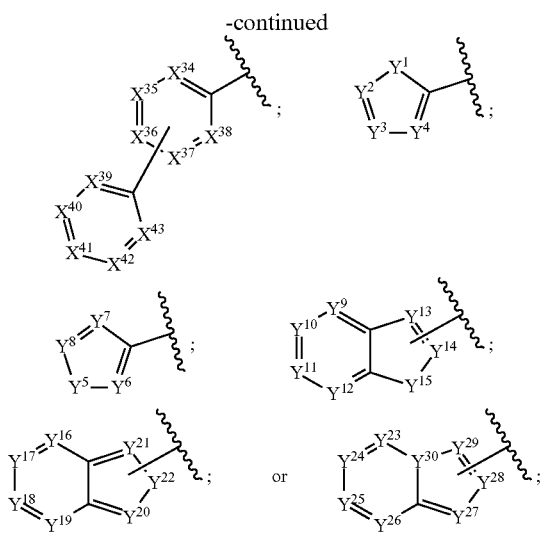

wherein $X^1$-$X^{43}$ are each independently $CR^1$ or N, wherein $R^{11}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $X^6$-$X^{13}$ is C where the $R^6$ attaches to the parent molecular formula; provided that one of $X^{14}$-$X^{23}$ is C where the $R^6$ attaches to the parent molecular formula; provided that one of $X^{24}$-$X^{33}$ is C where the $R^6$ attaches to the parent molecular formula; provided that one of $X^{34}$-$X^{38}$ is C to attach to the ring containing $X^{39}$-$X^{43}$; $Y^1$, $Y^5$, $Y^{15}$, and $Y^{22}$ are O, S, or $NR^{12}$, wherein $R^{12}$ is hydrogen, $C_1$-$C_6$-alkyl, or $C_1$-$C_6$-haloalkyl; $Y^{30}$ is N; $Y^2$-$Y^4$, $Y^6$-$Y^{14}$, $Y^{16}$-$Y^{21}$, and $Y^{23}$-$Y^{29}$ are each independently $CR^{13}$ or N, wherein $R^{13}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $Y^9$-$Y^{14}$ is C where the $R^6$ attaches to the parent molecular formula; provided that one of $Y^{16}$-$Y^{21}$ is C where the $R^6$ attaches to the parent molecular formula; and provided that one of $Y^{23}$-$Y^{29}$ is C where the $R^6$ attaches to the parent molecular formula.

In certain embodiments, $R^6$ is selected from the group consisting of:

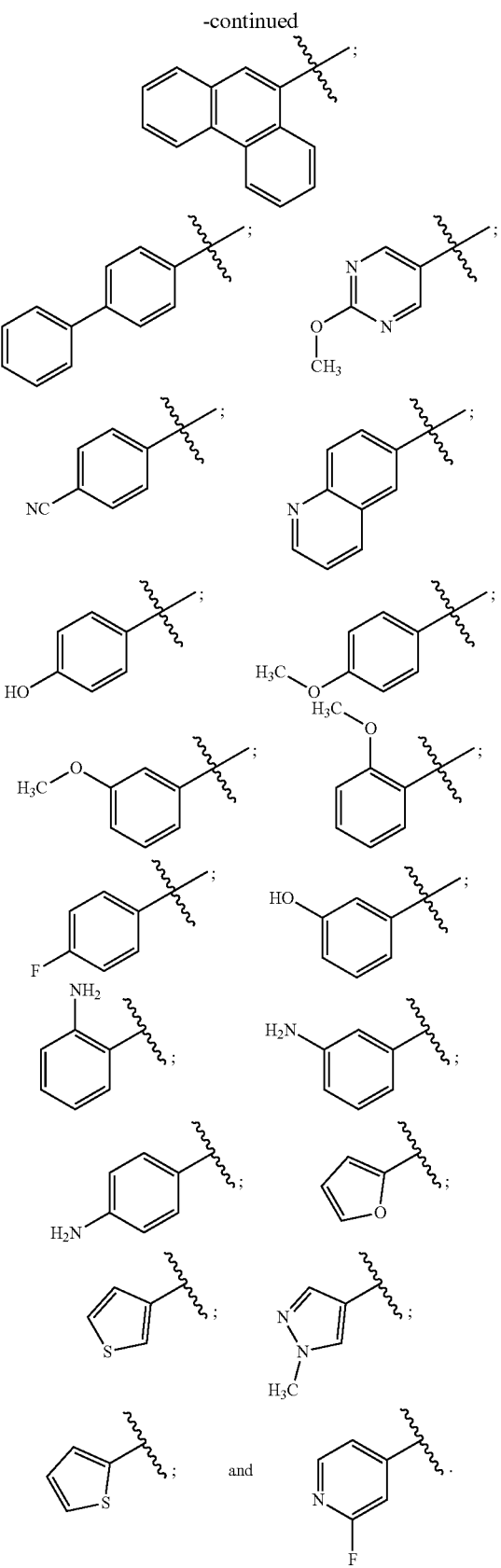

In certain embodiments, $R^8$ is aryl, bicyclic aryl, tricyclic aryl, biphenyl, heteroaryl, bicyclic heteroaryl, tricyclic heteroaryl, heterocycle, or cycloalkyl; substituted with 0, 1, 2, or 3 substituents, each independently selected from the group consisting of halogen, =O, =S, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^8$ is phenyl, bicyclic aryl, tricyclic aryl, biphenyl, monocyclic heteroaryl, bicyclic heteroaryl, tricyclic heteroaryl, heterocycle, or cycloalkyl; substituted with 0, 1, 2, or 3 substituents, each independently selected from the group consisting of halogen, =O, =S, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^8$ is

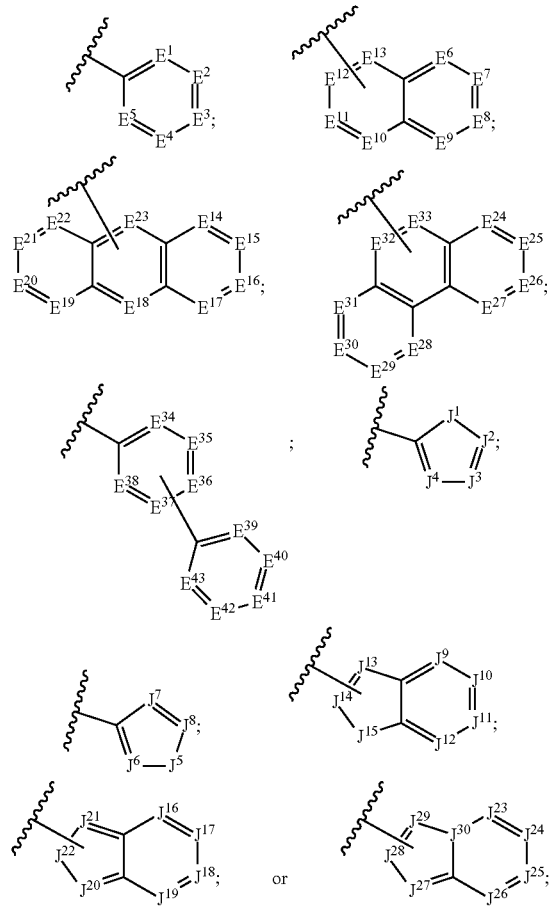

wherein $E^1$-$E^{43}$ are each independently $CR^{21}$ or N, wherein $R^{21}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $E^6$-$E^{13}$ is C where the $R^8$ attaches to the parent molecular formula; provided that one of $E^{14}$-$E^{23}$ is C where the $R^8$ attaches to the parent molecular formula; provided that one of $E^{24}$-$E^{33}$ is C where the $R^8$ attaches to the parent molecular formula; provided that one of $E^{34}$-$E^{38}$ is C to attach to the ring containing $E^{39}$-$E^{43}$; $J^1$, $J^5$, $J^{15}$, and $J^{22}$ are O, S, or $NR^{22}$, wherein $R^{22}$ is hydrogen, $C_1$-$C_6$-alkyl, or $C_1$-$C_6$-haloalkyl; $J^{30}$ is N; $J^2$-$J^4$, $J^6$-$J^{14}$, $J^{16}$-$J^{21}$, and $J^{23}$-$J^{29}$ are each independently $CR^{23}$ or N, wherein $R^{23}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $J^9$-$J^{14}$ is C where the $R^8$ attaches to the parent molecular formula; provided that one of $J^{16}$-$J^{21}$ is C where the $R^8$ attaches to the parent molecular formula; and provided that one of $J^{23}$-$J^{29}$ is C where the $R^8$ attaches to the parent molecular formula.

In certain embodiments, $R^8$ is selected from the group consisting of:

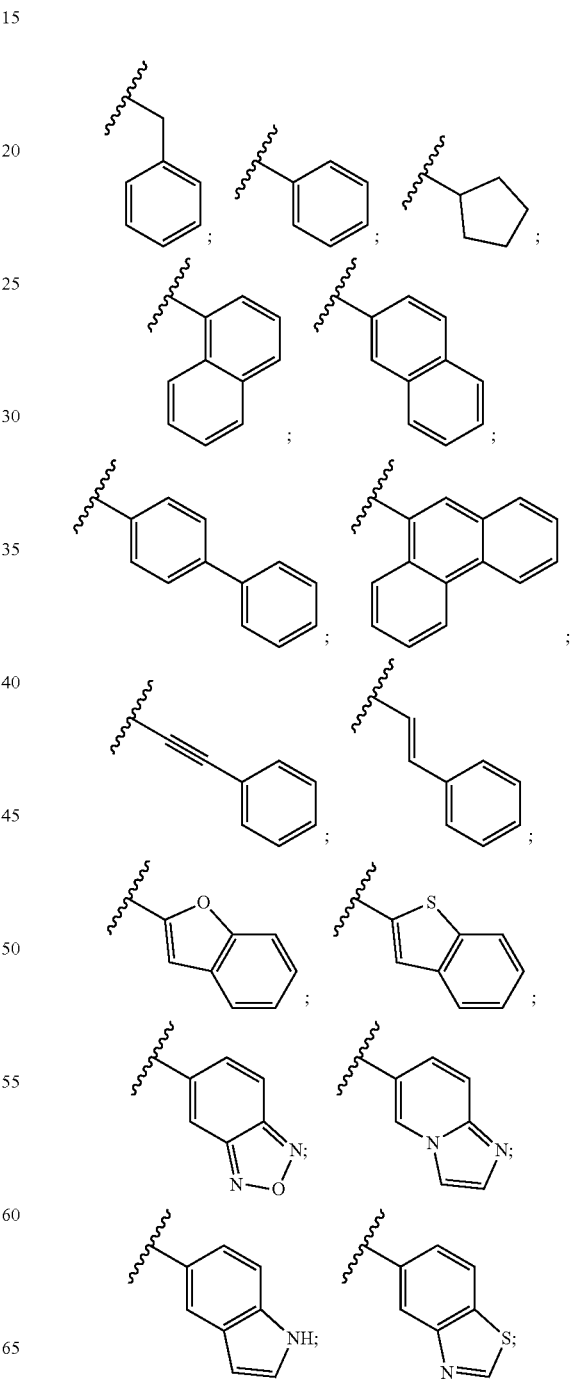

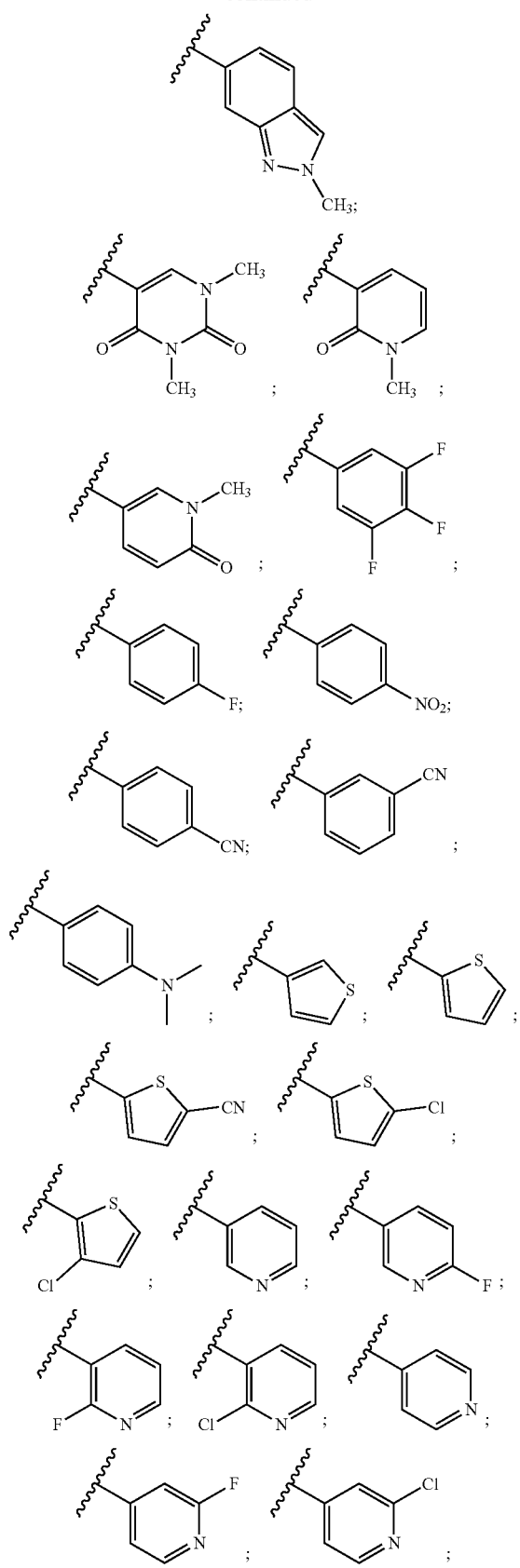

Representative compounds of formula (I-c) include, but are not limited to: 6,8-di(furan-2-yl)-2-(furan-2-ylmethyl)imidazo[1,2-a]pyrazin-3 (7H)-one; 2-(furan-2-ylmethyl)-6,8-di(thiophen-2-yl)imidazo[1,2-a]pyrazin-3(7H)-one; 2-(furan-2-ylmethyl)-6-(1-methyl-1H-pyrazol-3-yl)-8-(1-methyl-1H-pyrazol-4-yl)imidazo[1,2-a]pyrazin-3(7H)-one; 8-(2-fluoropyridin-4-yl)-2-(furan-2-ylmethyl)-6-(thiophen-2-yl)imidazo[1,2-a]pyrazin-3 (7H)-one; 5-(2-(furan-2-ylmethyl)-3-oxo-6-(thiophen-2-yl)-3,7-dihydroimidazo[1,2-a]pyrazin-8-yl)thiophene-2-carbonitrile; 26,8-bis(2-fluoropyridin-4-yl)-2-(furan-2-ylmethyl)imidazo[1,2-a]pyrazin-3 (7H)-one; 2-(furan-2-ylmethyl)-6-phenyl-8-(phenylethynyl)imidazo[1,2-a]pyrazin-3 (7H)-one; 6-(4-aminophenyl)-2-(furan-2-ylmethyl)-8-(quinolin-4-yl)imidazo[1,2-a]pyrazin-3 (7H)-one; 5-(6-(4-aminophenyl)-2-(furan-2-ylmethyl)-3-oxo-3,7-dihydroimidazo[1,2-a]pyrazin-8-yl)thiophene-2-carbonitrile; 6,8-bis(4-aminophenyl)-2-(furan-2-ylmethyl)imidazo[1,2-a]pyrazin-3 (7H)-one; 2-(furan-2-ylmethyl)-6-(4-hydroxyphenyl)-8-(quinolin-4-yl)imidazo[1,2-a]pyrazin-3 (7H)-one; 5-(2-(furan-2-ylmethyl)-6-(4-hydroxyphenyl)-3-oxo-3,7-dihydroimidazo[1,2-a]pyrazin-8-yl)thiophene-2-carbonitrile;

and pharmaceutically acceptable salts thereof.

In certain embodiments, the compound of formula (I) is the compound of formula (I-d),

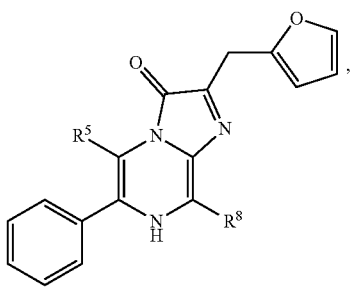

(I-d)

wherein R⁵ is hydrogen, halogen, hydroxy, cyano, nitro, amino, alkylamino, dialkylamino, alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; and R⁸ is alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; wherein said alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl; provided that the following compound is excluded from formula (I-d): 8-benzyl-2-(furan-2-ylmethyl)-6-phenylimidazo[1,2-a]pyrazin-3(7H)-one.

In certain embodiments, R⁵ is hydrogen, C₁-C₆alkyl, C₂₋₆alkenyl, C₂₋₆alkynyl (e.g., C₂alkynyl), phenyl, cyano, amino, C₁-C₆alkylamino, C₁-C₆dialkylamino (e.g., dimethylamino), or C₁-C₆alkoxy (e.g., methoxy), wherein the phenyl is optionally substituted with 1-3 substituents independently selected from the group consisting of halogen, nitro, cyano, C₁-C₆alkyl, C₁-C₆haloalkyl, amino, C₁-C₆alkylamino, C₁-C₆dialkylamino, hydroxy, and C₁-C₆alkoxy; and R⁸ is C₁-C₃alkyl substituted with phenyl, C₂alkenyl substituted with phenyl, C₂alkynyl substituted with phenyl, phenyl, cycloalkyl, naphthyl, biphenyl, tricyclic aryl, heteroaryl (e.g., a monocyclic or bicyclic ring system), or heterocycle, wherein each phenyl, cycloalkyl, naphthyl, biphenyl, tricyclic aryl, heteroaryl, and heterocycle in R⁸ is independently optionally substituted with 1-3 substituents independently selected from the group consisting of oxo, halogen (e.g., fluoro, chloro, bromo), nitro, cyano, C₁-C₆alkyl (e.g., methyl), C₁-C₆haloalkyl (e.g., CF₃), amino, C₁-C₆alkylamino, C₁-C₆dialkylamino (e.g., dimethylamino), hydroxy, and C₁-C₆alkoxy.

In certain embodiments, R⁵ is hydrogen, cyano, C₁-C₆-alkyl, C₁-C₆-alkoxy, C₁-C₆-haloalkyl, C₁-C₆-haloalkoxy, C₁-C₆-alkylamino, C₁-C₆-dialkylamino, or phenyl.

In certain embodiments, R⁵ is hydrogen.

In certain embodiments, R⁵ is halogen, hydroxy, cyano, nitro, amino, alkylamino, dialkylamino, alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl;

wherein said alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, R⁵ is cyano, C₁-C₆-alkyl, C₁-C₆-alkoxy, C₁-C₆-haloalkyl, C₁-C₆-haloalkoxy, C₁-C₆-alkylamino, C₁-C₆-dialkylamino, or phenyl.

In certain embodiments, R⁸ is aryl, bicyclic aryl, tricyclic aryl, biphenyl, heteroaryl, bicyclic heteroaryl, tricyclic heteroaryl, heterocycle, or cycloalkyl; substituted with 0, 1, 2, or 3 substituents, each independently selected from the group consisting of halogen, =O, =S, hydroxy, cyano, amino, nitro, C₁-C₆-alkyl, C₁-C₆-alkoxy, C₁-C₆-haloalkyl, C₁-C₆-haloalkoxy, C₁-C₆-alkylamino, and C₁-C₆-dialkylamino.

In certain embodiments, R⁸ is phenyl, bicyclic aryl, tricyclic aryl, biphenyl, monocyclic heteroaryl, bicyclic heteroaryl, tricyclic heteroaryl, heterocycle, or cycloalkyl; substituted with 0, 1, 2, or 3 substituents, each independently selected from the group consisting of halogen, =O, =S, hydroxy, cyano, amino, nitro, C₁-C₆-alkyl, C₁-C₆-alkoxy, C₁-C₆-haloalkyl, C₁-C₆-haloalkoxy, C₁-C₆-alkylamino, and C₁-C₆-dialkylamino.

In certain embodiments, R⁸ is

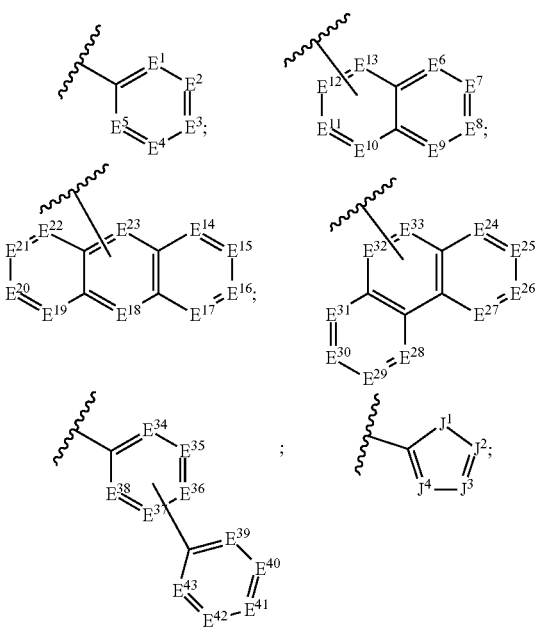

-continued

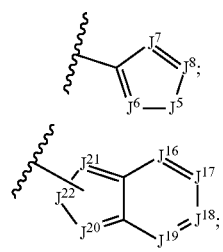

wherein $E^1$-$E^{43}$ are each independently $CR^{21}$ or N, wherein $R^{21}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $E^6$-$E^{13}$ is C where the $R^8$ attaches to the parent molecular formula; provided that one of $E^{14}$-$E^{23}$ is C where the $R^8$ attaches to the parent molecular formula; provided that one of $E^{24}$-$E^{33}$ is C where the $R^8$ attaches to the parent molecular formula; provided that one of $E^{34}$-$E^{38}$ is C to attach to the ring containing $E^{39}$-$E^{43}$; $J^1$, $J^5$, $J^{15}$, and $J^{22}$ are O, S, or $NR^{22}$, wherein $R^{22}$ is hydrogen, $C_1$-$C_6$-alkyl, or $C_1$-$C_6$-haloalkyl; $J^{30}$ is N; $J^2$-$J^4$, $J^6$-$J^{14}$, $J^{16}$-$J^{21}$, and $J^{23}$-$J^{29}$ are each independently $CR^{23}$ or N, wherein $R^{23}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $J^9$-$J^{14}$ is C where the $R^8$ attaches to the parent molecular formula; provided that one of $J^{16}$-$J^{21}$ is C where the $R^8$ attaches to the parent molecular formula; and provided that one of $J^{23}$-$J^{29}$ is C where the $R^8$ attaches to the parent molecular formula.

In certain embodiments, $R^8$ is selected from the group consisting of:

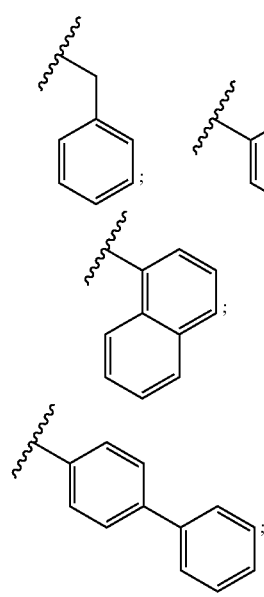

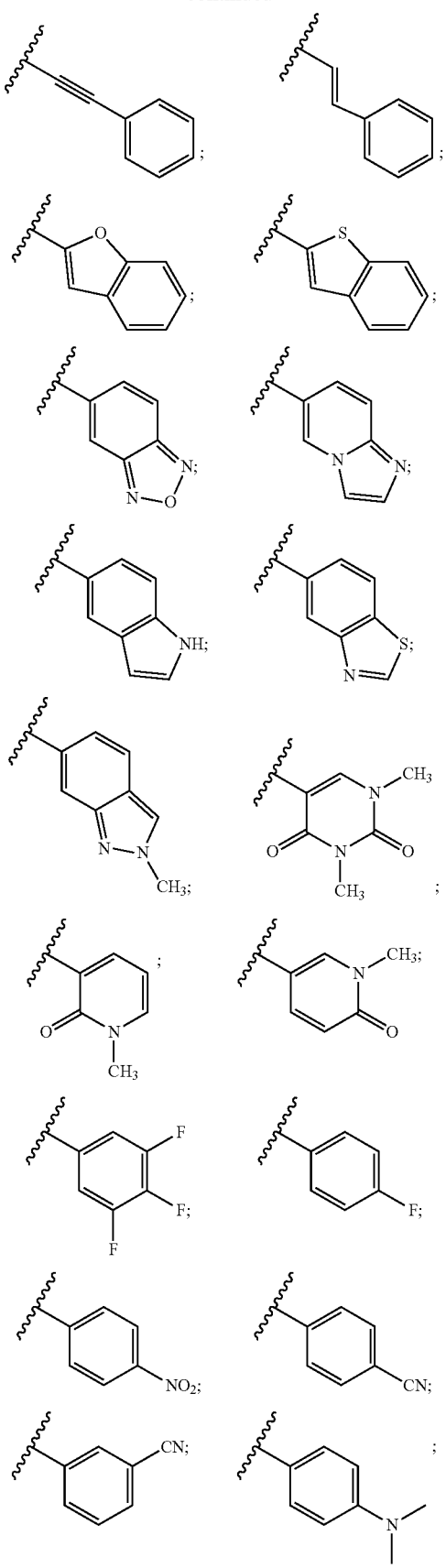

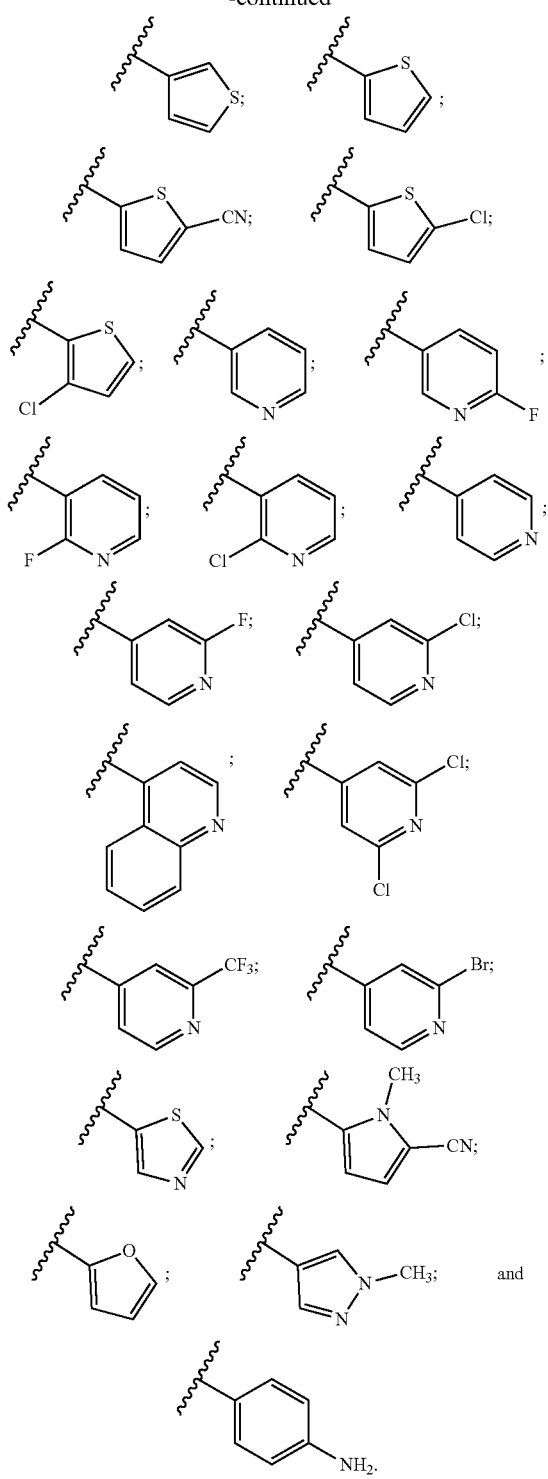

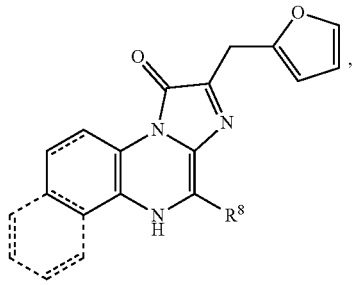

wherein each - - - indicates an optional bond; and $R^8$ is alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; wherein said alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, $R^8$ is aryl, bicyclic aryl, tricyclic aryl, biphenyl, heteroaryl, bicyclic heteroaryl, tricyclic heteroaryl, heterocycle, or cycloalkyl; substituted with 0, 1, 2, or 3 substituents, each independently selected from the group consisting of halogen, =O, =S, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^8$ is phenyl, bicyclic aryl, tricyclic aryl, biphenyl, monocyclic heteroaryl, bicyclic heteroaryl, tricyclic heteroaryl, heterocycle, or cycloalkyl; substituted with 0, 1, 2, or 3 substituents, each independently selected from the group consisting of halogen, =O, =S, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^8$ is

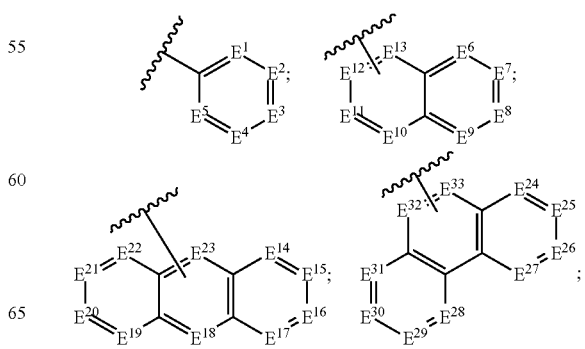

Representative compounds of formula (I-d) include, but are not limited to: 2-(furan-2-ylmethyl)-5,6,8-triphenylimidazo[1,2-a]pyrazin-3 (7H)-one; 2-(furan-2-ylmethyl)-3-oxo-6,8-diphenyl-3,7-dihydroimidazo[1,2-a]pyrazine-5-carbonitrile; and pharmaceutically acceptable salts thereof.

In certain embodiments, the compound of formula (I) is the compound of formula (I-e), -continued

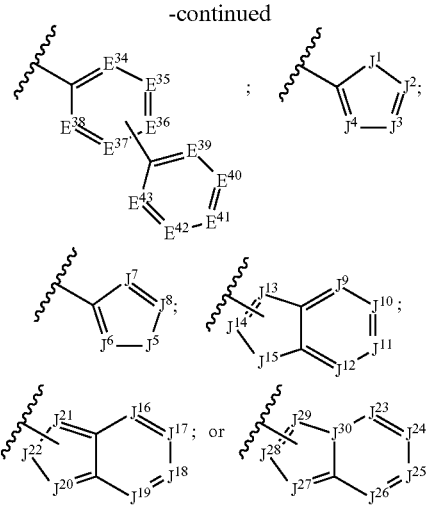

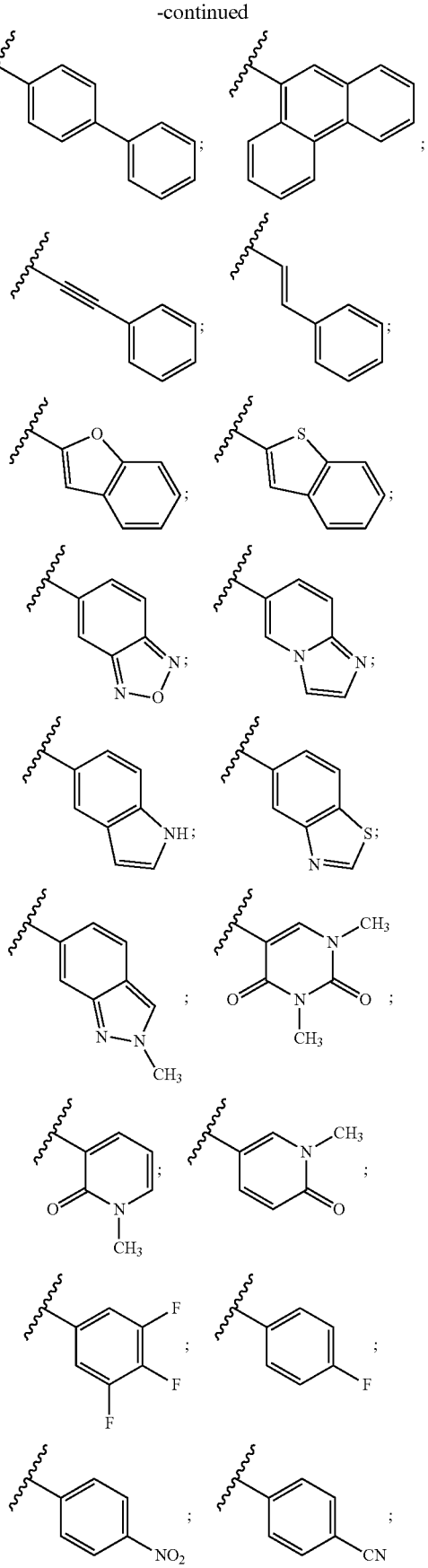

wherein $E^1$-$E^{43}$ are each independently $CR^{21}$ or N, wherein $R^{21}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $E^6$-$E^{13}$ is C where the $R^8$ attaches to the parent molecular formula; provided that one of $E^{14}$-$E^{23}$ is C where the $R^8$ attaches to the parent molecular formula; provided that one of $E^{24}$-$E^{33}$ is C where the $R^8$ attaches to the parent molecular formula; provided that one of $E^{34}$-$E^{38}$ is C to attach to the ring containing $E^{39}$-$E^{43}$; $J^1$, $J^5$, $J^{15}$, and $J^{22}$ are O, S, or $NR^{22}$, wherein $R^{22}$ is hydrogen, $C_1$-$C_6$-alkyl, or $C_1$-$C_6$-haloalkyl; $J^{30}$ is N; $J^2$-$J^4$, $J^6$-$J^{14}$, $J^{16}$-$J^{21}$, and $J^{23}$-$J^{29}$ are each independently $CR^{23}$ or N, wherein $R^{23}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $J^9$-$J^{14}$ is C where the $R^8$ attaches to the parent molecular formula; provided that one of $J^{16}$-$J^{21}$ is C where the $R^8$ attaches to the parent molecular formula; and provided that one of $J^{23}$-$J^{29}$ is C where the $R^8$ attaches to the parent molecular formula.

In certain embodiments, $R^8$ is selected from the group consisting of:

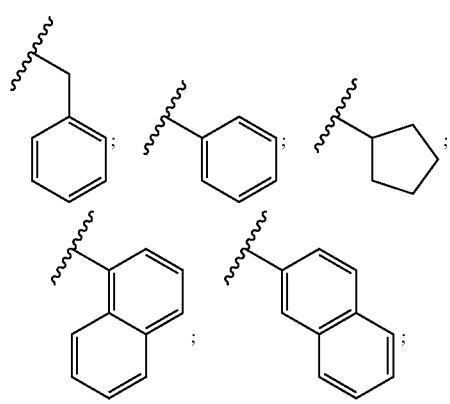

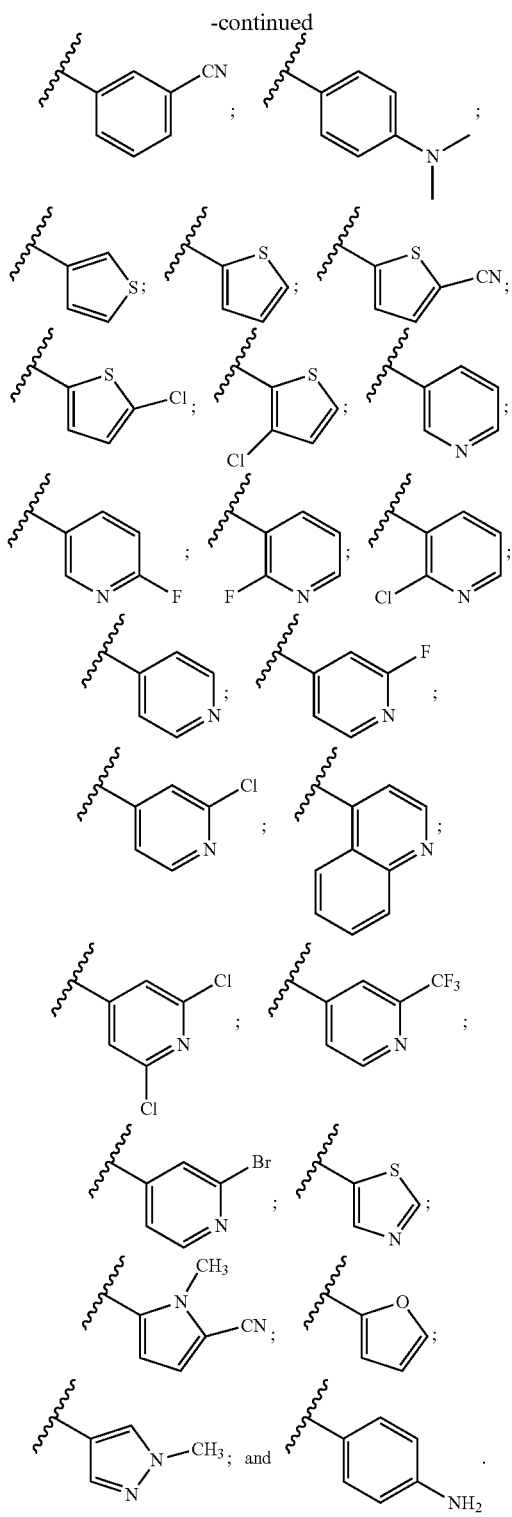

Representative compounds of formula (I-e) include, but are not limited to: 4-(2-chloropyridin-4-yl)-2-(furan-2-ylmethyl)imidazo[1,2-a]quinoxalin-1 (5H)-one; 5-(2-(furan-2-ylmethyl)-1-oxo-1,5-dihydroimidazo[1,2-a]quinoxalin-4-yl)thiophene-2-carbonitrile; 12-(2-chloropyridin-4-yl)-2-(furan-2-ylmethyl)-5,11-dihydrobenzo[f]imidazo[1,2-a]quinoxalin-3 (6H)-one; 5-(2-(furan-2-ylmethyl)-3-oxo-3,5,6,11-tetrahydrobenzo[f]imidazo[1,2-a]quinoxalin-12-yl)thiophene-2-carbonitrile; 2-(furan-2-ylmethyl)-12-(quinolin-4-yl)-5,11-dihydrobenzo[f]imidazo[1,2-a]quinoxalin-3 (6H)-one; and pharmaceutically acceptable salts thereof.

Additional representative compounds of formula (I) include, but are not limited to: 8-(2-chloropyridin-4-yl)-2-(furan-2-ylmethyl)-6-(4-hydroxyphenyl)imidazo[1,2-a]pyrazin-3 (7H)-one; 12-(2-chloropyridin-4-yl)-2-(furan-2-ylmethyl)benzo[f]imidazo[1,2-a]quinoxalin-3 (11H)-one; 5-(2-(furan-2-ylmethyl)-3-oxo-3,11-dihydrobenzo[f]imidazo[1,2-a]quinoxalin-12-yl)thiophene-2-carbonitrile; 2-(furan-2-ylmethyl)-12-(quinolin-4-yl)benzo[f]imidazo[1,2-a]quinoxalin-3(11H)-one; and pharmaceutically acceptable salts thereof.

Also disclosed are compounds of formula (II):

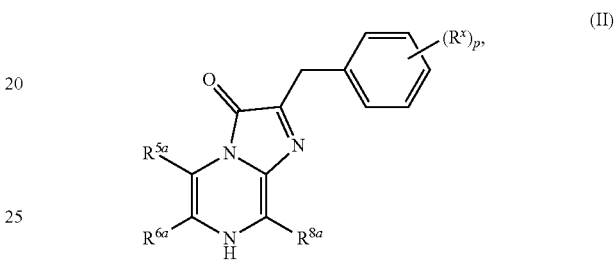

or tautomers, or pharmaceutically acceptable salts thereof; wherein $R^x$ is halogen, hydroxy, cyano, nitro, amino, alkylamino, dialkylamino, alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; p is 0, 1, 2, 3, 4, or 5; $R^{5a}$ is hydrogen, halogen, hydroxy, cyano, nitro, amino, alkylamino, dialkylamino, alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; $R^{6a}$ is alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; or $R^{5a}$ and $R^{6a}$ together with the atoms to which they are attached, form a 5- or 6-membered partially unsaturated or fully unsaturated ring, the 5- or 6-membered ring optionally containing 1, 2 or 3 heteroatoms or heteroatom groups each independently selected from the group consisting of O, N, S, NO, SO and $SO_2$ as ring members, the 5- or 6-membered ring optionally fused to an aryl, heteroaryl, heterocycle, or cycloalkyl, the 5- or 6-membered ring substituted with 0, 1, 2, 3, or 4 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl; and $R^{8a}$ is alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; wherein said alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl; provided that $R^x$ is not 4-hydroxy when p is 1, $R^{5a}$ is not hydrogen, or $R^{8a}$ is not benzyl, or any combination thereof.

In certain embodiments according to formula (II), $R^x$ is halogen, nitro, cyano, $C_1$-$C_6$alkyl, $C_1$-$C_6$haloalkyl, amino, $C_1$-$C_6$alkylamino, $C_1$-$C_6$dialkylamino, or $C_1$-$C_6$alkoxy; p is 0, 1, 2, 3, 4, or 5; $R^{5a}$ is $C_1$-$C_6$alkyl, $C_{2-6}$alkenyl, $C_{2-6}$alkynyl (e.g., $C_2$alkynyl), phenyl, cyano, amino, $C_1$-$C_6$alkylamino, $C_1$-$C_6$dialkylamino (e.g., dimethylamino), or $C_1$-$C_6$alkoxy (e.g., methoxy), wherein the phenyl is optionally substituted with 1-3 substituents independently selected from the group consisting of halogen, nitro, cyano, $C_1$-$C_6$alkyl, $C_1$-$C_6$haloalkyl, amino, $C_1$-$C_6$alkylamino, $C_1$-$C_6$dialkylamino, hydroxy, and $C_1$-$C_6$alkoxy; $R^{6a}$ is phenyl, naphthyl, tricyclic aryl, biphenyl (e.g., 1,4-biphenyl), or heteroaryl (e.g., a monocyclic or bicyclic ring system), wherein the phenyl, naphthyl, biphenyl, tricyclic aryl, and heteroaryl are independently optionally substituted with 1-3 substituents independently selected from the group consisting of halogen (e.g., fluoro), nitro, cyano, $C_1$-$C_6$alkyl (e.g., methyl), $C_1$-$C_6$haloalkyl, amino, $C_1$-$C_6$alkylamino, $C_1$-$C_6$dialkylamino, hydroxy, and $C_1$-$C_6$alkoxy (e.g., methoxy); or $R^{5a}$ and $R^{6a}$ together with the atoms to which they are attached, form a 5- or 6-membered partially unsaturated or fully unsaturated carbocyclic ring, the 5- or 6-membered carbocyclic ring being optionally fused to a phenyl, the 5- or 6-membered carbocyclic ring being optionally substituted with 1-3 substituents independently selected from the group consisting of oxo, halogen, nitro, cyano, $C_1$-$C_6$alkyl, $C_1$-$C_6$haloalkyl, amino, $C_1$-$C_6$alkylamino, $C_1$-$C_6$dialkylamino, hydroxy, and $C_1$-$C_6$alkoxy; and $R^{8a}$ is $C_2$alkenyl substituted with phenyl, $C_2$alkynyl substituted with phenyl, phenyl, cycloalkyl, naphthyl, biphenyl, tricyclic aryl, heteroaryl (e.g., a monocyclic or bicyclic ring system), or heterocycle, wherein each phenyl, cycloalkyl, naphthyl, biphenyl, tricyclic aryl, heteroaryl, and heterocycle in $R^{8a}$ is independently optionally substituted with 1-3 substituents independently selected from the group consisting of oxo, halogen (e.g., fluoro, chloro, bromo), nitro, cyano, $C_1$-$C_6$alkyl (e.g., methyl), $C_1$-$C_6$haloalkyl (e.g., $CF_3$), amino, $C_1$-$C_6$alkylamino, $C_1$-$C_6$dialkylamino (e.g., dimethylamino), hydroxy, and $C_1$-$C_6$alkoxy. In certain embodiments, $R^{5a}$ is cyano, $C_1$-$C_6$dialkylamino, $C_2$-$C_6$alkynyl, or $C_1$-$C_6$alkoxy. In some embodiments, p is 0.

In certain embodiments, $R^{5a}$ is halogen, hydroxy, cyano, nitro, amino, alkylamino, dialkylamino, alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl. In certain embodiments, $R^{5a}$ is cyano, dialkylamino, alkynyl, or alkoxy. In certain embodiments, $R^{5a}$ is cyano, dimethylamino, ethynyl, or methoxy.

In certain embodiments, $R^{5a}$ is halogen, hydroxy, cyano, nitro, amino, alkylamino, dialkylamino, alkyl, alkenyl, alkynyl, alkoxy, heteroalkyl, phenyl, bicyclic aryl, tricyclic aryl, monocyclic heteroaryl, bicyclic heteroaryl, tricyclic heteroaryl, heterocycle, cycloalkyl, or cycloalkenyl. In certain embodiments, $R^{5a}$ is cyano, $C_1$-$C_6$dialkylamino, $C_2$-$C_6$alkynyl, or $C_1$-$C_6$alkoxy. In certain embodiments, $R^{5a}$ is cyano, dimethylamino, ethynyl, or methoxy.

In certain embodiments, $R^{6a}$ is aryl, bicyclic aryl, tricyclic aryl, biphenyl, heteroaryl, bicyclic heteroaryl, or tricyclic heteroaryl; substituted with 0, 1, 2, or 3 substituents, each independently selected from the group consisting of halogen, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^{6a}$ is phenyl, bicyclic aryl, tricyclic aryl, biphenyl, monocyclic heteroaryl, bicyclic heteroaryl, or tricyclic heteroaryl; substituted with 0, 1, 2, or 3 substituents, each independently selected from the group consisting of halogen, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^{6a}$ is

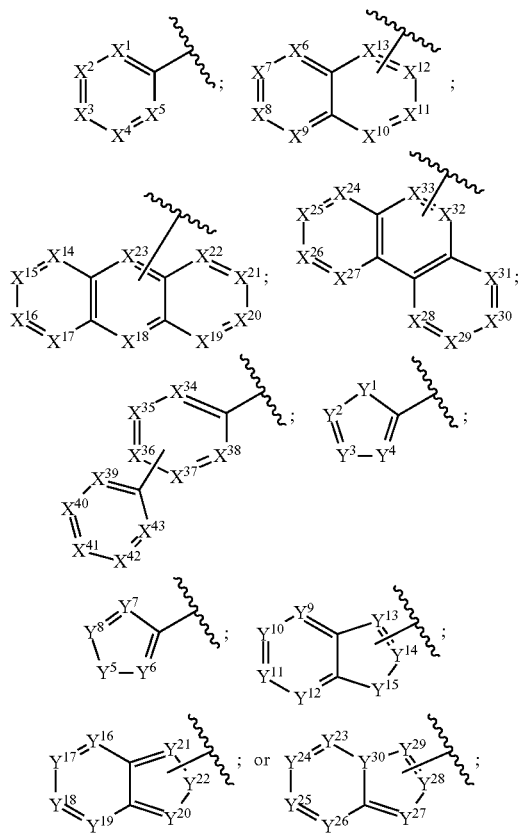

wherein $X^1$-$X^{43}$ are each independently $CR^{11}$ or N, wherein $R^{11}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $X^6$-$X^3$ is C where the $R^{6a}$ attaches to the parent molecular formula; provided that one of $X^{14}$-$X^{23}$ is C where the $R^{6a}$ attaches to the parent molecular formula; provided that one of $X^{24}$-$X^{33}$ is C where the $R^{6a}$ attaches to the parent molecular formula; provided that one of $X^{34}$-$X^{38}$ is C to attach to the ring containing $X^{39}$-$X^{43}$; $Y^1$, $Y^5$, $Y^{15}$, and $Y^{22}$ are O, S, or $NR^{12}$, wherein $R^{12}$ is hydrogen, $C_1$-$C_6$-alkyl, or $C_1$-$C_6$-haloalkyl; $Y^{30}$ is N; $Y^2$-$Y^4$, $Y^6$-$Y^{14}$, $Y^{16}$-$Y^{21}$, and $Y^{23}$-$Y^{29}$ are each independently $CR^{13}$ or N, wherein $R^{13}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $Y^9$-$Y^{14}$ is C where the $R^{6a}$ attaches to the parent molecular formula; provided that one of $Y^{16}$-$Y^{21}$ is C where the $R^{6a}$ attaches to the parent molecular formula; and provided that one of $Y^{23}$-$Y^{29}$ is C where the $R^{6a}$ attaches to the parent molecular formula.

In certain embodiments, $R^{6a}$ is selected from the group consisting of:

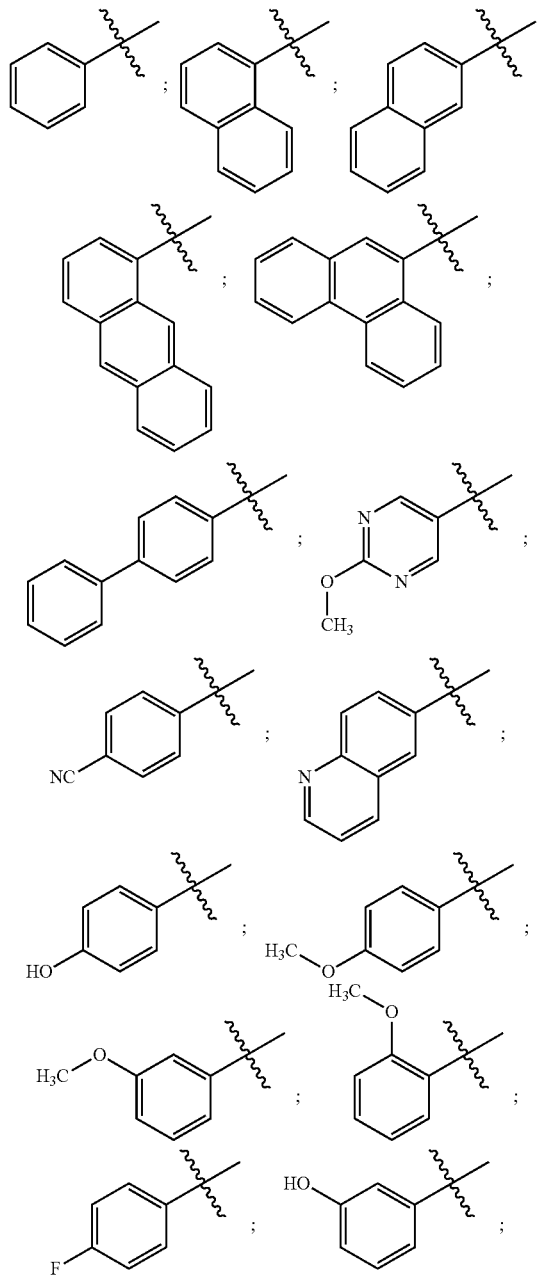

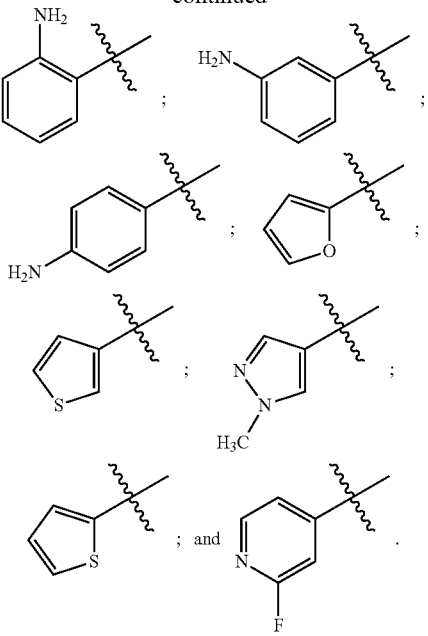

In certain embodiments, $R^{5a}$ and $R^{6a}$ together with the atoms to which they are attached, form a 6-membered partially unsaturated or fully unsaturated ring, the 6-membered ring optionally containing 1, 2 or 3 heteratoms or heteroatom groups each independently selected from the group consisting of O, N, S, NO, SO and $SO_2$ as ring members, the 6-membered ring optionally fused to an aryl, 5- or 6-membered heteroaryl, 5- or 6-membered heterocycle, or 5-, 6- or 7-membered cycloalkyl, the 6-membered ring and the optionally fused ring each independently substituted with 0, 1, 2, 3, or 4 substituents each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, $R^{5a}$ and $R^{6a}$ together with the atoms to which they are attached, form a ring system selected from the group consisting of:

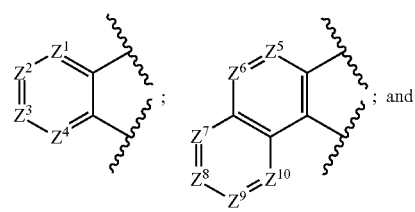

49

-continued

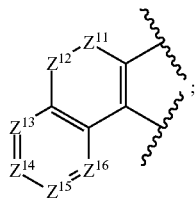

wherein $Z^1$-$Z^{10}$ and $Z^{13}$-$Z^{16}$ are each independently $CR^{14}$ or N, wherein $R^{14}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; and $Z^{11}$ and $Z^{12}$ are each independently $CR^{15}R^{16}$, $NR^{17}$, O, or S; wherein $R^{15}$ and $R^{16}$, at each occurrence, are each independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; and $R^{17}$, at each occurrence, is independently selected from the group consisting of hydrogen, $C_1$-$C_6$-alkyl, and $C_1$-$C_6$-haloalkyl.

In certain embodiments, $R^{5a}$ and $R^{6a}$ together with the atoms to which they are attached, form a ring system selected from the group consisting of:

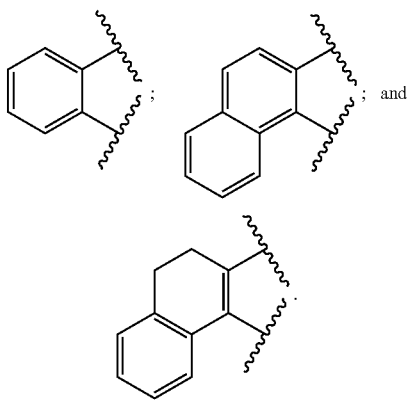

In certain embodiments, $R^{8a}$ is aryl, bicyclic aryl, tricyclic aryl, biphenyl, heteroaryl, bicyclic heteroaryl, tricyclic heteroaryl, heterocycle, or cycloalkyl; substituted with 0, 1, 2, or 3 substituents, each independently selected from the group consisting of halogen, =O, =S, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

In certain embodiments, $R^{8a}$ is phenyl, bicyclic aryl, tricyclic aryl, biphenyl, monocyclic heteroaryl, bicyclic heteroaryl, tricyclic heteroaryl, heterocycle, or cycloalkyl; substituted with 0, 1, 2, or 3 substituents, each independently selected from the group consisting of halogen, =O, =S, hydroxy, cyano, amino, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylamino, and $C_1$-$C_6$-dialkylamino.

50

In certain embodiments, $R^{8a}$ is

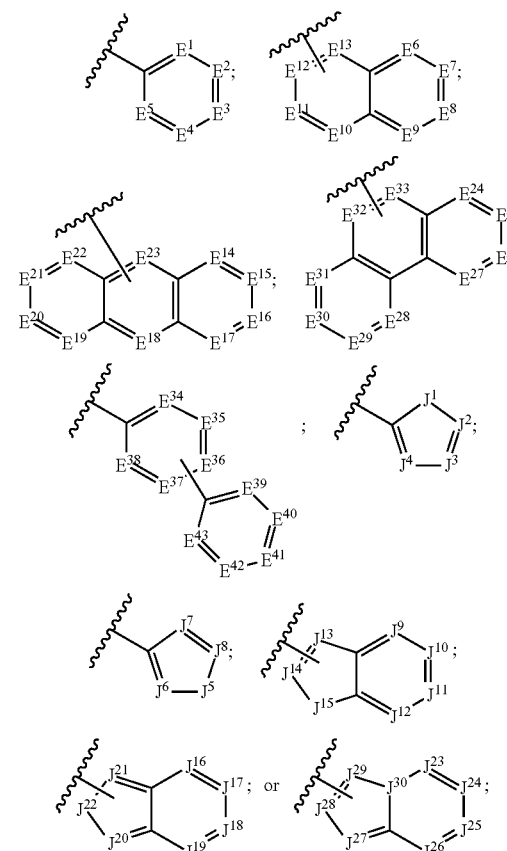

wherein $E^1$-$E^{43}$ are each independently $CR^{21}$ or N, wherein $R^{21}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $E^6$-$E^{13}$ is C where the $R^{8a}$ attaches to the parent molecular formula; provided that one of $E^{14}$-$E^{23}$ is C where the $R^{8a}$ attaches to the parent molecular formula; provided that one of $E^{24}$-$E^{33}$ is C where the $R^{8a}$ attaches to the parent molecular formula; provided that one of $E^{34}$-$E^{38}$ is C to attach to the ring containing $E^{39}$-$E^{43}$; $J^1$, $J^5$, $J^{15}$, and $J^{22}$ are O, S, or $NR^{22}$, wherein $R^{22}$ is hydrogen, $C_1$-$C_6$-alkyl, or $C_1$-$C_6$-haloalkyl; $J^{30}$ is N; $J^2$-$J^4$, $J^6$-$J^{14}$, $J^{16}$-$J^{21}$, and $J^{23}$-$J^{29}$ are each independently $CR^{23}$ or N, wherein $R^{23}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl; provided that one of $J^9$-$J^{14}$ is C where the $R^{8a}$ attaches to the parent molecular formula; provided that one of $J^{16}$-$J^{21}$ is C where the $R^{8a}$ attaches to the parent molecular formula; and provided that one of $J^{23}$-$J^{29}$ is C where the $R^{8a}$ attaches to the parent molecular formula.

In certain embodiments, $R^{8a}$ is selected from the group consisting of:

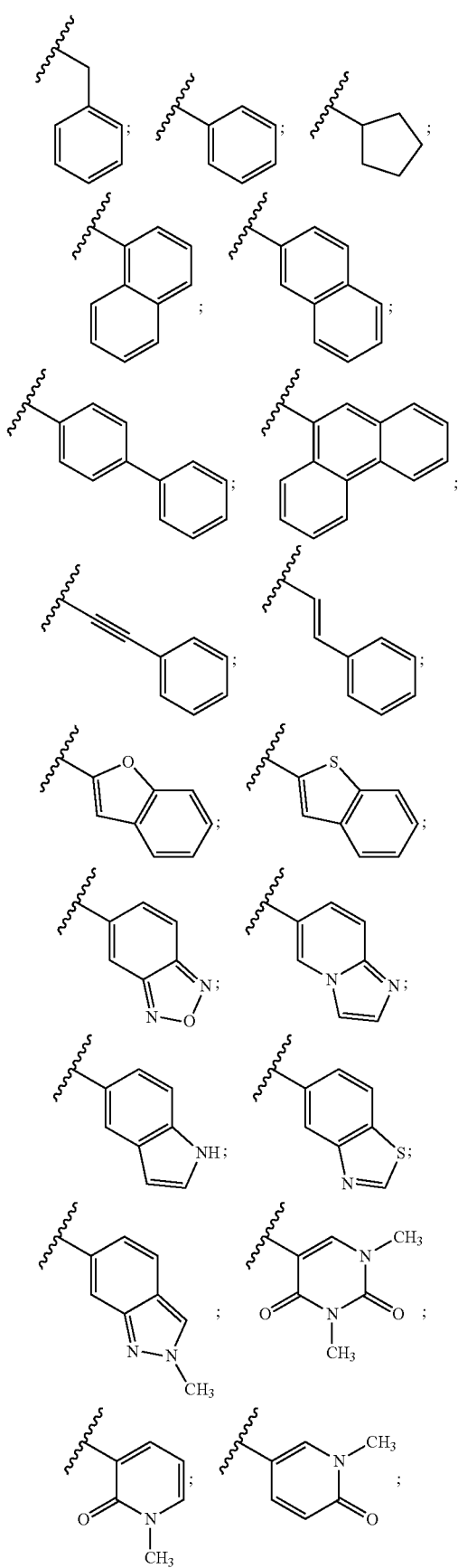
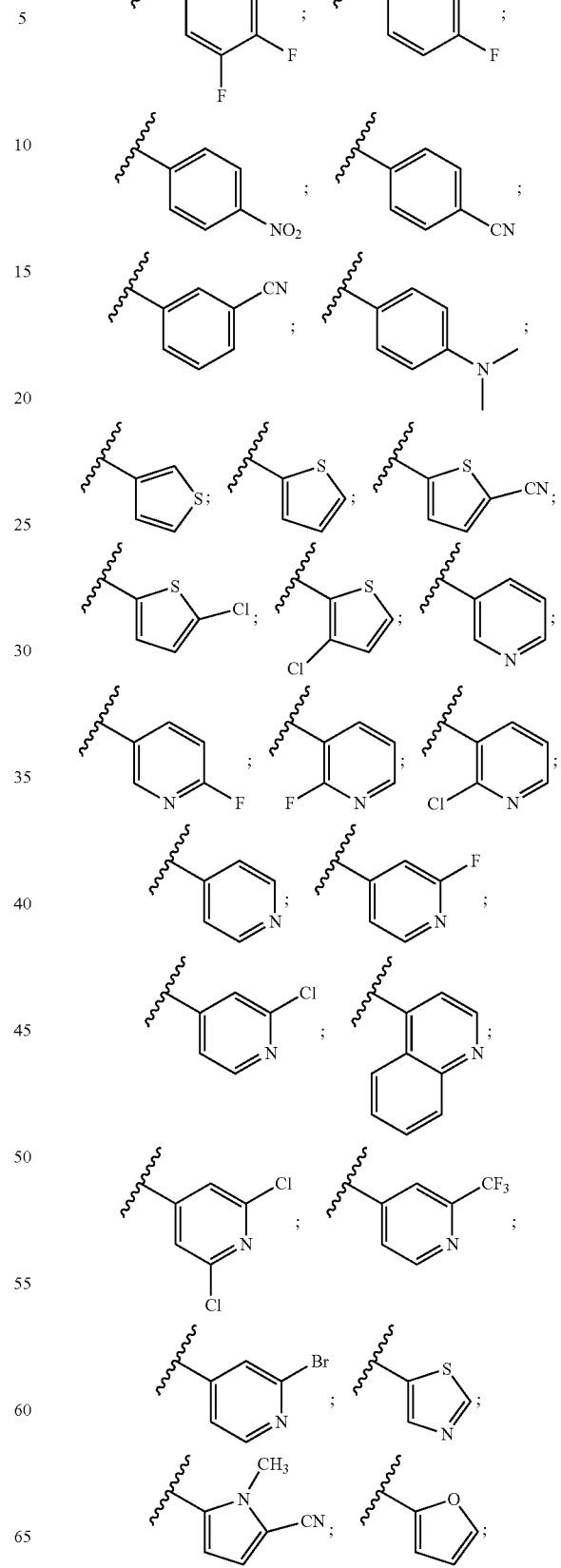

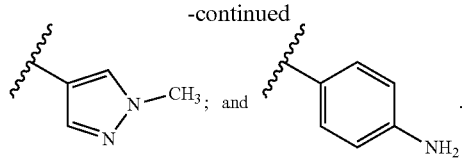

In certain embodiments, $R^{5a}$ is hydrogen, halogen, hydroxy, cyano, nitro, amino, alkylamino, dialkylamino, alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; $R^{6a}$ is aryl; and $R^{8a}$ is aryl; wherein said alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, $R^{5a}$ is hydrogen, halogen, hydroxy, cyano, nitro, amino, alkylamino, dialkylamino, alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, or cycloalkenyl; $R^{6a}$ is phenyl; and $R^{8a}$ is phenyl; wherein said alkyl, alkenyl, alkynyl, alkoxy, heteroalkyl, aryl, bicyclic aryl, tricyclic aryl, heteroaryl, bicyclic heteroaryl, tricyclic heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, $R^{5a}$ is cyano, dialkylamino, alkynyl, or alkoxy; $R^{6a}$ is aryl; and $R^{8a}$ is aryl; wherein said alkyl, alkynyl, alkoxy, and aryl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, $R^{5a}$ is cyano, dialkylamino, alkynyl, or alkoxy; $R^{6a}$ is phenyl; and $R^{8a}$ is phenyl. In certain embodiments, $R^{5a}$ is cyano, dimethylamino, ethynyl, or methoxy; $R^{6a}$ is phenyl; and $R^{8a}$ is phenyl.

In certain embodiments, $R^x$ is not 4-hydroxy when p is 1. In certain embodiments, $R^{5a}$ is not hydrogen. In certain embodiments, $R^{8a}$ is not benzyl.

Representative compounds of formula (II) include, but are not limited to: 2-benzyl-5-ethynyl-6,8-diphenylimidazo[1,2-a]pyrazin-3(7H)-one; 2-benzyl-3-oxo-6,8-diphenyl-3,7-dihydroimidazo[1,2-a]pyrazine-5-carbonitrile 2-benzyl-5-(dimethylamino)-6,8-diphenylimidazo[1,2-a]pyrazin-3(7H)-one; 2-benzyl-5-methoxy-6,8-diphenylimidazo[1,2-a]pyrazin-3 (7H)-one; and pharmaceutically acceptable salts thereof.

Compound names are assigned by using Struct=Name naming algorithm as part of CHEMDRAW® ULTRA v. 12.0.

The compounds may exist as stereoisomers wherein asymmetric or chiral centers are present. The stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof, and these are specifically included within the scope of this invention. Stereoisomers include enantiomers and diastereomers and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Furniss, Hannaford, Smith, and Tatchell, "Vogel's Textbook of Practical Organic Chemistry", 5$^{th}$ edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds may possess tautomeric forms as well as geometric isomers, and that these also constitute an aspect of the invention.

The present disclosure also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^{2}H$, $^{3}H$, $^{13}C$, $^{14}C$ $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements, and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A. Properties of the Compounds

The compounds of formula (I) and formula (II) may be substrates of luciferases to produce luminescence. The compounds may have improved water solubility, improved stability, improved cell permeability, increased biocompatibility with cells, reduced autoluminescence, and/or reduced toxicity.

"Luminescence" refers to the light output of a luciferase under appropriate conditions, e.g., in the presence of a suitable substrate such as a coelenterazine analogue. The light output may be measured as an instantaneous or near-instantaneous measure of light output (which is sometimes referred to as "T=0" luminescence or "flash") at the start of the luminescence reaction, which may be initiated upon addition of the coelenterazine substrate. The luminescence reaction in various embodiments is carried out in a solution. In other embodiments, the luminescence reaction is carried out on a solid support. The solution may contain a lysate, for example from the cells in a prokaryotic or eukaryotic expression system. In other embodiments, expression occurs in a cell-free system, or the luciferase protein is secreted into an extracellular medium, such that, in the latter case, it is not necessary to produce a lysate. In some embodiments, the reaction is started by injecting appropriate materials, e.g., coelenterazine analogue, buffer, etc., into a reaction chamber (e.g., a well of a multiwell plate such as a 96-well plate) containing the luminescent protein. In still other embodiments, the luciferase and/or coelenterazine analogues (e.g., compounds of formula (I) and (II)) are introduced into a host, and measurements of luminescence are made on the host or a portion thereof, which can include a whole organism or cells, tissues, explants, or extracts thereof. The reaction chamber may be situated in a reading device which can measure the light output, e.g., using a luminometer or photomultiplier. The light output or luminescence may also be measured over time, for example in the same reaction chamber for a period of seconds, minutes, hours, etc. The light output or luminescence may be reported as the average over time, the half-life of decay of signal, the sum of the signal over a period of time, or the peak output. Luminescence may be measured in Relative Light Units (RLUs).

Compounds of formula (I) and formula (II) can have an RLU of greater than or equal to 1, greater than or equal to 2, greater than or equal to 3, greater than or equal to 4, greater than or equal to 5, greater than or equal to 10, greater than or equal to 20, greater than or equal to 30, greater than or equal to 40, greater than or equal to 50, or greater than or equal to 100, relative to coelenterazine or a known coelenterazine analogue such as furimazine.

Compounds of formula (I) and formula (II) can have a λmax of 450-700 nanometers, 460-600 nanometers, 470-600 nanometers, 480-600 nanometers, 490-600 nanometers, 500-600 nanometers, 510-600 nanometers, 520-600 nanometers, 530-600 nanometers, 540-600 nanometers, 550-600 nanometers, 560-600 nanometers, 570-600 nanometers, 580-600 nanometers, 590-600 nanometers, 470-590 nanometers, 480-580 nanometers, 490-570 nanometers, 500-560 nanometers, or 510-550 nanometers. Compounds of formula (I) and formula (II) can have a λmax greater than or equal to 450 nanometers, greater than or equal to 460 nanometers, greater than or equal to 470 nanometers, greater than or equal to 480 nanometers, greater than or equal to 490 nanometers, greater than or equal to 500 nanometers, greater than or equal to 510 nanometers, greater than or equal to 520 nanometers, greater than or equal to 530 nanometers, greater than or equal to 540 nanometers, greater than or equal to 550 nanometers, greater than or equal to 560 nanometers, greater than or equal to 570 nanometers, greater than or equal to 580 nanometers, greater than or equal to 590 nanometers, greater than or equal to 600 nanometers, greater than or equal to 610 nanometers, greater than or equal to 620 nanometers, greater than or equal to 630 nanometers, greater than or equal to 640 nanometers, greater than or equal to 650 nanometers, greater than or equal to 660 nanometers, greater than or equal to 670 nanometers, greater than or equal to 680 nanometers, greater than or equal to 690 nanometers, or greater than or equal to 700 nanometers.

"Biocompatibility" refers to the tolerance of a cell (e.g., prokaryotic or eukaryotic) to a coelenterazine analogue (e.g., compounds of formula (I)). Biocompatibility of a coelenterazine analogue is related to the stress it causes on the host cell.

Enhanced biocompatibility of the coelenterazine analogues (e.g., compounds of formula (I)), may be determined by measuring cell viability and/or growth rate of cells. For example, enhanced biocompatibility of the coelenterazine analogues may be determined by measuring cell viability in the absence of luciferase expression of cells exposed to the coelenterazine analogues compared to native or known coelenterazines to determine how compatible and/or toxic the coelenterazine analogues are to the cells.

In particular, enhanced biocompatibility may be determined using cell viability analysis (e.g., using the CELL-TITER-GLO® Luminescent Cell Viability assay), an apoptosis assay (e.g., using the CASPASE-GLO® technology), or another method known in the art. The effect of the disclosed compounds on cell viability or apoptosis may be compared to the effect of native or known coelenterazine analogues on cell viability or apoptosis.

Enhanced biocompatibility may also be determined by measuring the effect of the coelenterazine analogues (e.g., compounds of formula (I)) on cell growth or gene expression. For example, enhanced biocompatibility of the compounds of formula (I) or formula (II) may be determined by measuring the cell number after a period of time or by determining the expression of stress response genes in a sample of cells that are exposed to compounds of formula (I) or formula (II) compared to cells exposed to a native or known coelenterazine or no coelenterazine. The effect of the disclosed compounds on cell growth or gene expression may be compared to a native or known coelenterazine.

A. Synthesis Methods

Compounds of formula (I) and formula (II) may be prepared by synthetic processes or by metabolic processes. Preparation of the compounds by metabolic processes includes those occurring in the human or animal body (in vivo) or processes occurring in vitro.

Compounds of formula (I) and formula (II), wherein the groups $R^5$, $R^6$, $R^8$, $R^{5a}$, $R^{6a}R^{8a}$, $R^x$, and p have the meanings as set forth in the Summary of the Invention section unless otherwise noted, can be synthesized as shown in Schemes 1-5.

Abbreviations which have been used in the descriptions of the Schemes that follow are: $Ac_2O$ for acetic anhydride; CDI for carbonyldiimidazole; MeOH for methanol; TMG for 1,1,3,3-tetramethylguanidine; and TFA for trifluoroacetic acid.

Scheme 1.
Synthesis of intermediates A-C

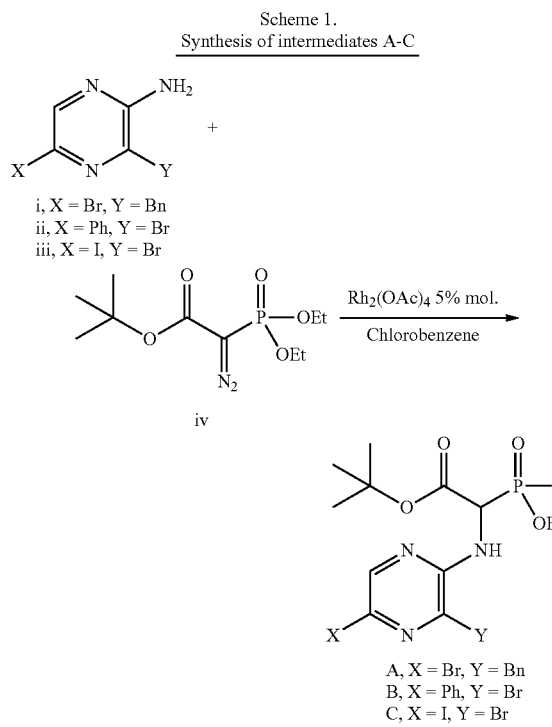

As shown in Scheme 1, intermediates A-C can be prepared from aminopyrazines i-iii. Treatment of i-iii with diazocarbonyl iv, in the presence of $Rh_2(OAc)_4$, can result in formation of aminopyrazine acetophosphonates A-C. Intermediates A-C may be stable at room temperature and provide starting materials for varied analogues.

Scheme 2. Synthesis of compounds of formula (I) and formula (II)

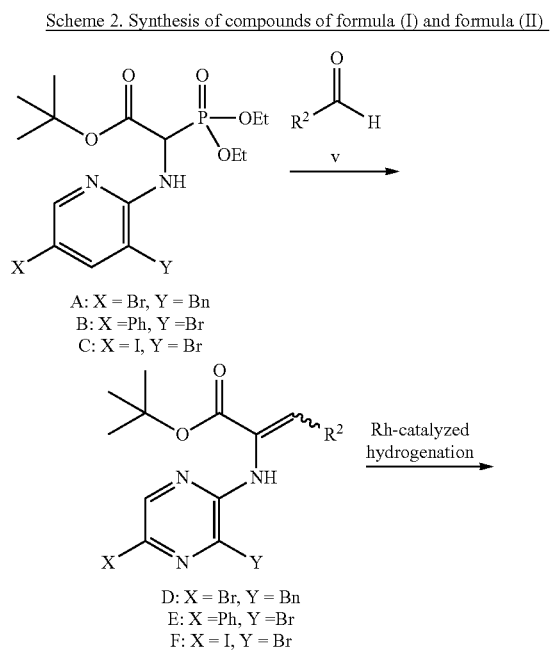

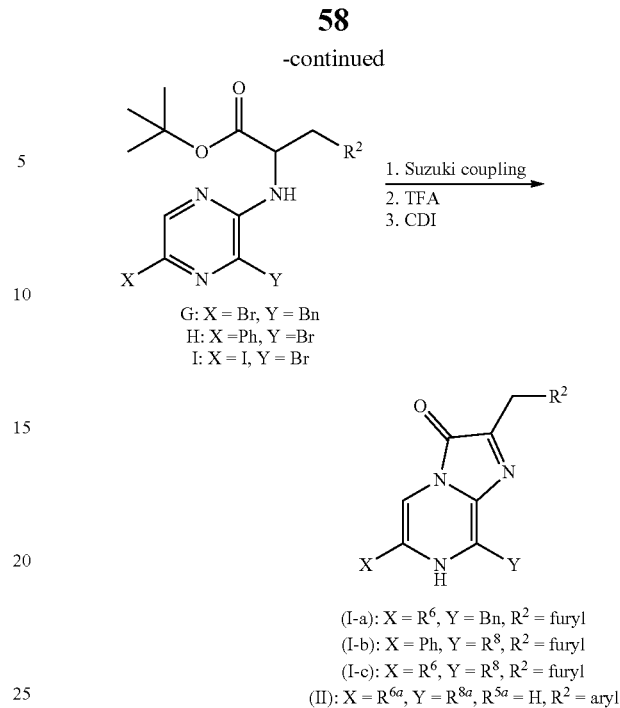

Scheme 2 illustrates the conversion of intermediates A-C to compounds of formula (I) and formula (II). Intermediates A-C can be treated with 1,1,3,3-tetramethylguanidine and undergo Horner-Wadsworth-Emmons olefination with aldehyde v (e.g., furan-2-carbaldehyde or a benzaldehyde) to yield intermediates D-F. Intermediates D-F can be hydrogenated to provide intermediates G-I. Intermediates G-I can undergo Suzuki coupling(s) at one or both of the X and Y positions, followed by treatment with TFA and subsequent cyclization promoted by the addition of carbonyldiimidazole, providing compounds of formula (I) and formula (II).

Scheme 3. Synthesis of compounds of formula (I) and formula (II)

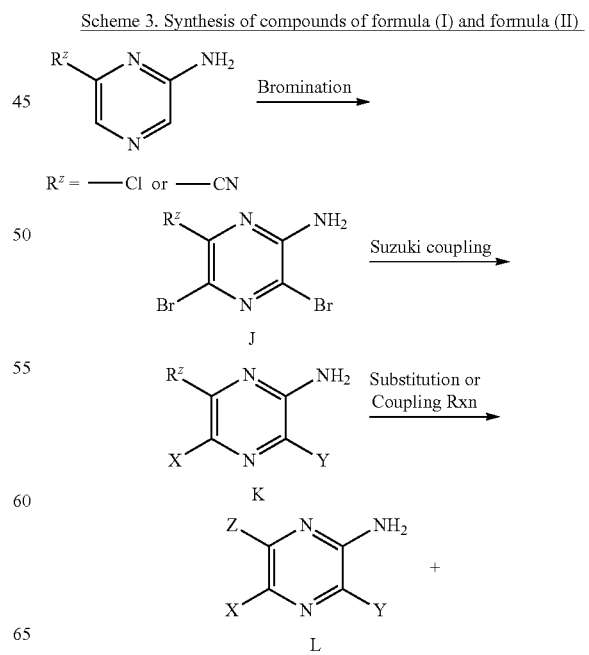

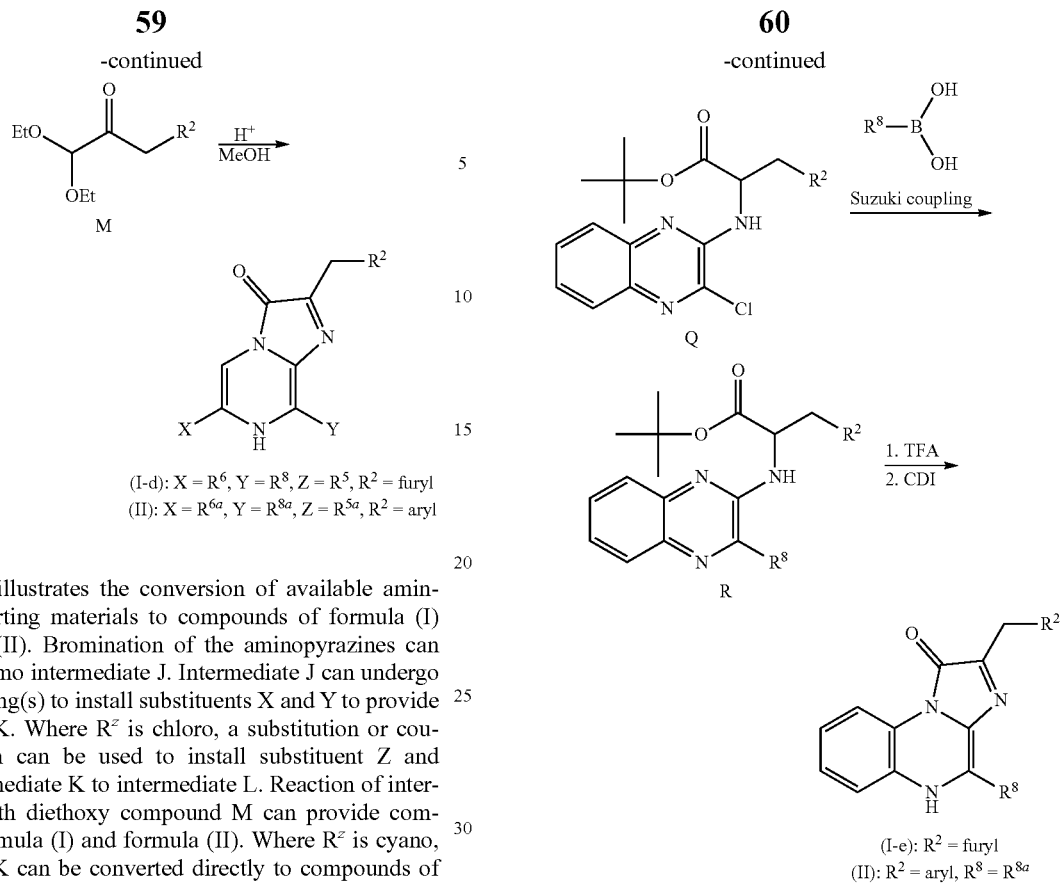

(I-d): X = R⁶, Y = R⁸, Z = R⁵, R² = furyl
(II): X = R⁶ᵃ, Y = R⁸ᵃ, Z = R⁵ᵃ, R² = aryl Scheme 3 illustrates the conversion of available aminopyrazine starting materials to compounds of formula (I) and formula (II). Bromination of the aminopyrazines can provide dibromo intermediate J. Intermediate J can undergo Suzuki coupling(s) to install substituents X and Y to provide intermediate K. Where $R^z$ is chloro, a substitution or coupling reaction can be used to install substituent Z and convert intermediate K to intermediate L. Reaction of intermediate L with diethoxy compound M can provide compounds of formula (I) and formula (II). Where $R^z$ is cyano, intermediate K can be converted directly to compounds of formula (I) and formula (II) by reaction with the diethoxy compound M.

Scheme 4. Synthesis of compounds of formula (I) and formula (II)

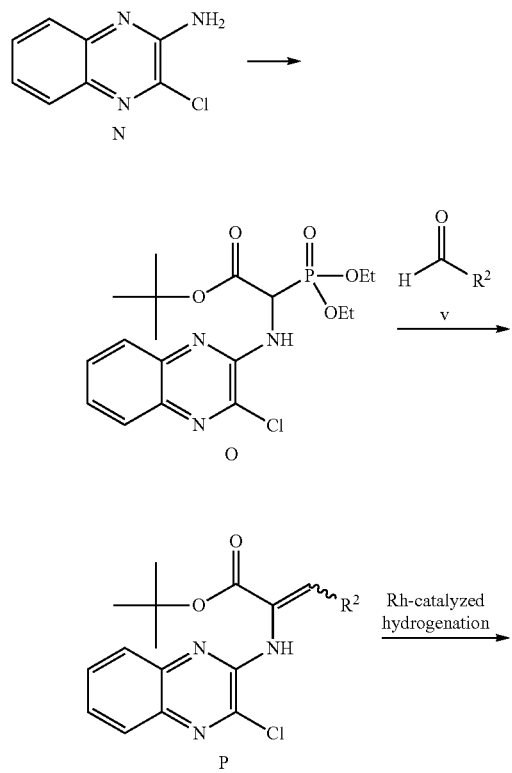

(I-e): R² = furyl
(II): R² = aryl, R⁸ = R⁸ᵃ

Scheme 4 illustrates the preparation of compounds of formula (I) and formula (II). Starting material N can be converted to phosphonate O under standard conditions. Intermediate O can be treated with 1,1,3,3-tetramethylguanidine and undergo Horner-Wadsworth-Emmons olefination with aldehyde v (e.g., furan-2-carbaldehyde or a benzaldehyde) to yield intermediate P. Intermediate P can be hydrogenated to provide intermediate Q. Intermediate Q can undergo Suzuki coupling to intermediate R, followed by treatment with TFA and subsequent cyclization promoted by the addition of carbonyldiimidazole, providing compounds of formula (I) and formula (II).

Scheme 5. Synthesis of compounds of formula (I) and formula (II)

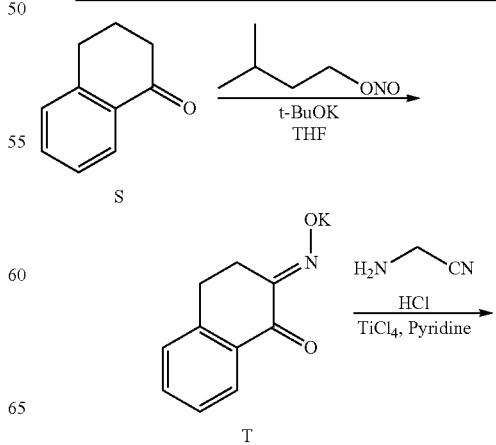

-continued

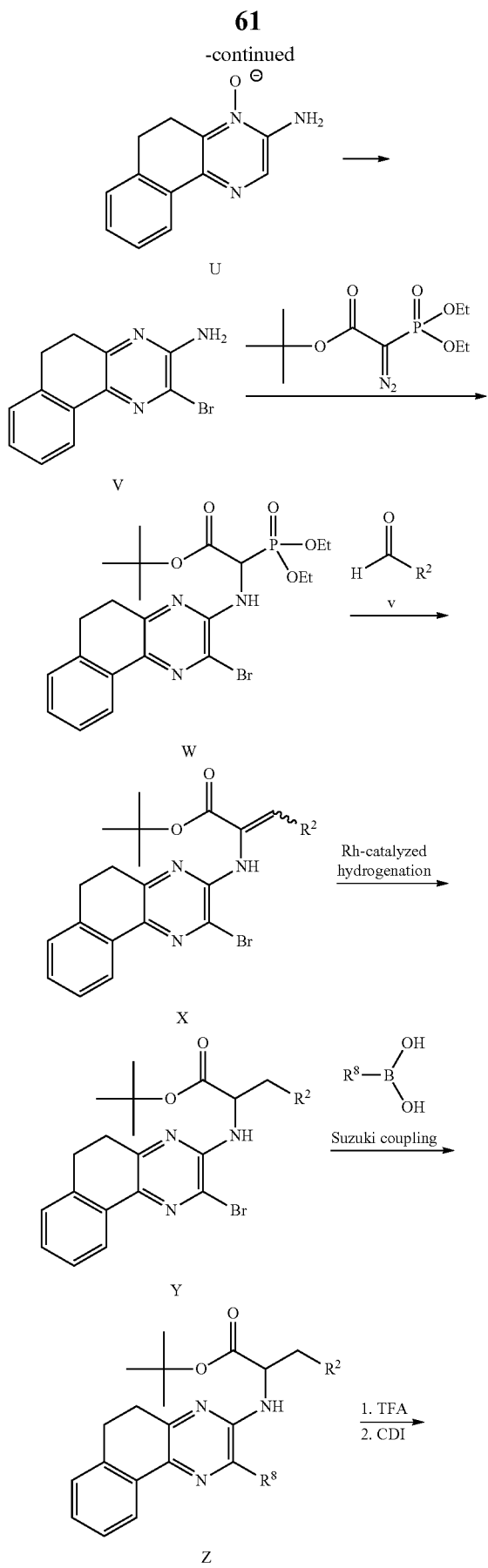

-continued

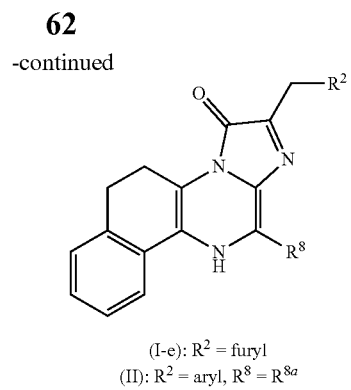

(I-e): $R^2$ = furyl
(II): $R^2$ = aryl, $R^8 = R^{8a}$

Scheme 5 illustrates the preparation of compounds of formula (I) and formula (II). Starting ketone S can undergo reaction with amyl nitrite under basic conditions to provide oxime intermediate T. Intermediate T can be converted to amine U via reaction with 2-aminoacetonitrile and subsequent intramolecular cyclization. Intermediate V can be prepared by bromination and reduction of the N-oxide of intermediate U. N-oxide intermediate U can be reduced with hydrogen in the presence of Ni-Raney catalyst, and the corresponding reduced aminopyrazine can then react with N-bromsuccinimide in dichloromethane to afford compound V. Intermediate V can be converted to phoshonate W under standard conditions. Intermediate W can be treated with 1,1,3,3-tetramethylguanidine and undergo Horner-Wadsworth-Emmons olefination with aldehyde v (e.g., furan-2-carbaldehyde or a benzaldehyde) to yield intermediate X. Intermediate X can be hydrogenated to provide intermediate Y. Intermediate Y can undergo Suzuki coupling to intermediate Z, followed by treatment with TFA, and subsequent cyclization promoted by the addition of carbonyldiimidazole, providing compounds of formula (I) and formula (II).

Optimum reaction conditions and reaction times for each individual step can vary depending on the particular reactants employed and substituents present in the reactants used. Specific procedures are provided in the Examples section. Reactions can be worked up in the conventional manner, e.g., by eliminating the solvent from the residue and further purified according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step) or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material or by resolution of a mixture of the geometric isomers of the compound or intermediates using a standard procedure such as chromatographic separation.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. Methods of Use and Kits

The compounds of the disclosure may be used in any way that luciferase substrates, e.g., coelenterazine analogues, have been used. For example, they may be used in a bioluminogenic method that employs an analogue of coelenterazine to detect one or more molecules in a sample, e.g., an enzyme, a cofactor for an enzymatic reaction, an enzyme substrate, an enzyme inhibitor, an enzyme activator, or OH radicals, or one or more conditions, e.g., redox conditions. The sample may include an animal (e.g., a vertebrate), a plant, a fungus, physiological fluid (e.g., blood, plasma, urine, mucous secretions), a cell, a cell lysate, a cell supernatant, or a purified fraction of a cell (e.g., a subcellular fraction). The presence, amount, spectral distribution, emission kinetics, or specific activity of such a molecule may be detected or quantified. The molecule may be detected or quantified in solution, including multiphasic solutions (e.g., emulsions or suspensions), or on solid supports (e.g., particles, capillaries, or assay vessels).

In certain embodiments, the compounds of formula (I) or formula (II) may be used to quantify a molecule of interest. In some embodiments, a coelenterazine analogue (e.g., a native or known coelenterazine or a compound of formula (I) or formula (II)) can be used as a probe of a specific biochemical activity, e.g., apoptosis or drug metabolism.

In certain embodiments, the compounds of formula (I) or formula (II) can be used for detecting luminescence in live cells, e.g., in vivo. In some embodiments, a luciferase can be expressed in cells (as a reporter or otherwise), and the cells treated with a coelenterazine analogue (e.g., a compound of formula (I) or formula (II)), which will permeate cells in culture, react with the luciferase, and generate luminescence. In addition to being cell permeant, the compounds of formula (I) or formula (II) show comparable biocompatibility to native coelenterazine in terms of cell viability. In some embodiments, the compounds of formula (I) or formula (II) containing chemical modifications known to increase the stability of native coelenterazine in media can be synthesized and used for more robust, live cell luciferase-based reporter assays. In still other embodiments, a sample (including cells, tissues, animals, etc.) containing a luciferase and a compound of formula (I) or formula (II) may be assayed using various microscopy and imaging techniques, e.g., in vivo imaging. In still other embodiments, a secretable luciferase is expressed in cells as part of a live-cell reporter system.

In certain embodiments, the compounds of formula (I) or formula (II) disclosed herein may be provided as part of a kit. In some embodiments, the kit may include one or more luciferases (in the form of a polypeptide, a polynucleotide, or both) and a coelenterazine analogue of formula (I) or formula (II), along with suitable reagents and instructions to enable a user to perform assays such as those disclosed herein. The kit may also include one or more buffers such as those disclosed herein.

4. EXAMPLES

Example 1

Synthesis of Intermediates A, B, and C

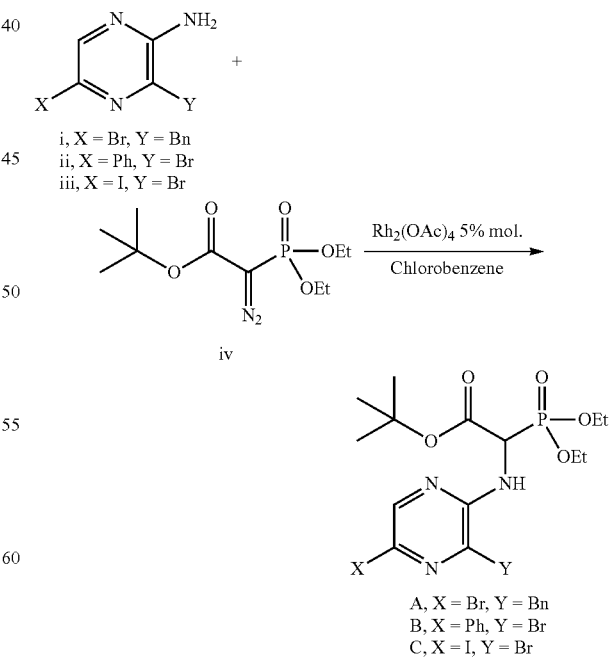

i, X = Br, Y = Bn
ii, X = Ph, Y = Br
iii, X = I, Y = Br

A, X = Br, Y = Bn
B, X = Ph, Y = Br
C, X = I, Y = Br

General procedure for the synthesis of A-C. In a 5 mL round bottom flask, aminopyrazine (i-iii, 2 mmol, 1 eq.), diazo compound (iv, 1.1 g, 4 mmol, 2 eq.), Rh$_2$(OAc)$_4$ (88.36 mg, 10 mol %), and 3 mL of chlorobenzene was placed. The reaction mixture was heated at 100° C. for 24 hours. The progress of the reaction was monitored by LCMS. After 24 hours, the reaction reached 100% conversion. The mixture was adsorbed on celite and purified on a silica column using 40% EtOAc in heptane as eluent. The desired product was isolated pure as a brown solid with a 35.5-75.6% yield. Aminopyrazine i was synthesized by adopting a procedures from WO2012040105; Kojima, S. et al., "Improved Syntheses of Watasenia Preluciferin (Coelenterazine) and Watasenia Luciferin (Coelenterazine Disulfate), and Site Specific Syntheses of the Coelenterazine Monosulfates," ITE Letters on Batteries, New Technologies & Medicine, International Battery Materials Association, Kwa-Maritane, South Africa, March, 2001, C1-C5; and Shrestha et al., "Strategies for Large-Scale Synthesis of Coelenterazine for in Vivo Applications," Synthesis 2014; 46(05): 646-652. Aminopyrazine ii was synthesized by adopting a procedure from WO/2007/096764. Aminopyrazine iii was synthesized by adopting a procedure from WO/2010/121003 using commercially available 2-amino-5-iodopyrazine (CAS No. 886860-50-0). Diazophosphonoacetate iv was synthesized according to Wang et al. *Synlett*, 2007, 11, 1683-1686.

Tert-butyl 2-((3-benzyl-5-bromopyrazin-2-yl)amino)-2-(diethoxyphosphoryl)acetate (A)

Yield: 75.6%; $^1$H NMR (300 MHz, CDCl$_3$) δ=7.99 (s, 1H), 7.33-7.14 (m, 5H), 5.19 (dd, J=5.2, 7.9, 1H), 4.96 (dd, J=8.0, 21.6, 1H), 4.17-3.76 (m, 6H), 1.39 (s, 9H), 1.26-1.08 (m, 6H). $^{13}$C NMR (75 MHz, CDCl$_3$) δ=166.1, 150.2, 142.8, 141.6, 135.5, 129.5, 128.9, 128.7, 127.1, 126.3, 126.2, 83.1, 63.4, 53.5, 40.3, 27.8, 16.3. HRMS, C$_{21}$H$_{29}$N$_3$O$_5$PBr, (m/z) [M+H] calculated: 514.1101, observed: 514.1089.

Tert-butyl 2-((3-bromo-5-phenylpyrazin-2-yl)amino)-2-(diethoxyphosphoryl)acetate (B)

Yield: 73.4%; $^1$H NMR (300 MHz, CDCl$_3$) δ=8.27 (d, J=1.7, 1H), 7.69 (dd, J=1.3, 6.8, 2H), 7.24 (ddd, J=3.6, 7.0, 15.7, 3H), 5.93-5.82 (m, 1H), 5.15-5.00 (m, 1H), 4.17-3.98 (m, 4H), 1.38 (s, 9H), 1.20 (m, 6H). $^{13}$C NMR (75 MHz, CDCl$_3$) δ=165.9, 149.0, 148.9, 142.6, 136.8, 135.2, 128.7, 128.4, 127.1, 125.5, 83.3, 63.4, 53.5, 27.7, 16.3. $^{31}$P NMR (121 MHz, CDCl$_3$) δ=16.74 (s). HRMS, C$_{20}$H$_{27}$N$_3$O$_5$PBr, (m/z) [M+H] calculated: 500.0944, observed: 500.0936.

Tert-butyl 2-((3-bromo-5-iodopyrazin-2-yl)amino)-2-(diethoxyphosphoryl)acetate (C)

Yield: 35.4%; $^1$H NMR (300 MHz, CDCl$_3$) δ=8.06 (s, 1H), 5.87 (dd, J=4.4, 8.0, 1H), 4.97 (dd, J=8.1, 21.4, 1H), 4.21-4.00 (m, 4H), 1.45-1.34 (m, 9H), 1.30-1.17 (m, 6H). $^{13}$C NMR (75 MHz, CDCl$_3$) δ=169.9, 150.4, 147.9, 142.4, 126.6, 110.4, 108, 94.8, 82.5, 53.4, 30.0, 27.9. HRMS, C$_{14}$H$_{22}$N$_3$O$_5$PBrI, (m/z) [M+H] calculated: 549.9598, observed: 549.9592.

Example 2

Synthetic Method I

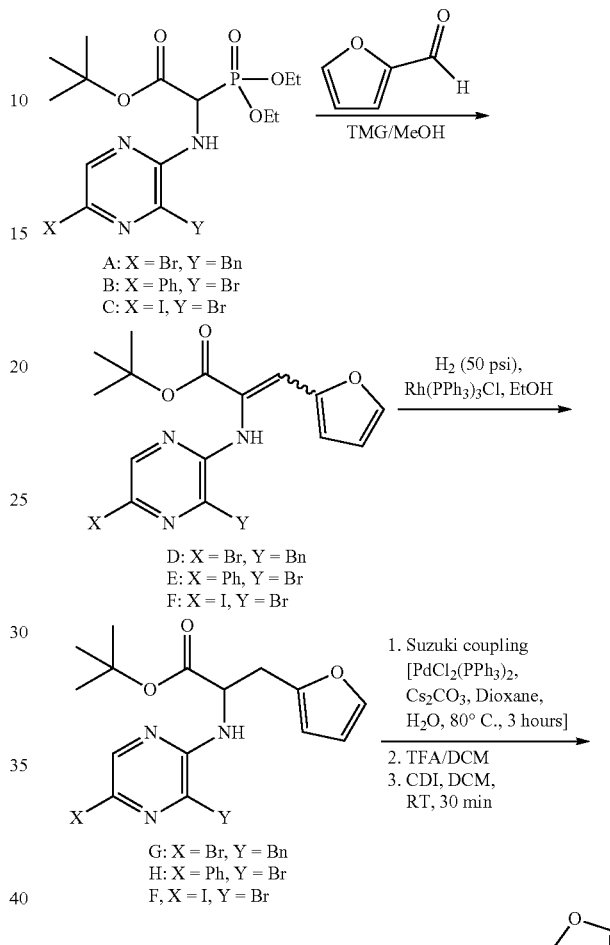

A: X = Br, Y = Bn
B: X = Ph, Y = Br
C: X = I, Y = Br

D: X = Br, Y = Bn
E: X = Ph, Y = Br
F: X = I, Y = Br

G: X = Br, Y = Bn
H: X = Ph, Y = Br
F, X = I, Y = Br

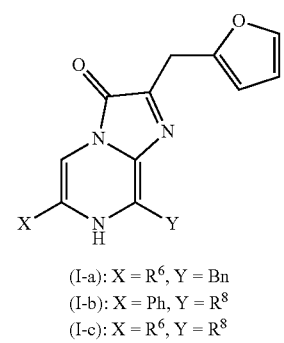

(I-a): X = R$^6$, Y = Bn
(I-b): X = Ph, Y = R$^8$
(I-c): X = R$^6$, Y = R$^8$

General procedure for method I: In a 20 mL vial, one of A-C (200 mg, 0.39 mmol, 1 eq.), 2-furaldehyde (0.43 mmol, 1.1 eq.), and 15 mL of methanol was placed. 1,1,3,3-Tetramethylguanidine (135 mg, 1.2 mmol, 3 eq.) was added, and the reaction mixture was stirred at room temperature for 1-2 hours. The progress of the reaction was monitored by LCMS. After the reaction was complete, the mixture was poured into water, extracted with ethyl acetate, and dried over MgSO$_4$. The drying agent was removed by filtration, and the solvent was concentrated under reduced pressure. The residue was purified using flash chromatography on silica gel with heptane/ethyl acetate as eluent to provide one of D-F.

In a parr-shaker reactor flask, one of D-F (0.3 mmol, 1 eq.), Rh(PPh$_3$)$_3$Cl (0.03 mmol, 0.1 eq.), and 50 mL of ethanol was placed. The reactor was charged with H$_2$ (50 psi) and shaken for 20 hours at room temperature. The reaction was monitored by LCMS. All volatiles were removed under reduced pressure, and the residue was purified by flash chromatography on silica gel using heptane/ethylacetate as eluent. The reduced aminopyrazine derivatives G-I were isolated.

Compounds with the general structure G, H, I (0.225 mmol, 1 eq.) was dissolved in dioxane (8 mL). To this solution, appropriate boronic acid, boronic acid pinacol ester or potassium trifluoroborate (0.248 mmol, 1.1 eq), Pd(PPh$_3$)$_2$Cl$_2$ (0.022 mmol, 0.1 eq.), and Cs$_2$CO$_3$ (0.675 mmol, of 1M solution, 3 eq.) were added. The reaction mixture was heated at 80° C. for 1-4 hours. The progress of the reaction was monitored by LCMS. After reaction was complete, the reaction mixture was adsorbed on celite and purified by silica gel column chromatography using Heptane/EtOAc as eluent. Fractions containing the product were collected and concentrated under reduced pressure.

The Suzuki coupling product (0.25 mmol, 1 eq.) was dissolved in dichloromethane (5 mL), and to this solution, trifluoroacetic acid (2 mL) was added. The reaction mixture was stirred at room temperature for 12 hours. The progress of the reaction was monitored by LCMS. After the reaction was complete, all volatiles were removed under reduced pressure, and the residue was co-evaporated 3 times with 10 mL of toluene to remove all TFA and provide the corresponding carboxylic acid intermediate. After drying under high vacuum, the carboxylic acid intermediate was dissolved in dichloromethane (15 mL), and to this solution, carbodiimidazole (CDI) (122 mg, 0.75 mmol, 3 eq.) was added. The reaction mixture was stirred at room temperature for 20 minutes and then poured into 0.01 M HCl (50 mL), extracted with dichloromethane, and dried over MgSO$_4$. The drying agent was removed by filtration, and the solvent was concentrated under reduced pressure. The residue was purified via flash chromatography on silica gel using dichloromethane/methanol as eluent. The corresponding coelenterazine analogue of formula (I) was isolated.

The following compounds were prepared using the general procedure of Method I and compound A as starting material to provide compounds of formula (I-a). Substitution at the R$^6$ substitution site was achieved by using the appropriate organoborane reagent for the Suzuki coupling reaction.

| compound | Structure | Yield (%) | MS [M + H] |
|---|---|---|---|
| AS-140 | 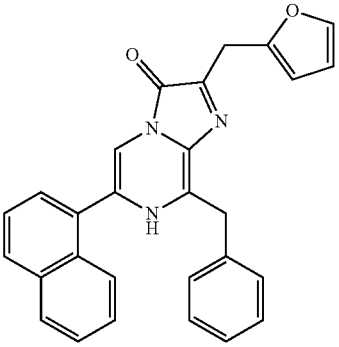 [SMILES: O=c1c(Cc2ccco2)nc2c(Cc3ccccc3)[nH]c(-c3cccc4ccccc34)cn1-2]<br>8-benzyl-2-(furan-2-ylmethyl)-6-(naphthalen-1-yl)imidazo[1,2-a]pyrazin-3(7H)-one | 8.4 | 432 |
| AS-141 | 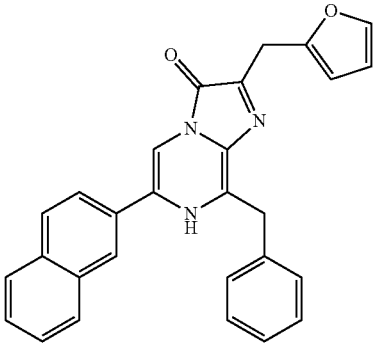 [SMILES: O=c1c(Cc2ccco2)nc2c(Cc3ccccc3)[nH]c(-c3ccc4ccccc4c3)cn1-2]<br>8-benzyl-2-(furan-2-ylmethyl)-6-(naphthalen-2-yl)imidazo[1,2-a]pyrazin-3(7H)-one | 6.5 | 432 |

-continued

| compound | Structure | Yield (%) | MS [M + H] |
|---|---|---|---|
| AS-142 | 6-(anthracen-9-yl)-8-benzyl-2-(furan-2-ylmethyl)imidazo[1,2-a]pyrazin-3(7H)-one | 17.5 | 482 |
| AS-143 | 8-benzyl-2-(furan-2-ylmethyl)-6-(phenanthren-9-yl)imidazo[1,2-a]pyrazin-3(7H)-one | 11 | 482 |
| AS-144 | 6-([1,1'-biphenyl]-4-yl)-8-benzyl-2-(furan-2-ylmethyl)imidazo[1,2-a]pyrazin-3(7H)-one | 6.7 | 458 |
| AS-154 | 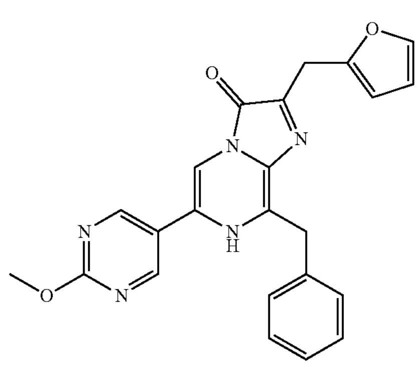 [SMILES: COc1ncc(-c2cn3c(=O)c(Cc4ccco4)nc-3c(Cc3ccccc3)[nH]2)cn1] | 18.7 | 414 |

| compound | Structure | Yield (%) | MS [M + H] |
|---|---|---|---|
8-benzyl-2-(furan-2-ylmethyl)-6-(2-methoxypyrimidin-5-yl)imidazo[1,2-a]pyrazin-3(7H)-one
AS-153
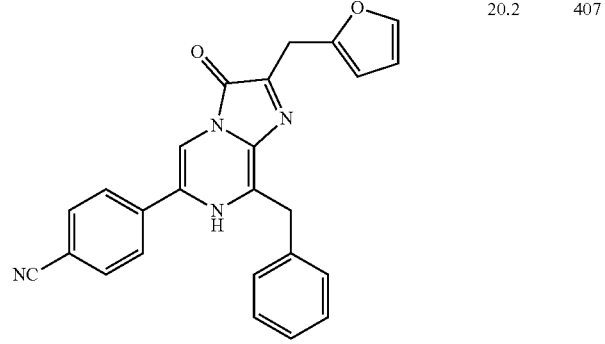
20.2    407
4-(8-benzyl-2-(furan-2-ylmethyl)-3-oxo-3,7-dihydroimidazo[1,2-a]pyrazin-6-yl)benzonitrile
AS-155
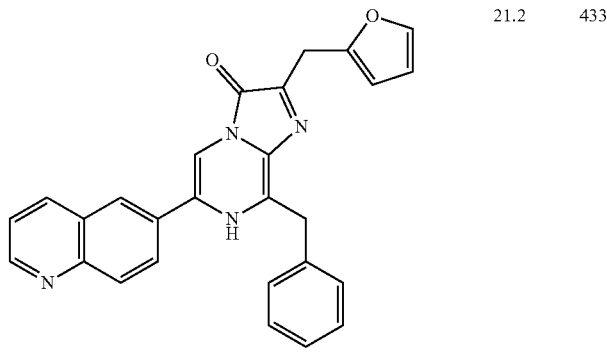
21.2    433
8-benzyl-2-(furan-2-ylmethyl)-6-yl)imidazo[1,2-a]pyrazin-3(7H)-one
JRW-0185
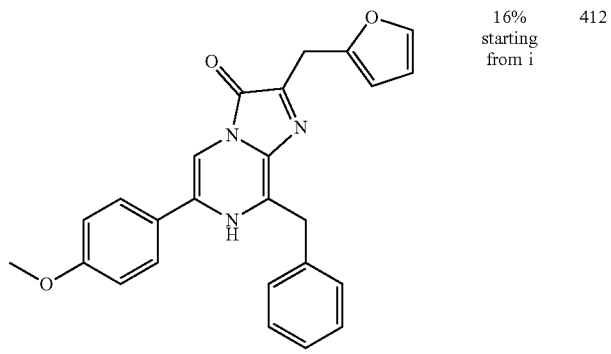
16% starting from i    412
8-benzyl-2-(furan-2-ylmethyl)-6-(4-methoxyphenyl)imidazo[1,2-a]pyrazin-3(7H)-one -continued
| compound | Structure | Yield (%) | MS [M + H] |
|---|---|---|---|
| JRW-0231 | 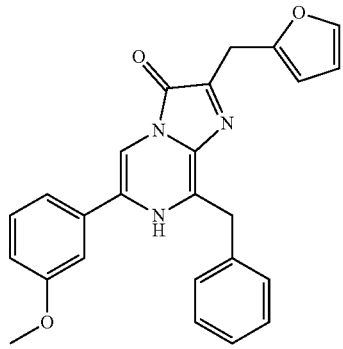 [SMILES: COc1cccc(-c2cn3c(=O)c(Cc4ccco4)nc-3c(Cc3ccccc3)[nH]2)c1] 8-benzyl-2-(furan-2-ylmethyl)-6-(3-methoxyphenyl)imidazo[1,2-a]pyrazin-3(7H)-one | 17% starting from i | 412 |
| JRW-0232 | 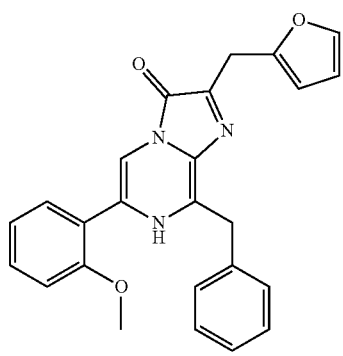 [SMILES: COc1ccccc1-c1cn2c(=O)c(Cc3ccco3)nc-2c(Cc2ccccc2)[nH]1] 8-benzyl-2-(furan-2-ylmethyl)-6-(2-methoxyphenyl)imidazo[1,2-a]pyrazin-3(7H)-one | 15% starting from i | 412 |
| JRW-0236 | 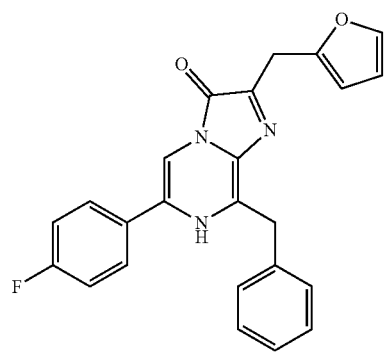 [SMILES: O=c1c(Cc2ccco2)nc2c(Cc3ccccc3)[nH]c(-c3ccc(F)cc3)cn1-2] 8-benzyl-6-(4-fluorophenyl)-2-(furan-2-ylmethyl)imidazo[1,2-a]pyrazin-3(7H)-one | 18% starting from i | 400 |

| compound | Structure | Yield (%) | MS [M + H] |
|---|---|---|---|
| JRW-0238 | 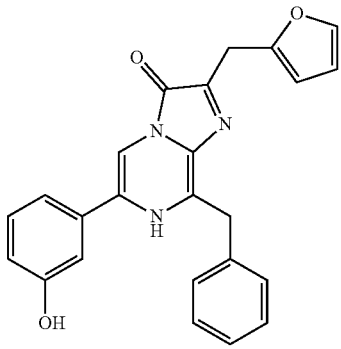 [SMILES: O=c1c(Cc2ccco2)nc2c(Cc3ccccc3)[nH]c(-c3cccc(O)c3)cn1-2] 8-benzyl-2-(furan-2-ylmethyl)-6-(3-hydroxyphenyl)imidazo[1,2-a]pyrazin-3(7H)-one | 10% starting from i | 398 |
| JRW-0446 | 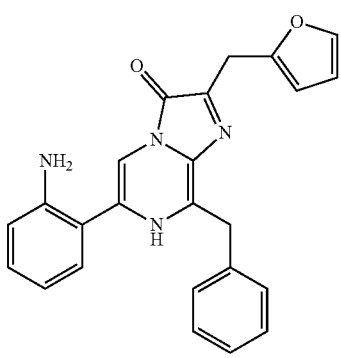 [SMILES: Nc1ccccc1-c1cn2c(=O)c(Cc3ccco3)nc-2c(Cc2ccccc2)[nH]1] 6-(2-aminophenyl)-8-benzyl-2-(furan-2-ylmethyl)imidazo[1,2-a]pyrazin-3(7H)-one | 62 | 397 |
| JRW-0438 | 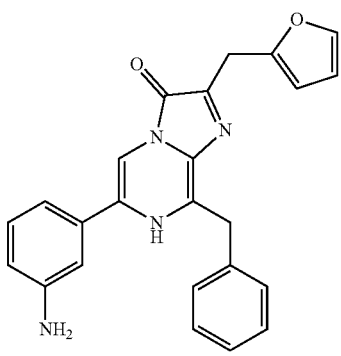 [SMILES: Nc1cccc(-c2cn3c(=O)c(Cc4ccco4)nc-3c(Cc3ccccc3)[nH]2)c1] 6-(3-aminophenyl)-8-benzyl-2-(furan-2-ylmethyl)imidazo[1,2-a]pyrazin-3(7H)-one | 14 | 397 |

-continued

| compound | Structure | Yield (%) | MS [M + H] |
|---|---|---|---|
| JRW-0445 | 6-(4-aminophenyl)-8-benzyl-2-(furan-2-ylmethyl)imidazo[1,2-a]pyrazin-3(7H)-one | 66 | 397 |

The following compounds were prepared using the general procedure of Method I and compound B as starting material to provide compounds of formula (I-b). Appropriate substitution at the $R^8$ substitution site was achieved by using the appropriate organoborane reagent for the Suzuki coupling reaction.

| compound | Structure | Yield (%) | MS [M + H] |
|---|---|---|---|
| AS-174 | 2-(furan-2-ylmethyl)-6,8-diphenylimidazo[1,2-a]pyrazin-3(7H)-one | 25 | 368 |
| JRW-0240 | 8-cyclopentyl-2-(furan-2-ylmethyl)-6-phenylimidazo[1,2-a]pyrazin-3(7H)-one | 6 starting from (3-amino-2,5-dibromopyrazine) | 359 |

-continued
| compound | Structure | Yield (%) | MS [M + H] |
|---|---|---|---|
| AS-215 | 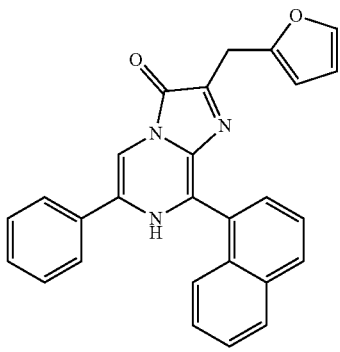 [SMILES: O=c1c(Cc2ccco2)nc2c(-c3cccc4ccccc34)[nH]c(-c3ccccc3)cn1-2]<br>2-(furan-2-ylmethyl)-8-(naphthalen-1-yl)-6-phenylimidazo[1,2-a]pyrazin-3(7H)-one | 15.6 | 418 |
| AS-216 | 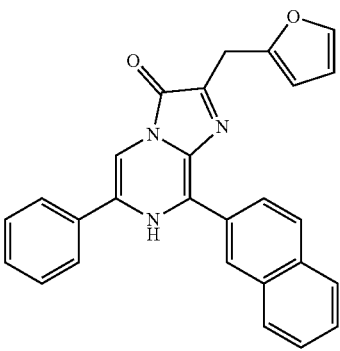 [SMILES: O=c1c(Cc2ccco2)nc2c(-c3ccc4ccccc4c3)[nH]c(-c3ccccc3)cn1-2]<br>2-(furan-2-ylmethyl)-8-(naphthalen-2-yl)-6-phenylimidazo[1,2-a]pyrazin-3(7H)-one | 14.3 | 418 |
| AS-219 | 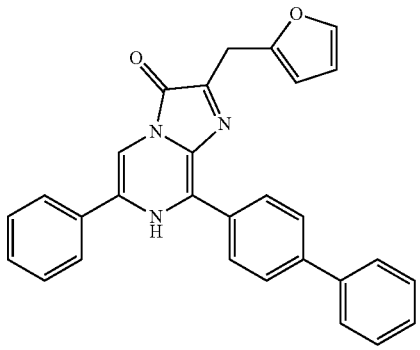 [SMILES: O=c1c(Cc2ccco2)nc2c(-c3ccc(-c4ccccc4)cc3)[nH]c(-c3ccccc3)cn1-2]<br>8-([1,1'-biphenyl]-4-yl)-2-(furan-2-ylmethyl)-6-phenylimidazo[1,2-a]pyrazin-3(7H)-one | 7.2 | 444 |

-continued

| compound | Structure | Yield (%) | MS [M + H] |
|---|---|---|---|
| AS-218 | 2-(furan-2-ylmethyl)-8-(phenanthren-9-yl)-6-phenylimidazo[1,2-a]pyrazin-3(7H)-one | 6.3 | 468 |
| AS-242 | 2-(furan-2-ylmethyl)-6-phenyl-8-(phenylethynyl)imidazo[1,2-a]pyrazin-3(7H)-one | 13.7 | 392 |
| AS-239 | (E)-2-(furan-2-ylmethyl)-6-phenyl-8-styrylimidazo[1,2-a]pyrazin-3(7H)-one | 24 | 394 |
| AS-221 | 8-(benzofuran-2-yl)-2-(furan-2-ylmethyl)-6-phenylimidazo[1,2-a]pyrazin-3(7H)-one | 23 | 408 |

| compound | Structure | Yield (%) | MS [M + H] |
|---|---|---|---|
| AS-222 | 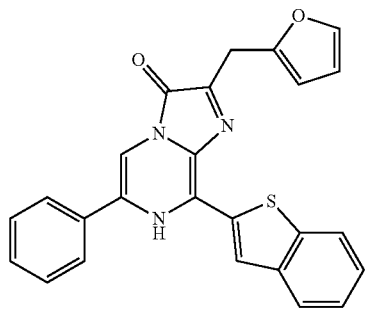 [SMILES: O=c1c(Cc2ccco2)nc2c(-c3cc4ccccc4s3)[nH]c(-c3ccccc3)cn1-2] 8-(benzo[b]thiophen-2-yl)-2-(furan-2-ylmethyl)-6-phenylimidazo[1,2-a]pyrazin-3(7H)-one | 28 | 424 |
| AS-240 | 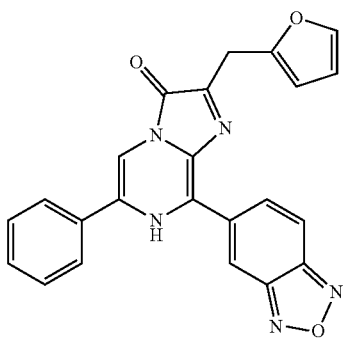 [SMILES: O=c1c(Cc2ccco2)nc2c(-c3ccc4nonc4c3)[nH]c(-c3ccccc3)cn1-2] 8-(benzo[c][1,2,5]oxadiazol-5-yl)-2-(furan-2-ylmethyl)-6-phenylimidazo[1,2-a]pyrazin-3(7H)-one | 14 | 410 |
| AS-223 | 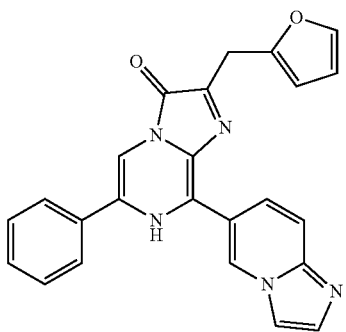 [SMILES: O=c1c(Cc2ccco2)nc2c(-c3ccc4nccn4c3)[nH]c(-c3ccccc3)cn1-2] 2-(furan-2-ylmethyl)-8-(imidazo[1,2-a]pyridin-6-yl)-6-phenylimidazo[1,2-a]pyrazin-3(7H)-one | 16 | 408 |

-continued
| compound | Structure | Yield (%) | MS [M + H] |
|---|---|---|---|
| AS-227 | 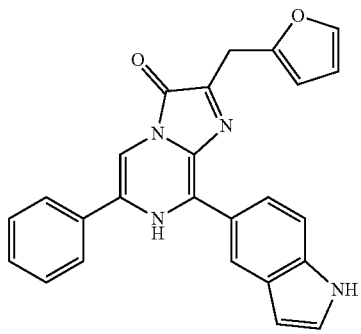 [SMILES: O=c1c(Cc2ccco2)nc2c(-c3ccc4[nH]ccc4c3)[nH]c(-c3ccccc3)cn1-2] 2-(furan-2-ylmethyl)-8-(1H-indol-5-yl)-6-phenylimidazo[1,2-a]pyrazin-3(7H)-one | 32 | 407 |
| AS-250 | 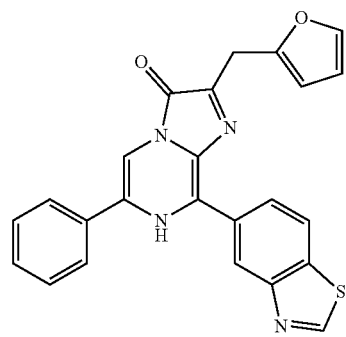 [SMILES: O=c1c(Cc2ccco2)nc2c(-c3ccc4scnc4c3)[nH]c(-c3ccccc3)cn1-2] 8-(benzo[d]thiazol-5-yl)-2-(furan-2-ylmethyl)-6-phenylimidazo[1,2-a]pyrazin-3(7H)-one | 31 | 425 |
| AS-243 | 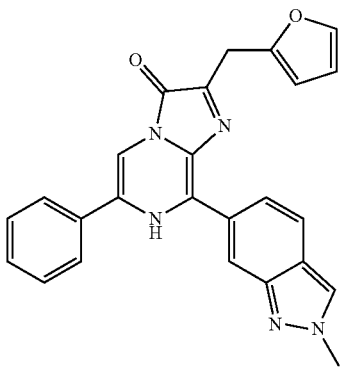 [SMILES: Cn1cc2ccc(-c3[nH]c(-c4ccccc4)cn4c(=O)c(Cc5ccco5)nc3-4)cc2n1] 2-(furan-2-ylmethyl)-8-(2-methyl-2H-indazol-6-yl)-6-phenylimidazo[1,2-a]pyrazin-3(7H)-one | 23 | 422 |

-continued
| compound | Structure | Yield (%) | MS [M + H] |
|---|---|---|---|
| AS-245 | 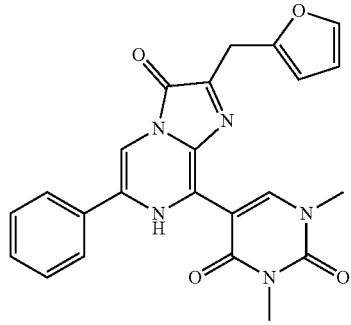 [SMILES: Cn1cc(-c2[nH]c(-c3ccccc3)cn3c(=O)c(Cc4ccco4)nc2-3)c(=O)n(C)c1=O] 5-(2-(furan-2-ylmethyl)-3-oxo-6-phenyl-3,7-dihydroimidazo[1,2-a]pyrazin-8-yl)-1,3-dimethylpyrimidine-2,4(1H,3H)-dione | 20 | 430 |
| AS-258 | 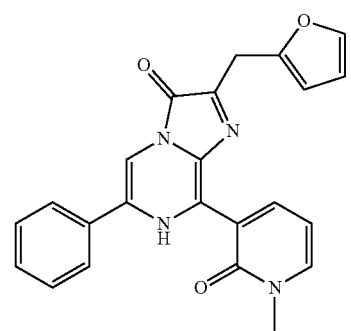 [SMILES: Cn1cccc(-c2[nH]c(-c3ccccc3)cn3c(=O)c(Cc4ccco4)nc2-3)c1=O] 2-(furan-2-ylmethyl)-8-(1-methyl-2-oxo-1,2-dihydropyridin-3-yl)-6-phenylimidazo[1,2-a]pyrazin-3(7H)-one | 25 | 399 |
| AS-256 | 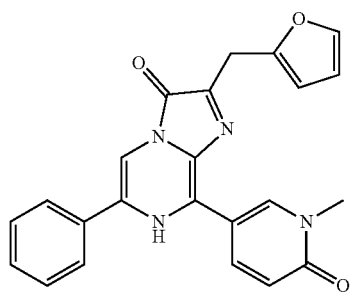 [SMILES: Cn1cc(-c2[nH]c(-c3ccccc3)cn3c(=O)c(Cc4ccco4)nc2-3)ccc1=O] 2-(furan-2-ylmethyl)-8-(1-methyl-6-oxo-1,6-dihydropyridin-3-yl)-6-phenylimidazo[1,2-a]pyrazin-3(7H)-one | 7 | 399 |

-continued

| compound | Structure | Yield (%) | MS [M + H] |
|---|---|---|---|
| AS-270 | 2-(furan-2-ylmethyl)-6-phenyl-8-(3,4,5-trifluorophenyl)imidazo[1,2-a]pyrazin-3(7H)-one | 20 | 422 |
| AS-269 | 8-(4-fluorophenyl)-2-(furan-2-ylmethyl)-6-phenylimidazo[1,2-a]pyrazin-3(7H)-one | 31 | 386 |
| AS-238 | 2-(furan-2-ylmethyl)-8-(4-nitrophenyl)-6-phenylimidazo[1,2-a]pyrazin-3(7H)-one | 16 | 413 |
| AS-237 | 4-(2-(furan-2-ylmethyl)-3-oxo-6-phenyl-3,7-dihydroimidazo[1,2-a]pyrazin-8-yl)benzonitrile | 13 | 393 |

-continued

| compound | Structure | Yield (%) | MS [M + H] |
|---|---|---|---|
| AS-274 | 3-(2-(furan-2-ylmethyl)-3-oxo-6-phenyl-3,7-dihydroimidazo[1,2-a]pyrazin-8-yl)benzonitrile | 21 | 393 |
| AS-224 | 8-(4-(dimethylamino)phenyl)-2-(furan-2-ylmethyl)-6-phenylimidazo[1,2-a]pyrazin-3(7H)-one | 5 | 411 |
| AS-229 | 2-(furan-2-ylmethyl)-6-phenyl-8-(thiophen-3-yl)imidazo[1,2-a]pyrazin-3(7H)-one | 15 | 374 |
| AS-236 | 2-(furan-2-ylmethyl)-6-phenyl-8-(thiophen-2-yl)imidazo[1,2-a]pyrazin-3(7H)-one | 20 | 374 |

-continued

| compound | Structure | Yield (%) | MS [M + H] |
|---|---|---|---|
| AS-262 | 5-(2-(furan-2-ylmethyl)-3-oxo-6-phenyl-3,7-dihydroimidazo[1,2-a]pyrazin-8-yl)thiophene-2-carbonitrile | 15 | 399 |
| AS-280 | 8-(5-chlorothiophen-2-yl)-2-(furan-2-ylmethyl)-6-phenylimidazo[1,2-a]pyrazin-3(7H)-one | 12 | 408 |
| AS-282 | 8-(3-chlorothiophen-2-yl)-2-(furan-2-ylmethyl)-6-phenylimidazo[1,2-a]pyrazin-3(7H)-one | 14 | 408 |
| AS-277 | 2-(furan-2-ylmethyl)-6-phenyl-8-(pyridin-3-yl)imidazo[1,2-a]pyrazin-3(7H)-one | 34 | 369 |

-continued

| compound | Structure | Yield (%) | MS [M + H] |
|---|---|---|---|
| AS-273 | 8-(6-fluoropyridin-3-yl)-2-(furan-2-ylmethyl)-6-phenylimidazo[1,2-a]pyrazin-3(7H)-one | 23 | 387 |
| AS-272 | 8-(2-fluoropyridin-3-yl)-2-(furan-2-ylmethyl)-6-phenylimidazo[1,2-a]pyrazin-3(7H)-one | 38 | 387 |
| AS-278 | 8-(2-chloropyridin-3-yl)-2-(furan-2-ylmethyl)-6-phenylimidazo[1,2-a]pyrazin-3(7H)-one | 5 | 403 |
| AS-276 | 2-(furan-2-ylmethyl)-6-phenyl-8-(pyridin-4-yl)imidazo[1,2-a]pyrazin-3(7H)-one | 16 | 369 |

-continued

| compound | Structure | Yield (%) | MS [M + H] |
|---|---|---|---|
| AS-271 | 8-(2-fluoropyridin-4-yl)-2-(furan-2-ylmethyl)-6-phenylimidazo[1,2-a]pyrazin-3(7H)-one | 20 | 387 |
| AS-275 | 8-(2-chloropyridin-4-yl)-2-(furan-2-ylmethyl)-6-phenylimidazo[1,2-a]pyrazin-3(7H)-one | 22 | 403 |
| AS-310 | 2-(furan-2-ylmethyl)-6-phenyl-8-(quinolin-4-yl)imidazo[1,2-a]pyrazin-3(7H)-one | 17 | 419 |
| AS-313 | 8-(2,6-dichloropyridin-4-yl)-2-(furan-2-ylmethyl)-6-phenylimidazo[1,2-a]pyrazin-3(7H)-one | 14 | 438 |

| compound | Structure | Yield (%) | MS [M + H] |
|---|---|---|---|
| AS-315 | 2-(furan-2-ylmethyl)-6-phenyl-8-(2-(trifluoromethyl)pyridin-4-yl)imidazo[1,2-a]pyrazin-3(7H)-one | 13 | 437 |
| AS-314 | 8-(2-bromopyridin-4-yl)-2-(furan-2-ylmethyl)-6-phenylimidazo[1,2-a]pyrazin-3(7H)-one | 4 | 447 |
| AS-343 | 2-(furan-2-ylmethyl)-6-phenyl-8-(thiazol-5-yl)imidazo[1,2-a]pyrazin-3(7H)-one | 16 | 375 |
| AS-311 | 5-(2-(furan-2-ylmethyl)-3-oxo-6-phenyl-3,7-dihydroimidazo[1,2-a]pyrazin-8-yl)-1-methyl-1H-pyrrole-2-carbonitrile | 13 | 396 |

The following compounds were prepared using the general procedure of Method I and compound C as starting material to provide compounds of formula (I-c). Appropriate substitution at the $R^6$ and $R^8$ substitution sites were achieved by using the appropriate organoborane reagents for the Suzuki coupling reactions.

| compound | Structure | Yield (%) | MS [M + H] |
|---|---|---|---|
| AS-175 | 6,8-di(furan-2-yl)-2-(furan-2-ylmethyl)imidazo[1,2-a]pyrazin-3(7H)-one | 23 | 348 |
| AS-176 | 2-(furan-2-ylmethyl)-6,8-di(thiophen-2-yl)imidazo[1,2-a]pyrazin-3(7H)-one | 24 | 380 |
| AS-190 | 2-(furan-2-ylmethyl)-6-(1-methyl-1H-pyrazol-3-yl)-8-(1-methyl-1H-pyrazol-4-yl)imidazo[1,2-a]pyrazin-3(7H)-one | 15 | 376 |
| AS-306 | 8-(2-fluoropyridin-4-yl)-2-(furan-2-ylmethyl)-6-(thiophen-2-yl)imidazo[1,2-a]pyrazin-3(7H)-one | 4 | 393 |

| compound | Structure | Yield (%) | MS [M + H] |
|---|---|---|---|
| AS-287 | 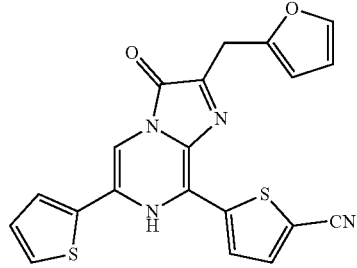 [SMILES: N#Cc1ccc(-c2[nH]c(-c3cccs3)cn3c(=O)c(Cc4ccco4)nc2-3)s1]<br>5-(2-(furan-2-ylmethyl)-3-oxo-6-(thiophen-2-yl)-3,7-dihydroimidazo[1,2-a]pyrazin-8-yl)thiophene-2-carbonitrile | 8 | 405 |
| AS-295 | 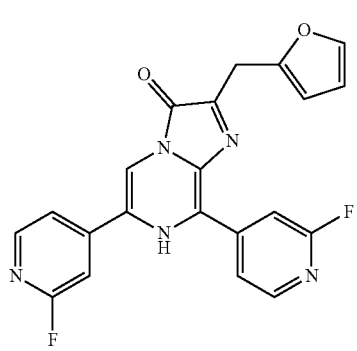 [SMILES: O=c1c(Cc2ccco2)nc2c(-c3ccnc(F)c3)[nH]c(-c3ccnc(F)c3)cn1-2]<br>26,8-bis(2-fluoropyridin-4-yl)-2-(furan-2-ylmethyl)imidazo[1,2-a]pyrazin-3(7H)-one | 13 | 406 |
| AS-333 | 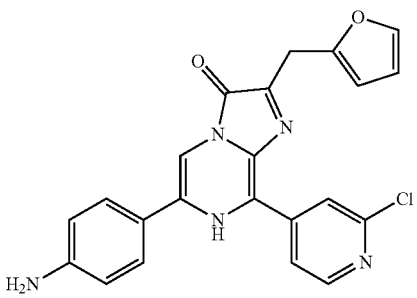 [SMILES: Nc1ccc(-c2cn3c(=O)c(Cc4ccco4)nc-3c(-c3ccnc(Cl)c3)[nH]2)cc1]<br>2-(furan-2-ylmethyl)-6-phenyl-8-(phenylethynyl)imidazo[1,2-a]pyrazin-3(7H)-one | 7.9 | 418 |
| AS-330 | 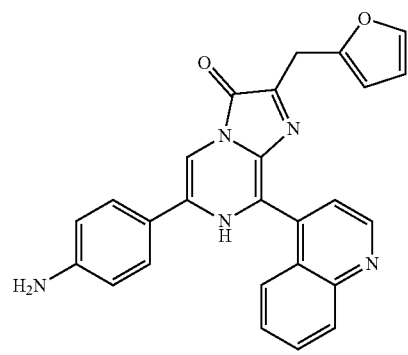 [SMILES: Nc1ccc(-c2cn3c(=O)c(Cc4ccco4)nc-3c(-c3ccnc4ccccc34)[nH]2)cc1]<br>6-(4-aminophenyl)-2-(furan-2-ylmethyl)-8-(quinolin-4-yl)imidazo[1,2-a]pyrazin-3(7H)-one | 3.4 | 434 |

-continued

| compound | Structure | Yield (%) | MS [M + H] |
|---|---|---|---|
| AS-332 | 5-(6-(4-aminophenyl)-2-(furan-2-ylmethyl)-3-oxo-3,7-dihydroimidazo[1,2-a]pyrazin-8-yl)thiophene-2-carbonitrile | 6.6 | 414 |
| AS-337 | 6,8-bis(4-aminophenyl)-2-(furan-2-ylmethyl)imidazo[1,2-a]pyrazin-3(7H)-one | 26.5 | 398 |
| AS-360 | 2-(furan-2-ylmethyl)-6-(4-hydroxyphenyl)-8-(quinolin-4-yl)imidazo[1,2-a]pyrazin-3(7H)-one | 8.8 | 435 |
| AS-353 | 5-(2-(furan-2-ylmethyl)-6-(4-hydroxyphenyl)-3-oxo-3,7-dihydroimidazo[1,2-a]pyrazin-8-yl)thiophene-2-carbonitrile | 6.9 | 415 |

During preparation of compounds AS-140, AS-141, AS-142, AS-143, AS-144, AS-154, AS-153, AS-155, AS-174, AS-215, AS-216, AS-219, AS-218, AS-242, AS-239, AS-221, AS-222, AS-240, AS-223, AS-227, AS-250, AS-243, AS-245, AS-238, AS-237, AS-224, AS-236, AS-175, AS-176, AS-190, AS-248, AS-333, AS-330, AS-332, AS-337, JRW-0446, JRW-0438, and JRW-0445, deprotection of the t-Bu ester group was performed with TFA before the Suzuki Coupling reaction. The yield for these compounds was calculated for the two-step process starting from the deprotected acid.

During preparation of compounds AS-258, AS-256, AS-270, AS-269, AS-274, AS-262, AS-280, AS-282, AS-277, AS-273, AS-272, AS-278, AS-276, AS-271, AS-275, AS-310, AS-313, AS-315, AS-314, AS-343, AS-311, AS-329, AS-321, AS-320, AS-319, AS-301, AS-292, AS-293, AS-342, AS-340, and AS-341, deprotection of the t-Bu ester group was performed with TFA after the Suzuki Coupling reaction. The yield for these compounds was calculated for the two-step process starting from the corresponding t-Bu ester.

Compounds AS-174, AS-175, AS-176, and AS-190 were prepared from the below dibromide derivative using the disclosed synthetic methodology. TFA treatment and t-Bu group deprotection was carried out before the Suzuki coupling reaction.

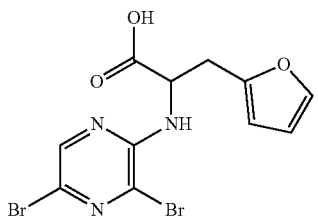 [SMILES: O=C(O)C(Cc1ccco1)Nc1ncc(Cl)nc1Br]

Compounds AS-306, AS-287, and AS-295 were prepared from the below dihalogenated derivative using the disclosed synthetic methodology. TFA treatment and t-Bu group deprotection was carried out before the Suzuki coupling reaction.

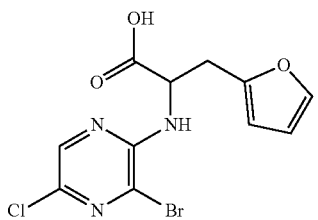

Example 3

Synthetic Method II

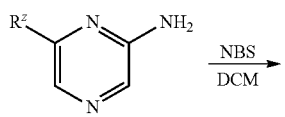

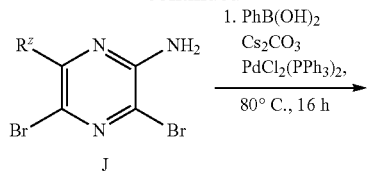

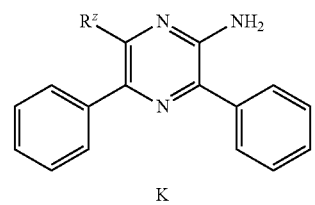

Synthetic procedure for the preparation of compound (J): 3,5-dibromo-6-chloropyrazin-2-amine ($R^z$=Cl) was prepared according to Organic Letters, 17(15), 3888-3891; 2015. 6-amino-3,5-dibromopyrazine-2-carbonitrile ($R^z$=CN) was prepared as follows. 6-Aminopyrazine-2-carbonitrile (1 g, 8.3 mmol) was dissolved in dichloromethane (15 mL). To this solution, NBS (2.96 g, 16.65 mmol, 2 eq.) was added, and the reaction mixture was stirred at room temperature overnight (16 h). The reaction mixture was poured into water and extracted with dichloromethane, dried over $MgSO_4$, filtered, and concentrated under reduced pressure. The residue was purified using silica gel chromatography with Heptane/EtOAc as eluent providing 6-amino-3,5-dibromopyrazine-2-carbonitrile ($R^z$=CN).

Synthetic procedure for the preparation of 6-chloro-3,5-diphenylpyrazin-2-amine (K): 3,5-dibromo-6-chloropyrazin-2-amine (5 g, 17.4 mmol) was dissolved in dioxane (50 mL). To this solution, $Pd(PPh_3)_3Cl_2$ (610 mg, 0.87 mmol), phenyl boronic acid (2.33 g, 19.1 mmol), and 1 M solution of $Cs_2CO_3$ (52 mL, 3 eq.) were added. The reaction mixture was stirred for 4 h at 80° C., then poured into water, and extracted with EtOAc. Organic fractions were collected, dried over $MgSO_4$, filtered, and concentrated under reduced pressure. The residue was loaded on celite, and the product was purified using silica gel chromatography with Heptane/EtOAc as eluent. Isolated 4.15 g, 85%.

Synthetic procedure for the preparation of 6-amino-3,5-diphenylpyrazine-2-carbonitrile (K): 6-Amino-3,5-dibromopyrazine-2-carbonitrile (200 mg, 0.72 mmol) was dissolved in dioxane (10 mL). To this solution, $Pd(PPh_3)_3Cl_2$ (50 mg, 0.071 mmol), phenyl boronic acid (175 mg, 1.44 mmol), and 1M solution of $Cs_2CO_3$ (2.16 mL, 3 eq.) were added. The reaction mixture was stirred for 4 h at 80° C. then poured into water and extracted with EtOAc. Organic fractions were collected, dried over $MgSO_4$, filtered, and concentrated under reduced pressure. The residue was loaded on celite, and the product was purified using silica gel chromatography with Heptane/EtOAc as eluent providing 6-amino-3,5-diphenylpyrazine-2-carbonitrile, 120 mg, 60%.

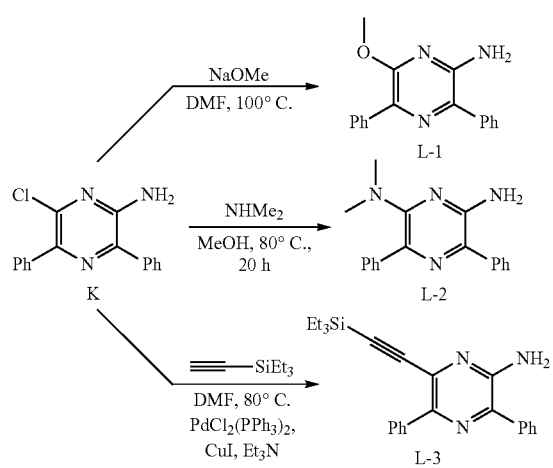

Synthetic procedure for the preparation of 6-methoxy-3,5-diphenylpyrazin-2-amine (L-1): 6-Chloro-3,5-diphenylpyrazin-2-amine (200 mg, 0.7 mmol) was dissolved in 5 mL of DMF. NaOMe (383 mg, 7 mmol, 10 eq.) was added to this solution, and the reaction mixture was heated at 100° C. for 16 h. The reaction mixture was poured into water and extracted with EtOAc. Organic fractions were collected, dried over MgSO$_4$, filtered, and concentrated under reduced pressure. The residue was loaded on celite, and the product was purified using silica gel chromatography with Heptane/EtOAc as eluent. 6-Methoxy-3,5-diphenylpyrazin-2-amine was isolated as a white solid, 70 mg, 35.6%.

Synthetic procedure for the preparation of N2,N2-dimethyl-3,5-diphenylpyrazine-2,6-diamine (L-2): 6-Chloro-3,5-diphenylpyrazin-2-amine (200 mg, 0.7 mmol) was dissolved in 10.65 mL of 2M methanol solution of diethylamine. The reaction mixture was heated at 80° C. for 16 h then poured into water and extracted with EtOAc. Organic fractions were collected, dried over MgSO$_4$, filtered, and concentrated under reduced pressure. The residue was loaded on celite, and the product was purified using silica gel chromatography with Heptane/EtOAc as eluent. 6-N2,N2-dimethyl-3,5-diphenylpyrazine-2,6-diamine was isolated pure as a pale yellow solid, 130 mg, 63%.

Synthetic procedure for the preparation of 3,5-diphenyl-6-((triethylsilyl)ethynyl)pyrazin-2-amine (L-3): 6-Chloro-3,5-diphenylpyrazin-2-amine (500 mg, 1.7 mmol) was dissolved in DMF (10 mL). To this solution, Pd(PPh$_3$)$_3$Cl$_2$ (154 mg, 0.177 mmol 0.1 eq.), CuI (67 mg, 0.35 mmol, 0.2 eq.), triethyl(ethynyl)silane (497 mg, 3.55 mmol), and triethylamine (538 mg, 5.32 mmol, 3 eq.) were added. The reaction mixture was stirred for 4 h at 80° C., then poured into water and extracted with EtOAc. Organic fractions were collected, dried over MgSO$_4$, filtered, and concentrated under reduced pressure. The residue was loaded on celite, and the product was purified using silica gel chromatography with Heptane/EtOAc as eluent. 3,5-Diphenyl-6-((triethyl silyl)ethynyl)pyrazin-2-amine was isolated pure, 534 mg, 78%.

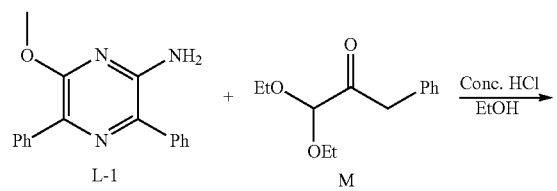

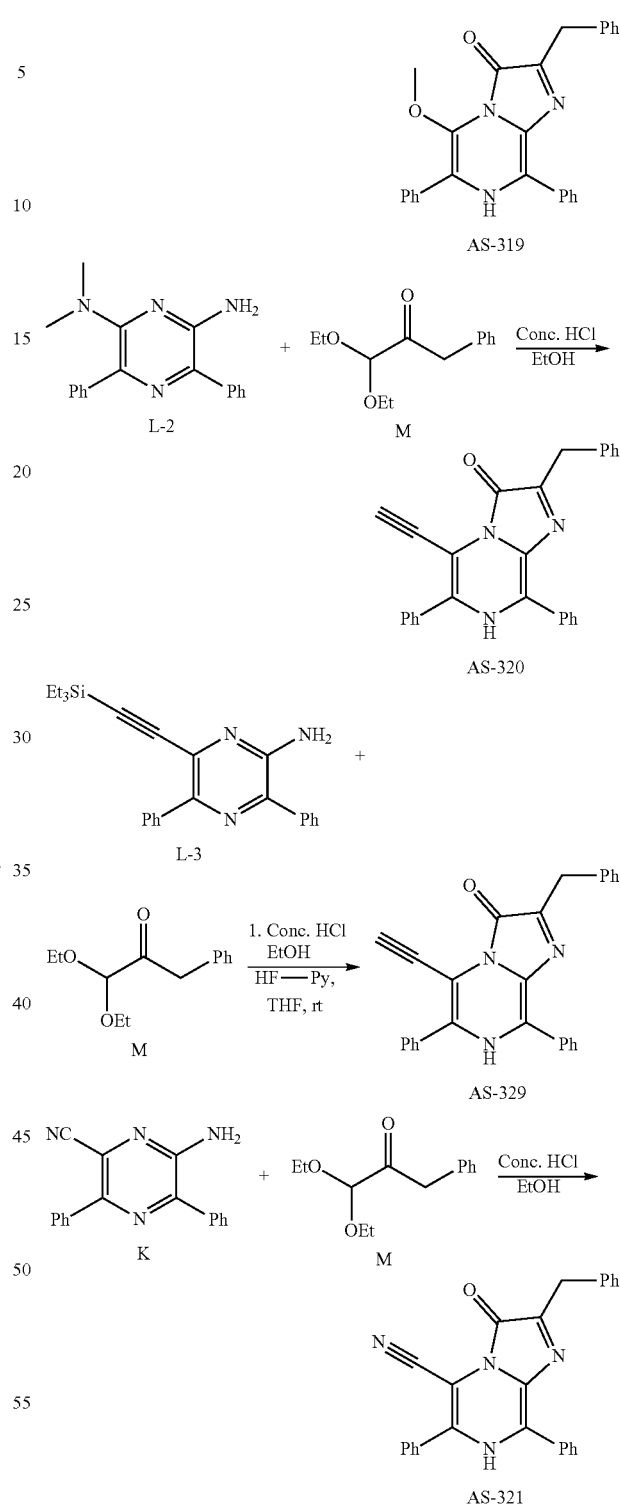

General procedure for the preparation of the coelenterazine analogues AS-329, AS-321, AS-320 and AS-319: Adopted from Bioorganic & Medicinal Chemistry Letters, 11(17), 2305-2309; 2001. 1,1-Diethoxy-3-phenylpropan-2-one (160 mg, 0.72 mmol, 2 eq.) and corresponding aminopyrazine (0.36 mmol, 1 eq.) were dissolved in ethanol (2 mL) and water (0.2 mL). To this solution, conc. HCl (0.1 mL) was added, and the mixture was heated at 80° C. until reaction reached maximum conversion. The progress of the reaction was monitored by LCMS. After the reaction reached maximum conversion, it was poured into water and extracted with EtOAc. Organic fractions were collected, dried over $MgSO_4$, filtered, and concentrated under reduced pressure. The target compound was purified using silica gel chromatography with Heptane/EtOAc as eluent.

The following compounds were prepared using the general procedure of Method II to provide compounds of formula (I-d) and formula (II). Appropriate substitution at the $R^5$ substitution site was achieved by using an appropriate reagent for substitution or Pd-catalyzed coupling, and appropriate substitution at the $R^6$ and $R^8$ substitution sites were achieved by using the appropriate organoborane reagents for the Suzuki coupling reactions.

| compound | Structure | Yield (%) | MS [M + H] |
|---|---|---|---|
| AS-248 | 2-(furan-2-ylmethyl)-5,6,8-triphenylimidazo[1,2-a]pyrazin-3(7H)-one | 14 | 444 |
| AS-329 | 2-benzyl-5-ethynyl-6,8-diphenylimidazo[1,2-a]pyrazin-3(7H)-one | 2 From aminopyrazine | 402 |
| AS-321 | 2-benzyl-3-oxo-6,8-diphenyl-3,7-dihydroimidazo[1,2-a]pyrazine-5-carbonitrile | 3.6 From aminopyrazine | 403 |
| AS-320 | 2-benzyl-5-(dimethylamino)-6,8-diphenylimidazo[1,2-a]pyrazin-3(7H)-one | 2.5 From aminopyrazine | 421 |

-continued

| compound | Structure | Yield (%) | MS [M + H] |
|---|---|---|---|
| AS-319 | 2-benzyl-5-methoxy-6,8-diphenylimidazo[1,2-a]pyrazin-3(7H)-one | 2.9 From aminopyrazine | 408 |
| AS-301 | 8-(2-fluoropyridin-4-yl)-2-(furan-2-ylmethyl)-3-oxo-6-phenyl-3,7-dihydroimidazo[1,2-a]pyrazine-5-carbonitrile | 7 | 412 |

In the case of AS-329: Prepared coelenterazine analogue was further dissolved in THF (3 mL) and treated with HF-Py reagent (1 mL) to remove the triethylsilyl protecting group. After the reaction was complete, the desired compound was purified using reverse phase chromatography with H$_2$O/CH$_3$CN as eluent.

During the preparation of AS-301, the procedure from Wang et al. (Wang, B., Zhao, R., Chen, B. C. and Balasubramanian, B., 2010. Palladium acetate catalyzed cyanation of aryl halides using Buchwald's 2-(di-t-butylphosphino)-1,1'-binaphthyl. *ARKIVOC*, 6, pp. 47-52, 2010) was adopted.

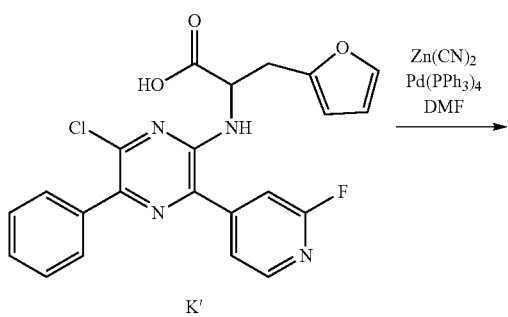

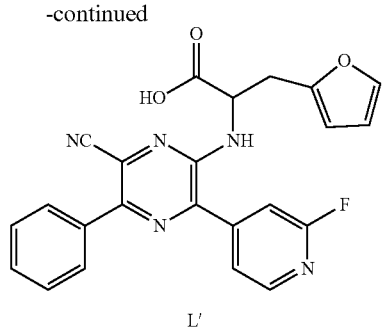

L'

The mixture of staring material K' (100 mg, 227 mmol), Zn(CN)$_2$, and Pd(PPh$_3$)$_4$ was dissolved in DMF (5 mL). The reaction mixture was heated at 110° C. for 12 h, poured into water, and extracted with EtOAc. Organic fractions were collected, dried over MgSO$_4$, filtered, and concentrated under reduced pressure. The residue was loaded on celite, and the product was purified using silica gel chromatography with DCM/MeOH as eluent, providing the target nitrile.

Compound AS-248 was prepared from aminopyrazine K (R$^z$═Cl) (Scheme above) using general Method I.

Compound AS-301 was prepared using general Method I from aminopyrazine:

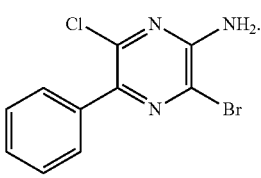 [SMILES: Nc1nc(Cl)c(-c2ccccc2)nc1Br]

Example 4

Synthetic Method III

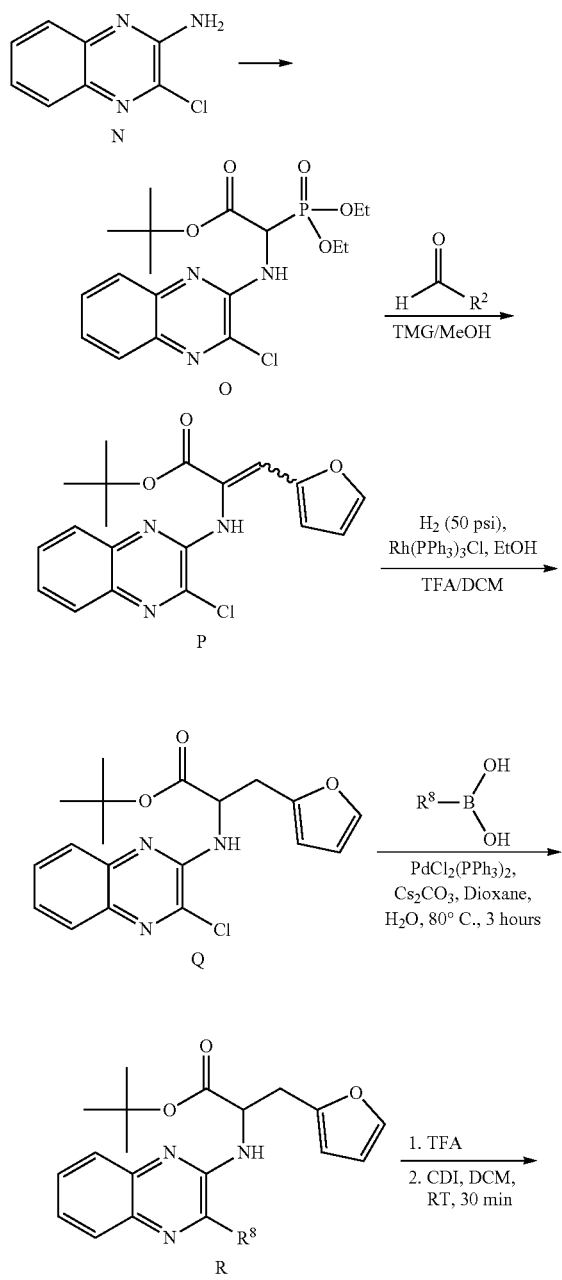

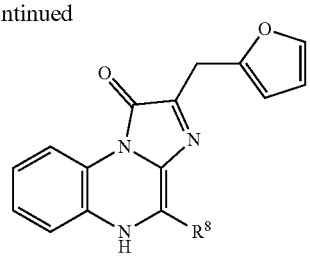

(I-e)

Synthetic procedure for the preparation of (O): In a 5 mL round bottom flask, aminopyrazine (250 mg, 1.3 mmol, 1 eq.), diazo compound (968 mg, 3.48 mmol, 2.5 eq.), $Rh_2(OAc)_4$ (61.52 mg, 0.139 mmol 10 mol %), and 3 mL of chlorobenzene were placed. The reaction mixture was heated at 100° C. for 24 hours. The progress of the reaction was monitored by LCMS. After 24 hours, the reaction reached 100% conversion. The mixture was adsorbed on celite and purified on silica column using 40% EtOAc in Heptane as eluent. Yield, 469 mg, 78.4%.

Synthetic procedure for the preparation of (P): In a 20 mL vial, compound O (469 mg, 1.09 mmol, 1 eq.), furancarbaldehyde (115.6 mg, 1.2 mmol, 1.1 eq.), and 20 mL of methanol was placed. To that solution, 1,1,3,3-tetramethylguanidine (251 mg, 2.19 mmol, 2 eq.) was added, and the reaction mixture was stirred at room temperature for 1 hour. The progress of the reaction was monitored by LCMS. After the reaction was complete, the mixture was poured into water, extracted with ethyl acetate, and dried over $MgSO_4$. The drying agent was filtered off, and the solvent was concentrated under reduced pressure. The residue was purified using flash chromatography on silica gel with heptane/ethyl acetate (70/30) as eluent. Isolated 340 mg, Yield 83.6%.

Synthetic procedure for the preparation of (Q): In a parr-shaker reactor flask, compound P (340 mg, 0.91 mmol, 1 eq.), $Rh(PPh_3)_3Cl$ (84 mg, 0.091 mmol, 0.1 eq.), and 30 mL of ethanol was placed. The reactor was charged with $H_2$ (50 psi) and shook for 20 hours at room temperature. The reaction was monitored by LCMS, then all volatiles were removed under reduced pressure, and the residue was subjected to flash chromatography on silica gel using heptane/ethyl acetate as eluent (70/30). Yield 16 mg, 47%.

Synthetic procedure for the preparation of formula (I-e): Compound Q (77.5 mg, 0.207 mmol, 1 eq.) was dissolved in dioxane (6 mL). To this solution, appropriate boronic acid, boronic acid pinacol ester or potassium trifluoroborate (0.228 mmol, 1.1 eq), $Pd(PPh_3)_2Cl_2$ (14.5 mg, 0.022 mmol, 0.1 eq.), and $Cs_2CO_3$ (0.675 mmol, of 1M solution, 3 eq.) were added. The reaction mixture was heated at 80° C. for 4 hours. The progress of the reaction was monitored by LCMS. After the reaction was complete, the reaction mixture was adsorbed on celite and purified by silica gel column chromatography using Heptane/EtOAc as eluent. Fractions containing the product were concentrated under reduced pressure and redissolved in 2 mL of dichloromethane. To this solution, 2 mL of TFA was added, and the reaction mixture was stirred at room temperature for several hours (6-12 h.). The progress of the reaction was monitored by LCMS. After the reaction reached maximum conversion, all volatiles were removed under reduced pressure, and the residue was co-evaporated with toluene (2 times ×30 mL) to remove the traces of TFA. The crude product was redissolved in dichloromethane (15 mL). Carbonyldiimidazole (100.9 mg, 0.622 mmol, 3 eq.) was added to the DCM solution and the reaction mixture was stirred at room temperature for 30 minutes. The reaction mixture was poured into a 0.1 M solution of hydrochloric acid (100 mL). Organic fractions were extracted with dichloromethane, dried over MgSO$_4$, filtered, and concentrated under reduced pressure. The residue was loaded onto a silica gel column and purified using dichloromethane/methanol as eluent providing the desired compound.

The following compounds were prepared using the general procedure of Method III to provide compounds of formula (I-e). Appropriate substitution at the R$^8$ substitution site was achieved by using the appropriate organoborane reagent for the Suzuki coupling reactions.

| compound | Structure | Yield (%) | MS [M + H] |
|---|---|---|---|
| AS-292 | 4-(2-chloropyridin-4-yl)-2-(furan-2-ylmethyl)imidazo[1,2-a]quinoxalin-1(5H)-one | 16 | 377 |
| AS-293 | 5-(2-(furan-2-ylmethyl)-1-oxo-1,5-dihydroimidazo[1,2-a]quinoxalin-4-yl)thiophene-2-carbonitrile | 18 | 373 |

Example 5

Synthetic Method IV

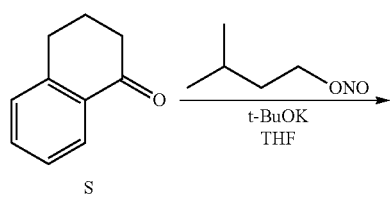

S

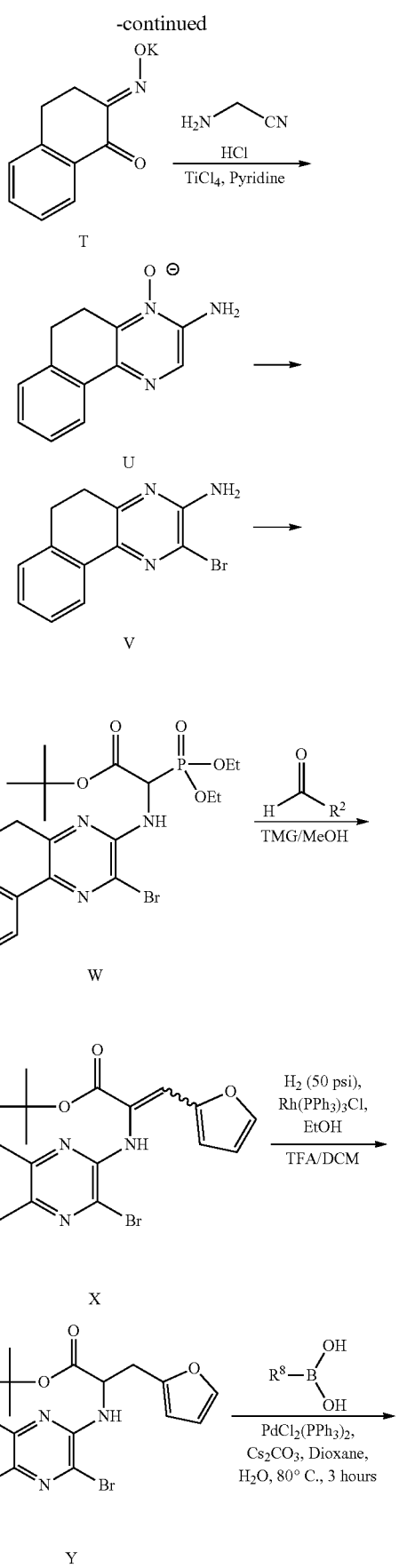

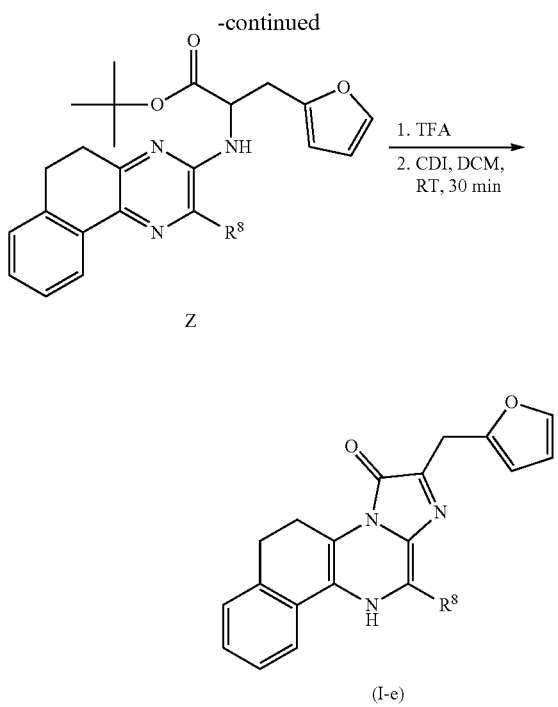

Synthetic procedure for the preparation of (T): Performed according to the WO 2014/145512 (PCT/US2014/030300). To a suspension of potassium tert-butanolate (23 g, 205 mmol, 1.2 eq.) in dry ethyl ether (500 mL) at 0° C., 3,4-dihydronaphthalen-1(2H)-one (25 g, 171 mmol) was added. The mixture was stirred at 0° C. for 30 minutes. t-Butyl nitrite was added to the reaction mixture (30 g, 256 mmol, 1.5 eq.). The reaction mixture was stirred at this temperature for an additional hour. The mixture was poured into cold water and extracted with EtOAc. The organic fractions were collected, dried, and concentrated. The residue was purified using silica gel chromatography (Hex/EtOAc). Desired product T was isolated as a mixture of two isomers.

Synthetic procedure for the preparation of (U): Performed according to the WO 2012/061530 (PCT/US2011/059018).

Synthetic procedure for the preparation of (V): Compound U (366 mg, 1.72 mmol) was dissolved in MeOH. To this solution, a suspension of Ni-Raney catalyst in water was added. The reaction mixture was stirred at room temperature while exposed to hydrogen gas (1 atm). After the reaction was complete, the mixture was filtered through the celite and concentrated. The residue was dissolved in dichloromethane and dried over MgSO$_4$. The drying agent was filtered off, and the product was carried on into the next step without further purifications. To the dichloromethane solution, reduced aminopyrazine derivative and N-Bromosuccinimide (207 mg, 1.17 mmol, 1 eq.) was added. The reaction mixture was stirred at room temperature for 4 hours. After that, it was poured into water, and organic fractions were extracted with dichloromethane. Organic fractions were collected, dried over MgSO$_4$, and concentrated under reduced pressure. The residue was purified by silica gel chromatography using Hept/EtOAc as eluent, providing desired compound V.

Synthetic procedure for the preparation of (W): In a 5 mL round bottom flask, aminopyrazine (250 mg, 0.9 mmol, 1 eq.), diazo compound (629 mg, 2.26 mmol, 2.5 eq.), Rh$_2$(OAc)$_4$ (40 mg, 0.09 mmol 10 mol %), and 3 mL of chlorobenzene were placed. The reaction mixture was heated at 100° C. for 24 hours. The progress of the reaction was monitored by LCMS. After 24 hours, the reaction reached 100% conversion. The mixture was adsorbed on celite and purified on a silica column using 40% EtOAc in Heptane as eluent. Yield, 323 mg, 67.8%.

Synthetic procedure for the preparation of (X): In a 20 mL vial, compound W (323 mg, 0.613 mmol, 1 eq.), furancarbaldehyde (64.8 mg, 0.675 mmol, 1.1 eq.), and 20 mL of methanol was placed. To that solution, 1,1,3,3-tetramethylguanidine (141 mg, 1.23 mmol, 2 eq.) was added, and the reaction mixture was stirred at room temperature for 1 hour. The progress of the reaction was monitored by LCMS. After the reaction was complete, the mixture was poured into water, extracted with ethyl acetate, and dried over MgSO$_4$. The drying agent was filtered off, and the solvent was concentrated under reduced pressure. The residue was purified using flash chromatography on silica gel with heptane/ethyl acetate (70/30) as eluent. Isolated 249 mg, Yield 86.6%.

Synthetic procedure for the preparation of (Y): In a parr-shaker reactor flask, compound X (249 mg, 0.53 mmol, 1 eq.), Rh(PPh$_3$)$_3$Cl (49 mg, 0.053 mmol, 0.1 eq.), and 30 mL of ethanol was placed. The reactor was charged with H$_2$ (50 psi) and shook for 20 hours at room temperature. The reaction was monitored by LCMS. Then, all volatiles were removed under reduced pressure, and the residue was subjected to flash chromatography on silica gel using heptane/ethyl acetate as eluent (70/30). Yield 187 mg, 74.8%.

Synthetic procedure for the preparation of formula (I-e): Compound Y (77.5 mg, 0.207 mmol, 1 eq.) was dissolved in dioxane (6 mL). To this solution, an appropriate boronic acid (0.228 mmol, 1.1 eq), Pd(PPh$_3$)$_2$Cl$_2$ (14.5 mg, 0.022 mmol, 0.1 eq.), and Cs$_2$CO$_3$ (0.675 mmol, of 1M solution, 3 eq.) were added. The reaction mixture was heated at 80° C. for 4 hours. The progress of the reaction was monitored by LCMS. After the reaction was complete, the reaction mixture was adsorbed on celite and purified by silica gel column chromatography using Heptane/EtOAc as eluent. Fractions containing the product Z were collected, concentrated under reduced pressure, and redissolved in 2 mL of dichloromethane. To this solution, 2 mL of TFA was added, and reaction mixture was stirred at room temperature for several hours (6-12 h.). The progress of the reaction was monitored by LCMS. After the reaction reached maximum conversion, all volatiles were removed under reduced pressure, and the residue was co-evaporated with toluene (2×30 mL) to remove the traces of TFA. The crude product was redissolved in dichloromethane (15 mL). Carbonyldiimidazole (100.9 mg, 0.622 mmol, 3 eq.) was added to the DCM solution, and the reaction mixture was stirred at room temperature for 30 minutes. The reaction mixture was poured into a 0.1 M solution of hydrochloric acid (100 mL). Organic fractions were extracted with dichloromethane, dried over MgSO$_4$, filtered, and concentrated under reduced pressure. The residue was loaded onto a silica gel column and purified using dichloromethane/methanol as eluent, providing the desired compound.

The following compounds were prepared using the general procedure of Method IV to provide compounds of formula (I-e). Appropriate substitution at the R$^8$ substitution site was achieved by using the appropriate organoborane reagent for the Suzuki coupling reactions.

| compound | Structure | Yield (%) | MS [M + H] |
|---|---|---|---|
| AS-342 | 12-(2-chloropyridin-4-yl)-2-(furan-2-ylmethyl)-5,11-dihydrobenzo[f]imidazo[1,2-a]quinoxalin-3(6H)-one | 17.5 | 429 |
| AS-340 | 5-(2-(furan-2-ylmethyl)-3-oxo-3,5,6,11-tetrahydrobenzo[f]imidazo[1,2-a]quinoxalin-12-yl)thiophene-2-carbonitrile | 8.4 | 425 |
| AS-341 | 2-(furan-2-ylmethyl)-12-(quinolin-4-yl)-5,11-dihydrobenzo[f]imidazo[1,2-a]quinoxalin-3(6H)-one | 14.7 | 445 |

Example 6

Prophetic Compounds of Formula (I)

The following compounds may be prepared using the disclosed synthetic procedures.

| compound | Structure |
|---|---|
| | 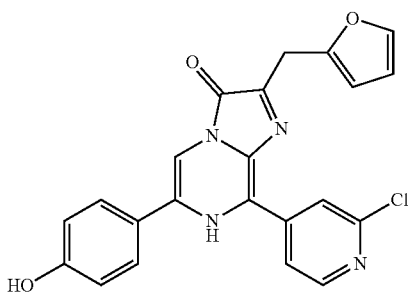 [SMILES: O=c1c(Cc2ccco2)nc2c(-c3ccnc(Cl)c3)[nH]c(-c3ccc(O)cc3)cn1-2]<br>8-(2-chloropyridin-4-yl)-2-(furan-2-ylmethyl)-6-(4-hydroxyphenyl)imidazo[1,2-a]pyrazin-3(7H)-one |
| | 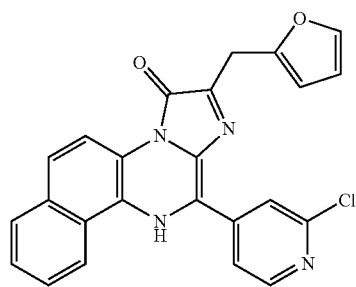 [SMILES: O=c1c(Cc2ccco2)nc2c(-c3ccnc(Cl)c3)[nH]c3c4ccccc4ccc3n1-2]<br>12-(2-chloropyridin-4-yl)-2-(furan-2-ylmethyl)benzo[f]imidazo[1,2-a]quinoxalin-3(11H)-one |
| | 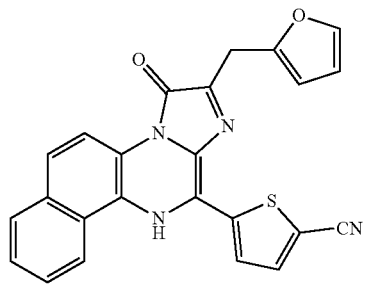 [SMILES: N#Cc1ccc(-c2[nH]c3c4ccccc4ccc3n3c(=O)c(Cc4ccco4)nc2-3)s1]<br>5-(2-(furan-2-ylmethyl)-3-oxo-3,11-dihydrobenzo[f]imidazo[1,2-a]quinoxalin-12-yl)thiophene-2-carbonitrile |
| | 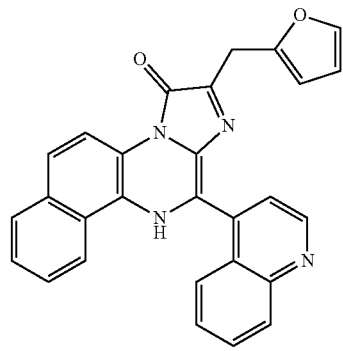 [SMILES: O=c1c(Cc2ccco2)nc2c(-c3ccnc4ccccc34)[nH]c3c4ccccc4ccc3n1-2]<br>2-(furan-2-ylmethyl)-12-(quinolin-4-yl)benzo[f]imidazo[1,2-a]quinoxalin-3(11H)-one |

Example 7

Luminescent Properties

Luminescence Assay Procedure: Each compound to be screened was dissolved in DMSO (5 mM) and then further diluted to 100 uM in NANO-GLO® Luciferase Assay Buffer. Each diluted substrate was then combined in equal volumes with purified NANOLUC® Luciferase diluted into $CO_2$ independent media+10% FBS. Initial light output for each substrate was measured in a GLOMAX®-Multi+ luminometer three minutes after substrate addition and then at five minute intervals as a means to determine signal half-life.

The synthesized coelenterazine analogues (compounds of formula (I) and (II)) were evaluated for their suitability as luciferase substrates. NANOLUC® luciferase was employed for the screening because it is a small (19 kDa), stable, and particularly bright enzyme. Table 1 demonstrates that the synthesized compounds possess relative light unit (RLUs) and half-life data that is comparable to a known coelenterazine analogue, 8-benzyl-2-(furan-2-ylmethyl)-6-phenylimidazo[1,2-a]pyrazin-3(7H)-one (furimazine), which is known to be superior to coelenterazine as a luciferase substrate. The data also show that many analogues produce red-shifted light as evidenced by an increase in λmax.

TABLE 1

| Compound | RLU (@100 uM) | half life @100 uM | λmax, nm |
|---|---|---|---|
| Furimazine | 1 | 1 | 460 |
| AS-410 | 6.3E−3 | 2.1 | |
| AS-141 | 3.7E−6 | 0.1 | |
| AS-142 | 1.7E−7 | 1.3 | |
| AS-143 | 1.7E−7 | 0.1 | |
| AS-144 | 8.4E−5 | 1.9 | |
| AS-154 | | | |
| AS-153 | 1.1E−3 | | |
| AS-155 | 7.4E−5 | | |
| JRW-0185 | 3.4E−4 | | |
| JRW-0231 | 1.9E−2 | | |
| JRW-0232 | 3.2E−2 | | |
| JRW-0236 | 0.03 | | |
| JRW-0238 | 0.99 | | |
| JRW-0446 | 0.014 | | 487 |
| JRW-0438 | 0.46 | | 487 |
| JRW-0445 | 0.24 | | 502 |
| AS-174 | 0.22 | | 496 |
| JRW-0240 | 1.3E−3 | | |
| AS-215 | 0.01 | | 517 |
| AS-216 | 3.5E−6 | | |
| AS-219 | 8.5E−6 | | |
| AS-218 | 8.9E−6 | | |
| AS-242 | 8.6E−5 | | 517 |
| AS-239 | 7E−6 | | |
| AS-221 | 8.9E−6 | | |
| AS-222 | 2.6E−7 | | |
| AS-240 | 2.6E−6 | | |
| AS-223 | 2.1E−6 | | |
| AS-227 | 4.2E−4 | | |
| AS-250 | 4.E−5 | | 511 |
| AS-243 | 2.2E−7 | | |
| AS-245 | 1.1E−6 | | |
| AS-258 | | | |
| AS-256 | 3.6E−4 | | 496 |
| AS-270 | 4.6E−3 | | 502 |
| AS-269 | 0.26 | | 490 |
| AS-238 | 5.6E−7 | | |
| AS-237 | 1.4E−4 | | 559 |
| AS-274 | 2E−3 | | 514 |
| AS-224 | 1E−5 | | 502 |
| AS-229 | 6.4E−3 | | 496 |
| AS-236 | 4.7E−3 | | 514 |

TABLE 1-continued

| Compound | RLU (@100 uM) | half life @100 uM | λmax, nm |
|---|---|---|---|
| AS-262 | 2E−3 | | 574 |
| AS-280 | 6E−3 | | 523 |
| AS-282 | 9E−3 | | 505 |
| AS-277 | 3E−3 | | 517 |
| AS-273 | 0.013 | | 496 |
| AS-272 | 6E−3 | | 508 |
| AS-278 | 7E−4 | | 499 |
| AS-276 | 0.015 | | 523 |
| AS-271 | 0.048 | | 532 |
| AS-275 | 0.098 | | 535 |
| AS-310 | 9.99E−3 | | 571 |
| AS-313 | 3.62E−5 | | |
| AS-315 | 1.36E−3 | | |
| AS-314 | 1.81E−2 | | 538 |
| AS-343 | 5.54E−4 | | |
| AS-311 | 7.42E−3 | | 505 |
| AS-175 | 3.8E−3 | | 514 |
| AS-176 | 1.3E−3 | | 496 |
| AS-190 | 4.8E−6 | | 496 |
| AS-306 | 6.62E−3 | | 544 |
| AS-287 | 1.8E−4 | | 556 (Autolum) |
| AS-295 | 6.78E−5 | | 520 (Autolum) |
| AS-333 | 9.16E−4 | | 571 |
| AS-330 | 6.94−4 | | 583 |
| AS-332 | 1.05E−4 | | 598 |
| AS-337 | 7.36E−5 | | |
| AS-248 | 3.3E−4 | | 520 |
| AS-329 | 4.58E−6 | | |
| AS-321 | 2.2E−5 | | |
| AS-320 | 1.4E−5 | | |
| AS-319 | 4.69E−6 | | |
| AS-301 | 8.45E−5 | | 529 |
| AS-292 | 1.16E−6 | | |
| AS-293 | 1.86E−6 | | 596 (Autolum) |
| AS-342 | 4.77E−2 | | 538 |
| AS-340 | 8.72E−5 | | 574 |
| AS-341 | 5.36E−3 | | 583 |

Example 8

Screening 6′OH Coelenterazine Analogs with NanoLuc and *Renilla* Luciferase

Luminescence Assay Procedure: Each compound to be screened was diluted to a concentration of 100 uM in *Renilla* Glo Luciferase Assay buffer (Promega Corporation) and then further diluted to 2× serial dilution in *Renilla* Glo Luciferase Assay Buffer. NANOLUC® luciferase and *Renilla* luciferase were diluted to a concentration of 4 ng/ml in OptiMEM+0.1% FBS. 50 ul of each compound dilution was then mixed with 50 ul of each enzyme dilution and incubated for 1 minute at room temperature. Light output for each compound was measured on a GLOMAX®-Multi+ luminometer. Km and Vmax were calculated for each enzyme/substrate combination using a GraphPad Prism Michaelis-Menten non-linear fit (FIGS. 1A-1D).

FIGS. 1A-1D demonstrate that *Renilla* luciferase produced ~7× more light with Coelenterazine-H compared to Furimazine. NanoLuc® luciferase produced significantly more light than *Renilla* with both furimazine and Coelenterazine-H.

TABLE 2

| | NanoLuc Fz | NanoLuc Coel-H | Renilla Fz | Renilla Coel-H |
|---|---|---|---|---|
| Vmax | 33,470,000 | 19,790,000 | 8,910 | 64,494 |
| Km | 9.37 | 36.4 | 10.63 | 3.259 |

Example 9

Autoluminescence Determination

A. Substrate Titration

Luminescence Assay Procedure: Each compound to be screened was diluted to a concentration of 100 uM in *Renilla* Glo Luciferase Assay buffer (Promega Corporation), and 50 ul mixed with 50 ul of OptiMEM+0.1% FBS. Light output for each compound was measured on a GLOMAX®-Multi+ luminometer.

Figure 2A:
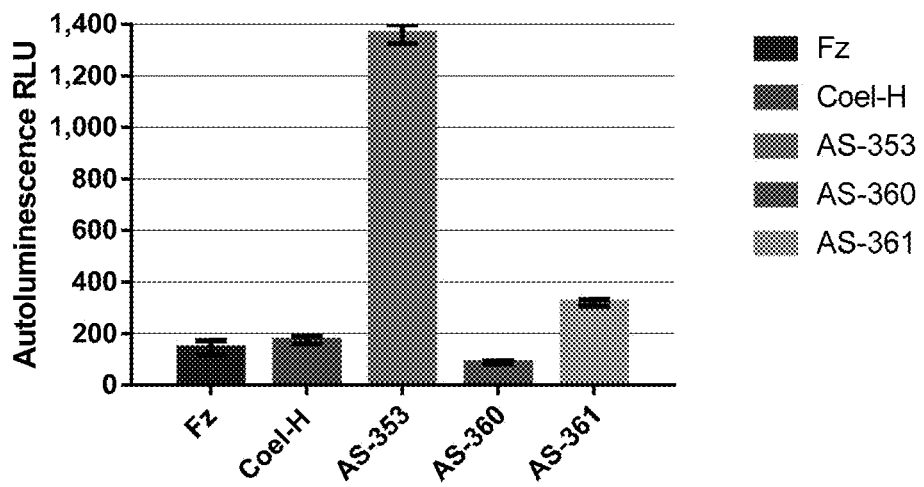
FIGS. 2A and 2B show autoluminescence determinations under substrate and enzyme titration conditions.

FIG. 2A demonstrates that AS-353 produced ~9× more autoluminescence compared to Furimazine or coelenterazine-H, and AS-361 produced ~2× more autoluminescence compared to Furimazine or Coelenterazine-H.

B. Enzyme Titration

Luminescence Assay Procedure: *Renilla* luciferase and NanoLuc Luciferase were diluted to a concentration of 4 ug/ml (4 ng/uL) in OptiMEM+0.1% FBS. 10× serial dilutions of the luciferases were then prepared in OptiMEM+0.1% FBS. Each substrate was diluted to 100 uM into *Renilla* Glo Luciferase assay buffer (Promega Corporation). The 10× enzyme serial dilutions were then combined with the substrate dilutions, 50 ul mixed with 50 ul compound, and incubated for 1 minute at room temperature. Light output for each compound was measured on a GLOMAX®-Multi+luminometer.

Figure 2B:
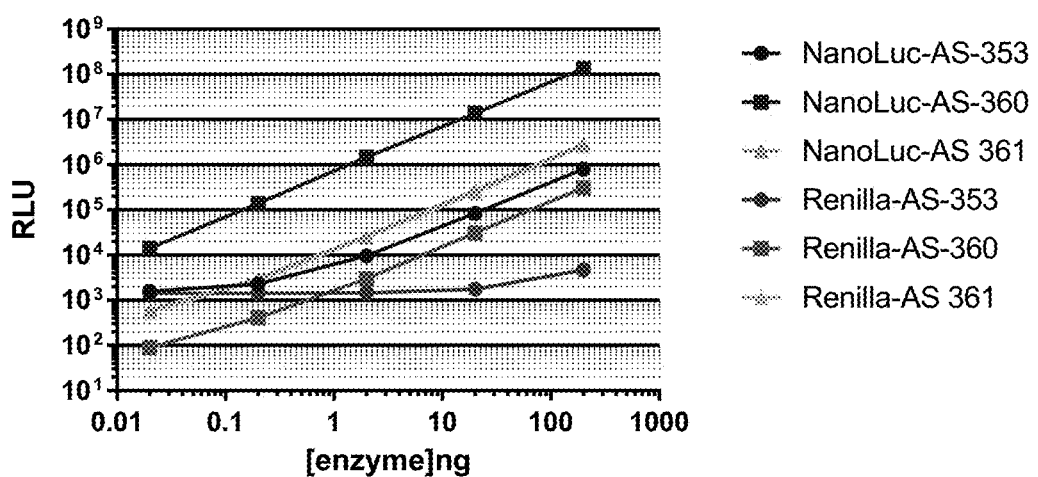
Figure 3A:
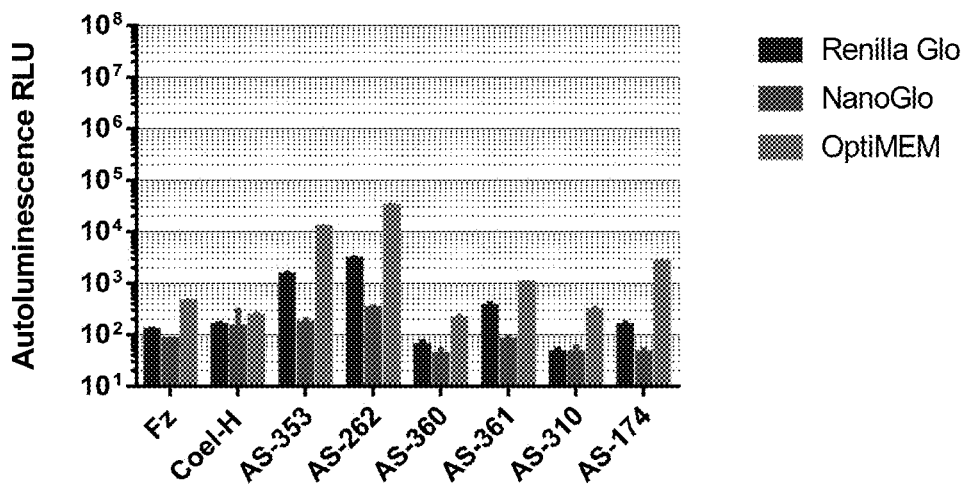
FIGS. 3A-3C show luminescence and autoluminescence determinations in various buffers using Nanoluc® Luciferase or *Renilla* Luciferase.
Figure 3B:
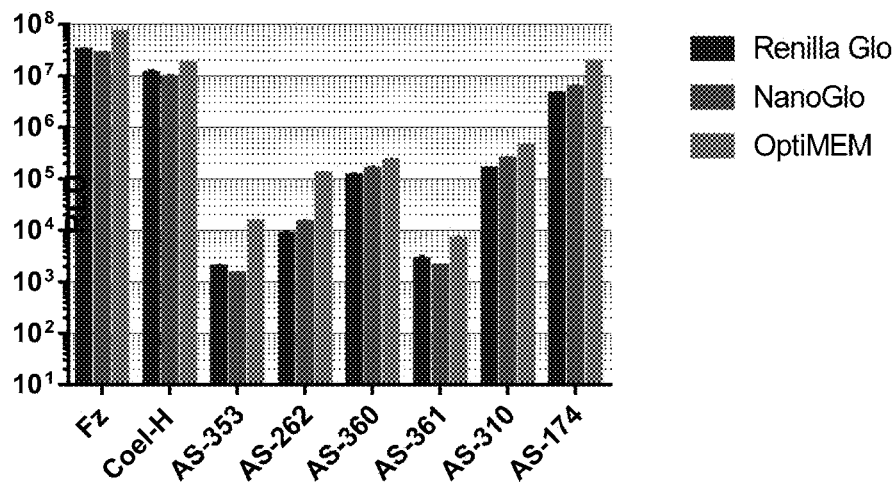
Figure 3C:
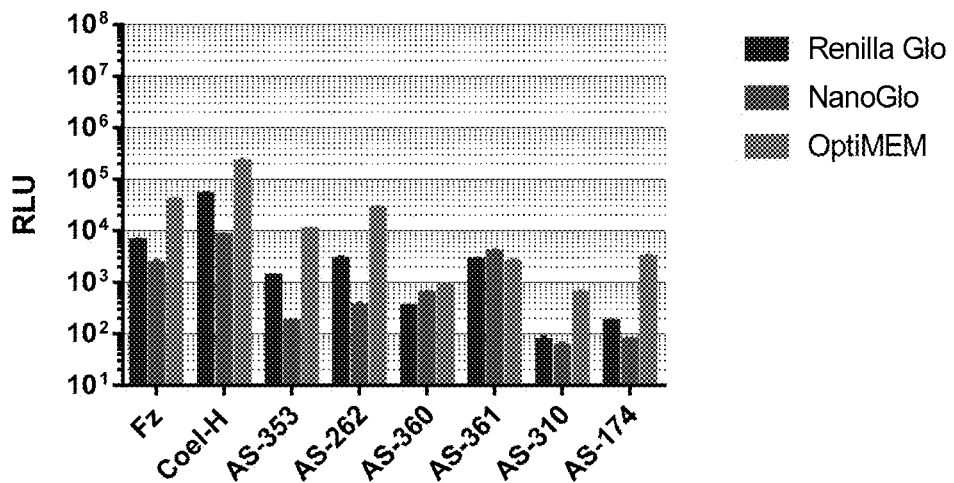
Figure 4A:
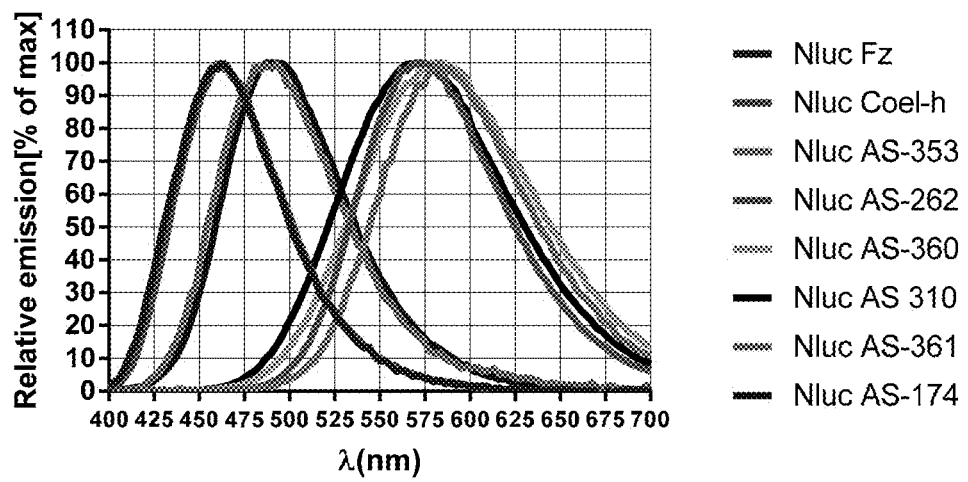
FIGS. 4A-4D show spectral profiles in various buffers using Nanoluc® Luciferase or *Renilla* Luciferase.
Figure 4B:
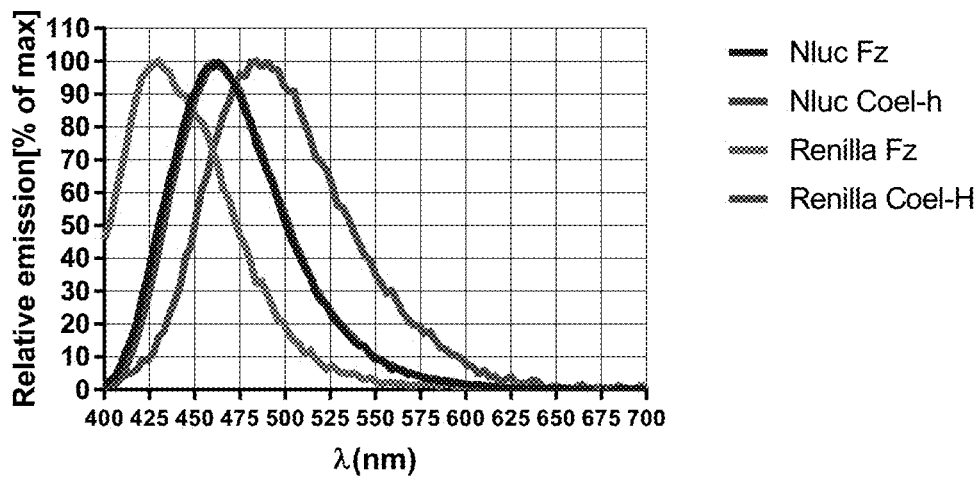
Figure 4C:
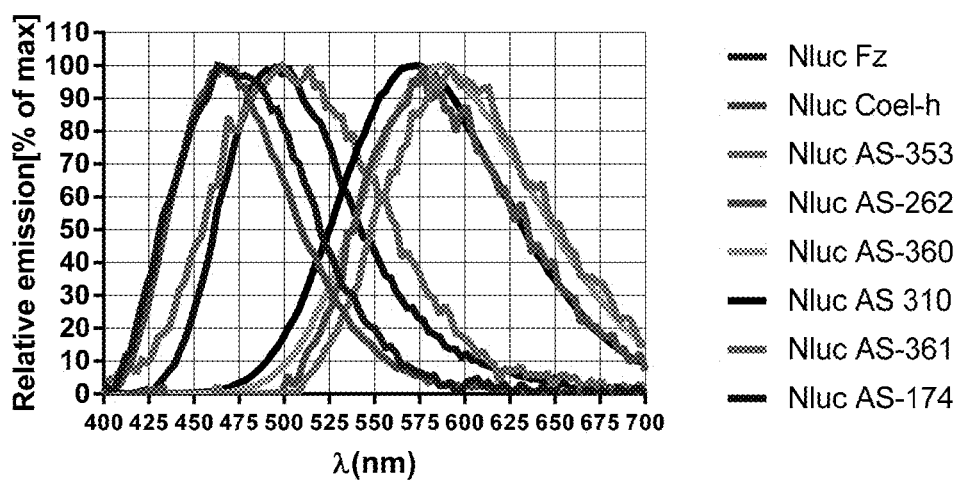
Figure 4D:
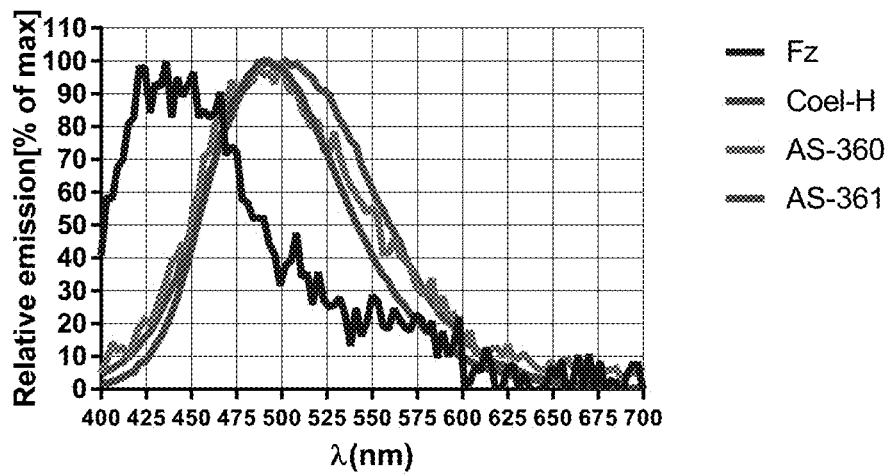
Figure 5A:
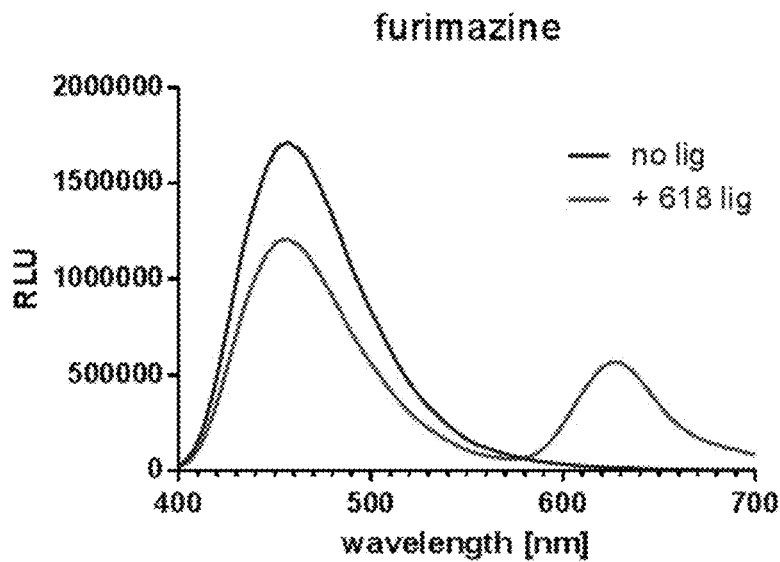
FIGS. 5A-5I show bioluminescent resonance energy transfer (BRET) spectral measurements.
Figure 5B:
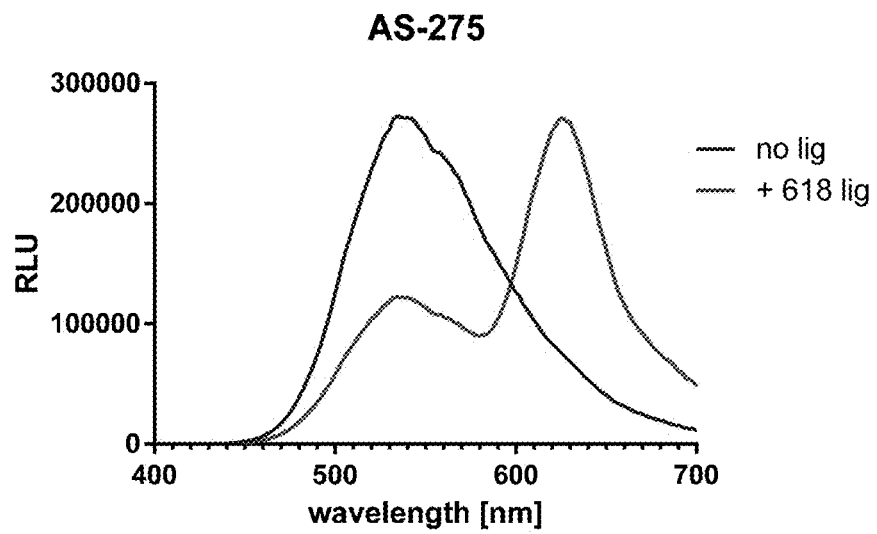
Figure 5C:
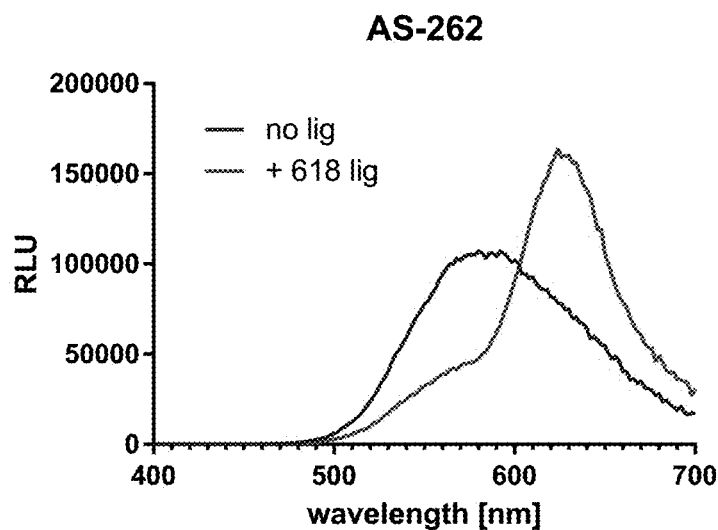
Figure 5D:
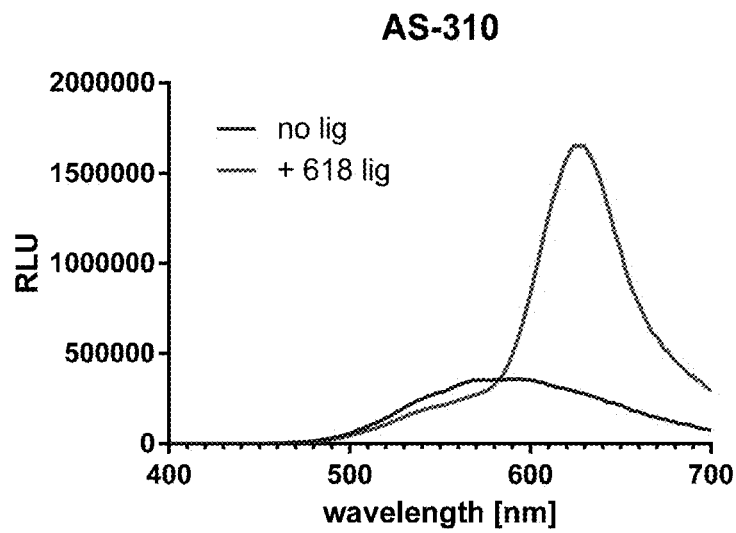
Figure 5E:
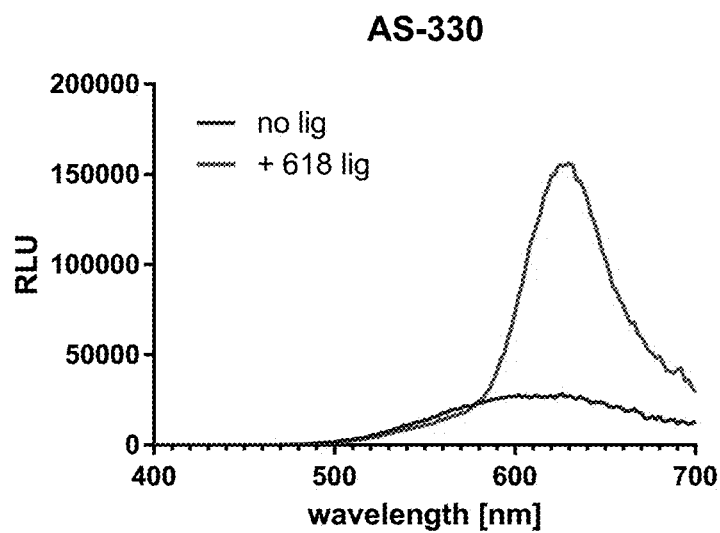
Figure 5F:
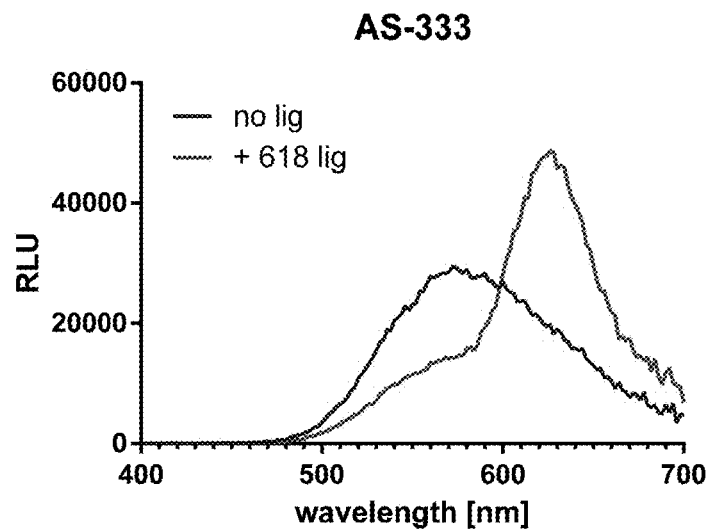
Figure 5G:
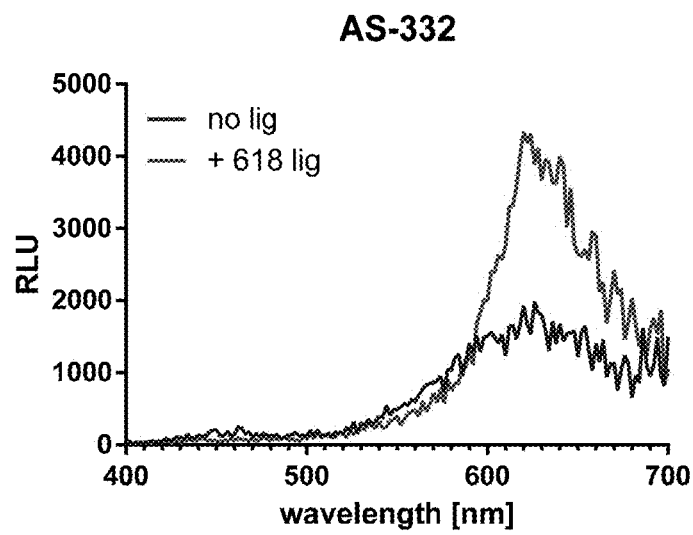
Figure 5H:
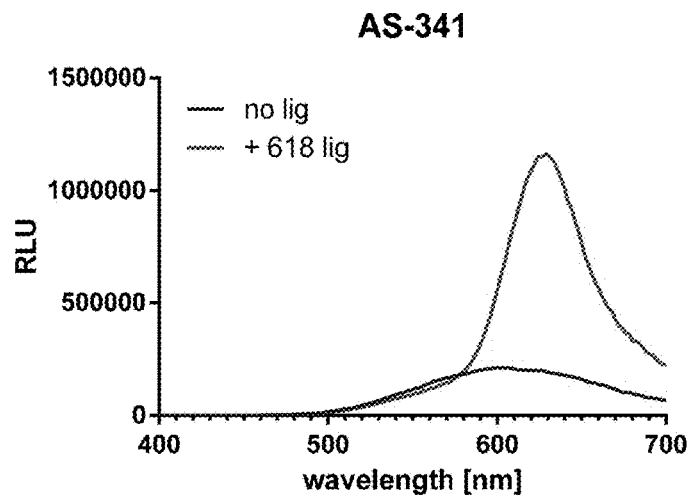
Figure 5I:
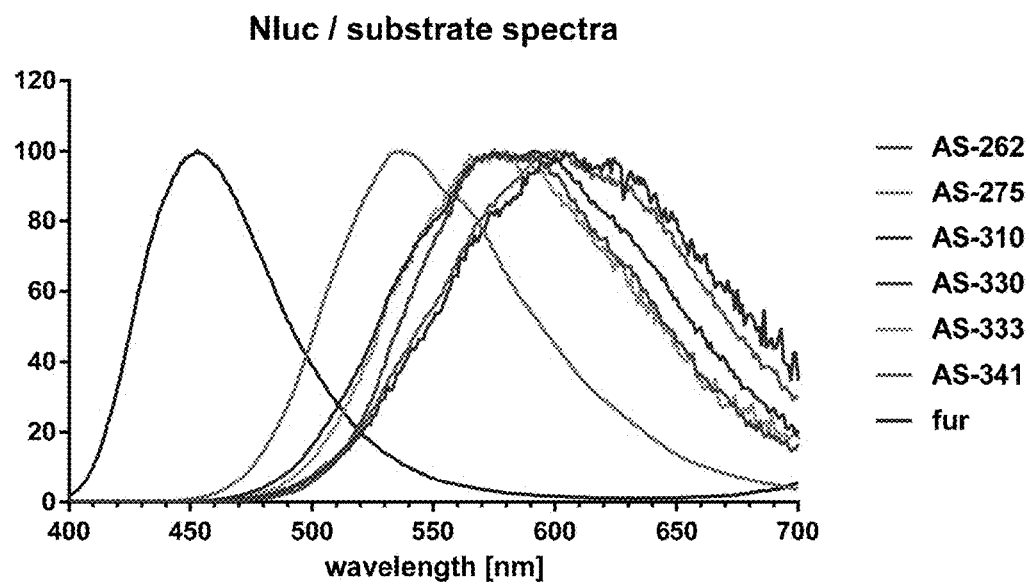
Figure 6A:
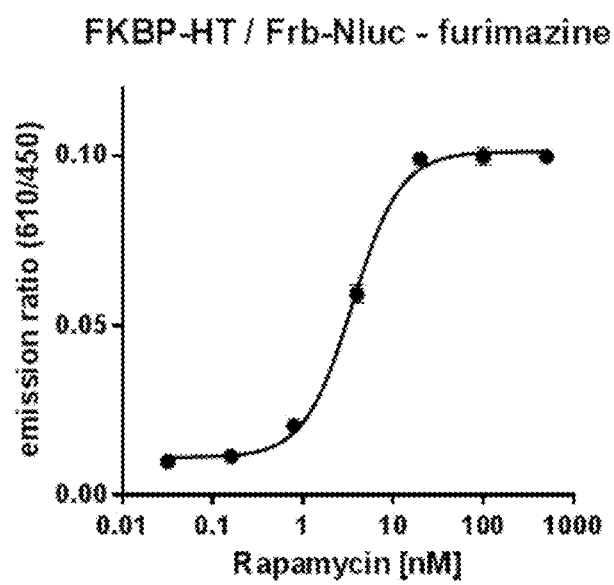
FIGS. 6A-6F show the change in bioluminescent resonance energy transfer (BRET) induced by increasing concentrations of rapamycin in a live cell BRET model for the interaction of FKBP and Frb.
Figure 6B:
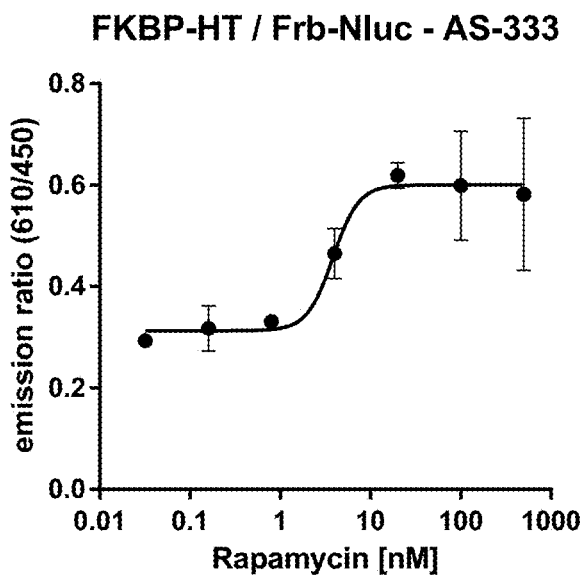
Figure 6C:
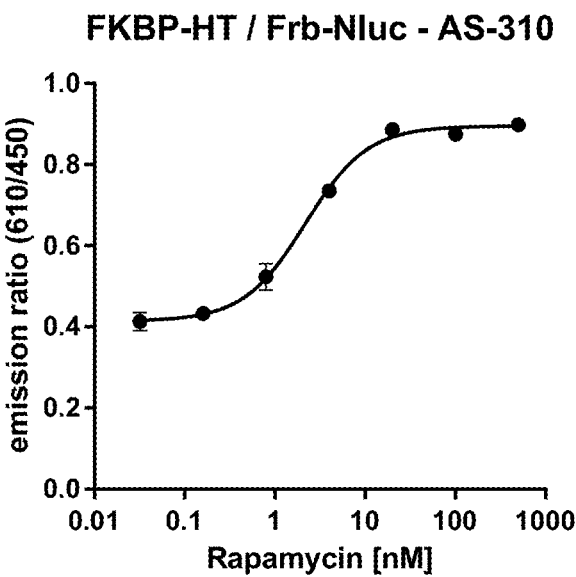
Figure 6D:
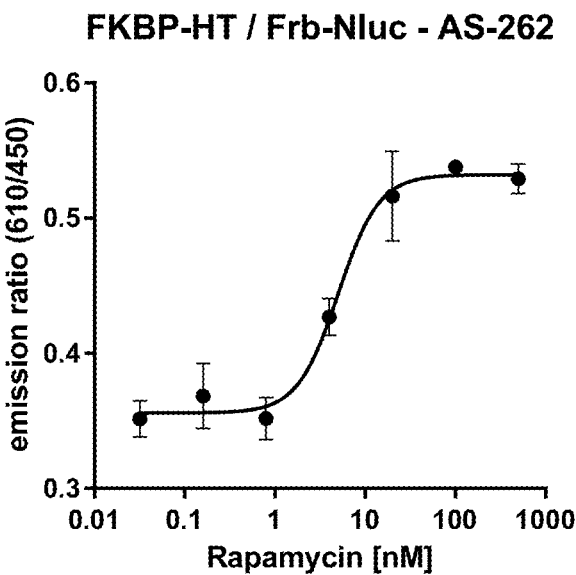
Figure 6E:
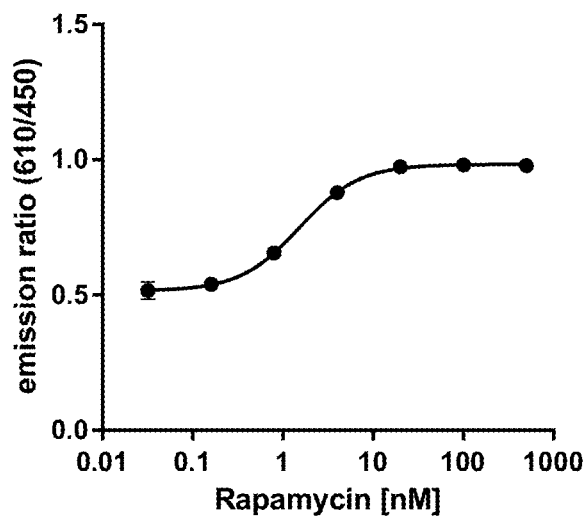
Figure 6F:
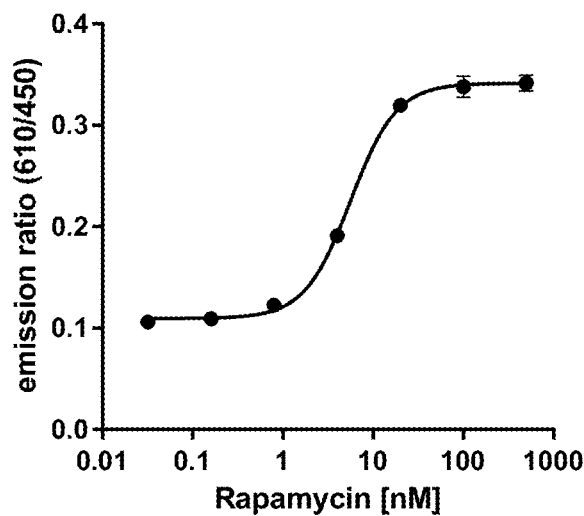
Figure 7A:
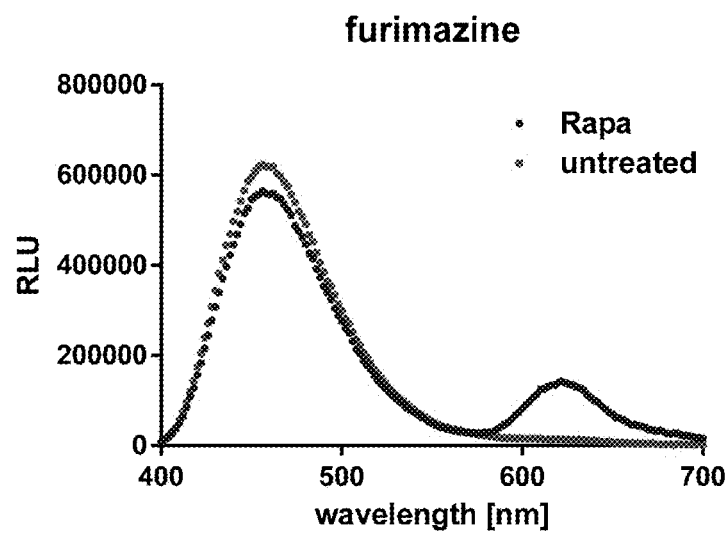
FIGS. 7A-7F show rapamycin induced change in bioluminescent resonance energy transfer (BRET) spectrum in a live cell BRET model for the interaction of FKBP and Frb.
Figure 7B:
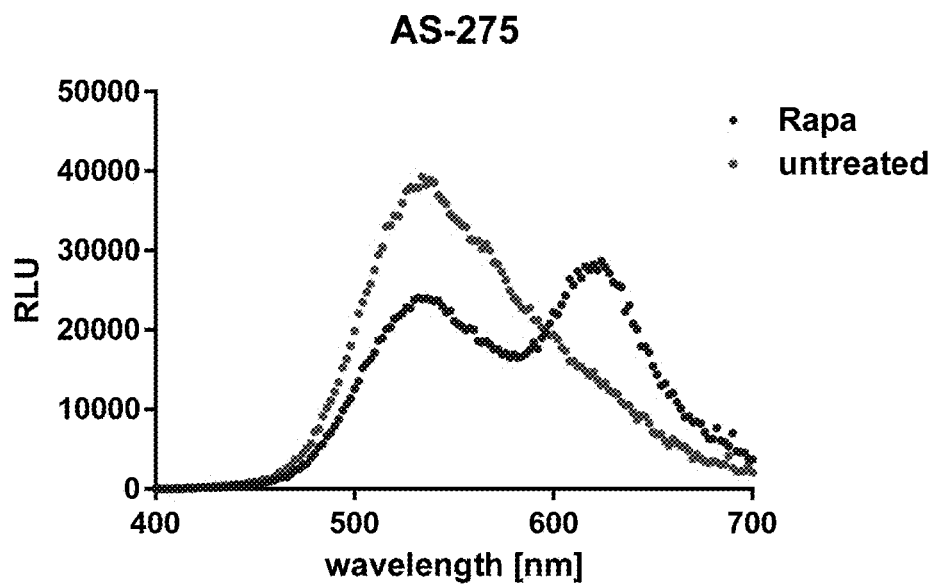
Figure 7C:
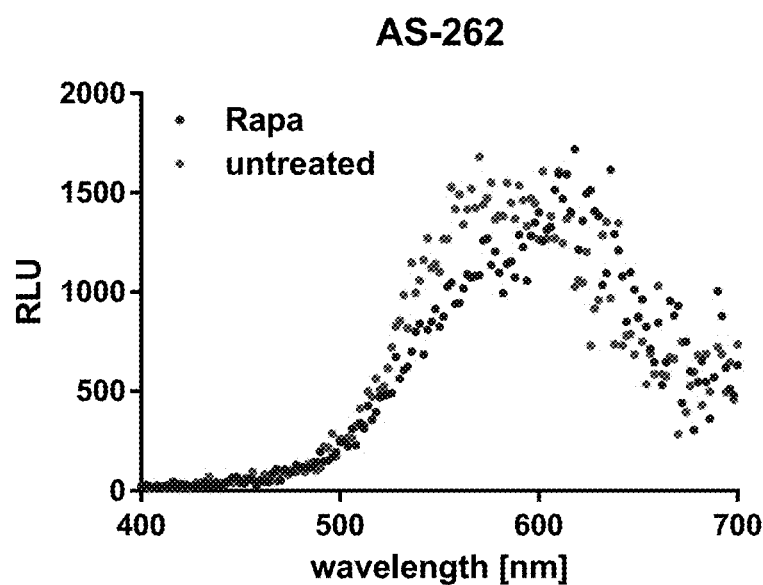
Figure 7D:
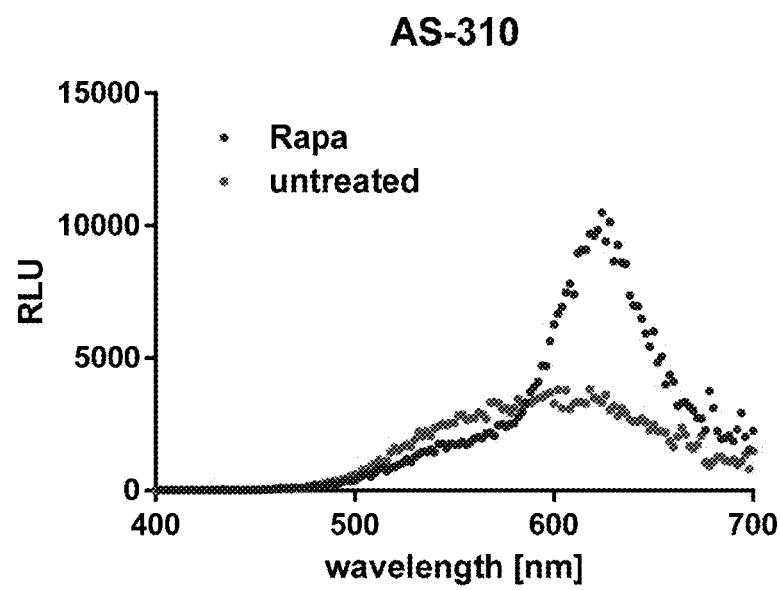
Figure 7E:
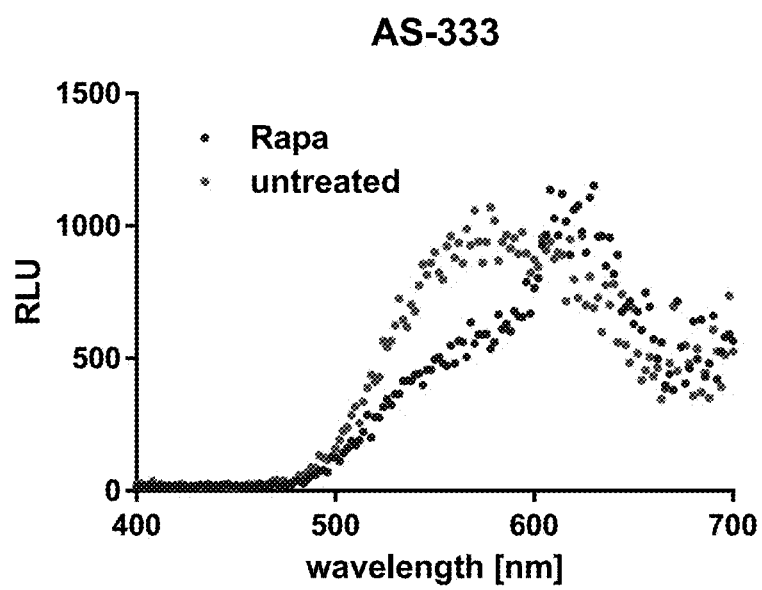
Figure 7F:
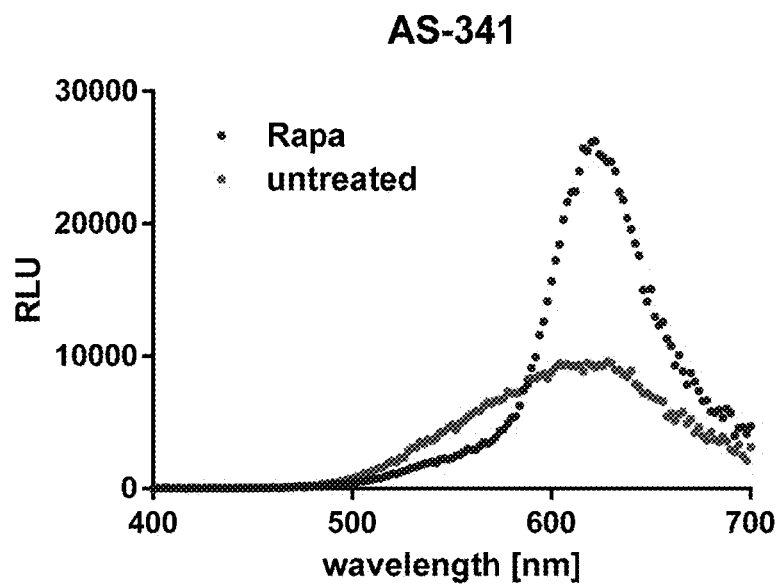

FIG. 2B demonstrates that the combination of NanoLuc® luciferase and AS-360 provides the brightest luminescence in the panel tested and is nearly 30× brighter than both *Renilla* and NanoLuc® luciferase with AS-361. AS-353 produces ~100× lower RLU values with NanoLuc compared to AS-360. *Renilla* Luciferase produces enzyme dependent luminescence with AS-353 only at the highest enzyme concentration.

Example 10

Luminescence and Autoluminescence Determination in Various Buffers Using NANOLUC® Luciferase or *Renilla* Luciferase Luminescence Assay Procedure: Each compound to be screened was diluted to a concentration of 100 uM (50 uM final concentration) in *Renilla* Glo Luciferase Assay buffer (Promega Corporation), NANO-GLO Luciferase Assay Buffer (Promega Corporation), or 20 uM (10 uM final) in OptiMEM+0.1% FBS. NANOLUC® luciferase and *Renilla* luciferase were serially diluted to 4, 40, and 400 ng/ml in OptiMEM+0.1% FBS. 50 ul of each compound dilution was mixed with 50 ul enzyme dilution and incubated for 1 minute at room temperature. Autoluminescence spectra of AS-353 was measured by adding 20 uM of substrate to OptiMEM+20% FBS and then 50 ul of this dilution was combined with 50 ul of OptiMEM+0.1% FBS. Spectral measurements were measured using a Tecan M-1000 luminometer. (3 nM intervals/20 nM bandpass).

FIGS. 3A-3C and FIGS. 4A-4D demonstrate that all of the substrates tested shifted the NanoLuc® luciferase spectral properties to red (AS-353, AS-360, AS-361, AS-262, AS-310, AS-174). The spectral properties of *Renilla* were shifted to blue with ~50 nM with Furimazine compared to Coelenterazine-H. The only substrate tested that shifted the *Renilla* spectra to red was AS-361.

TABLE 3

| Substrate | Low | Peak | High | Width |
|---|---|---|---|---|
| NanoLuc OptiMEM + 0.1% FBS | | | | |
| Fz | 430 | 463 | 499 | 69 |
| Coel-H | 433 | 460 | 502 | 69 |
| AS-353 | 544 | 583 | 637 | 93 |
| AS-262 | 532 | 574 | 625 | 93 |
| AS-360 | 532 | 583 | 646 | 114 |
| AS-310 | 520 | 571 | 631 | 111 |
| AS-361 | 454 | 493 | 535 | 81 |
| AS-174 | 460 | 490 | 535 | 75 |
| Renilla-Fz | 403 | 430 | 472 | 69 |
| Renilla-Coel-H | 451 | 487 | 535 | 84 |
| NanoLuc NanoGlo Buffer | | | | |
| Fz | 433 | 463 | 520 | 87 |
| Coel-H | 433 | 466 | 508 | 75 |
| AS-353 | 550 | 592 | 652 | 102 |
| AS-262 | 535 | 577 | 634 | 99 |
| AS-360 | 538 | 589 | 647 | 109 |
| AS-310 | 526 | 574 | 631 | 105 |
| AS-361 | 457 | 499 | 562 | 105 |
| AS-174 | 460 | 493 | 541 | 81 |
| Renilla/RenillaGlo | | | | |
| Fz | 403 | 436 | 490 | 87 |
| Coel-H | 454 | 490 | 541 | 87 |
| AS-360 | 451 | 487 | 553 | 102 |
| AS-361 | 451 | 502 | 559 | 108 |

TABLE 4

| Substrate | OptiMEM | NanoGlo | RenillaGlo | Autoluminescence |
|---|---|---|---|---|
| Fz | 463 | 463 | | |
| Coel-H | 460 | 466 | | |
| AS-353 | 583 | 592 | | 574 |
| AS-262 | 574 | 577 | | |
| AS-360 | 583 | 589 | | |
| AS-310 | 571 | 574 | | |
| AS-361 | 493 | 499 | | |
| AS-174 | 490 | 493 | | |
| Renilla-Fz | 430 | | 436 | |
| Renilla-Coel-H | 487 | | 490 | |
| Renilla AS-360 | | | 487 | |
| Renilla AS-361 | | | 502 | |

Example 11

BRET (Bioluminescent Resonance Energy Transfer) Spectral Measurements

A. In Vitro

Assay Procedure: Each compound to be screened was diluted to a concentration of 50 uM in PBS. Then, 5 nM of a NanoLuc-HaloTag fusion protein (Promega Corporation), 5 nM NanoBRET618 HALOTAG® ligand, and 50 μM compound were combined, and spectral measurements taken using a BMG ClarioStar (500 msec integration time, 2 nm intervals/20 nm bandpass). A "no acceptor" control containing only the NanoLuc-HaloTag fusion protein (i.e., no NanoBRET618 HALOTAG® ligand) was also performed for each compound to determine emission spectra of the compounds.

The results in FIGS. 5A-5I demonstrate that the compounds tested in this experiment are suitable as donors for BRET based detection systems. In addition, the data indicates that energy transfer efficiency increases when decreasing the spectral separation between the compound (BRET donor) and NanoBRET618 HALOTAG® ligand (acceptor).

B. Protein-Protein Interaction in HeLa Cells

Assay Procedure: HeLa cells were transiently transfected with constructs for the expression of Frb-NANOLUC® fusion protein and FKBP-HALOTAG® fusion protein (both from Promega Corporation) at a 1:5 DNA ratio and plated in a white 96-well tissue culture plate at a density of 20,000 cells per well in DMEM+10% FBS. After 24 hours, the cells were labeled (FKBP-HaloTag) by replacing the medium with OptiMEM containing 250 nM NanoBRET618 HALOTAG® ligand (Promega Corporation) followed by a 60 minute incubation. The protein-protein interaction (PPI) between FKBP-HaloTag and Frb-NanoLuc was induced by the addition of either a serial dilution of rapamycin (FIGS. 6A-6F) or 1 uM rapamycin (FIGS. 7A-7F) followed by a 10 minute incubation period. Each compound was then added to a well of cells at a final concentration of 50 uM. Spectral measurements were taken immediately after compound addition on a BMG ClarioStar (500 msec integration time, 2 nm intervals/20 nm bandpass).

The results in FIGS. 6A-6F demonstrate the use of the compounds as a donor in a BRET-based assay for the detection of protein-protein interactions in living cells. The treatment with rapamycin leads to a dose dependent change in the emission ratio (610/460) indicative of the change in energy transfer between the compounds (donor) and NanoBRET618 substrate.

The results in FIGS. 7A-7F show a comparison of emission spectra obtained from untreated and rapamycin treated cells respectively to demonstrate the treatment induced change in energy transfer between the compounds (donor) and NanoBRET618 substrate.

Example 12

Effect of Substrates on Cell Viability

Figure 8A:
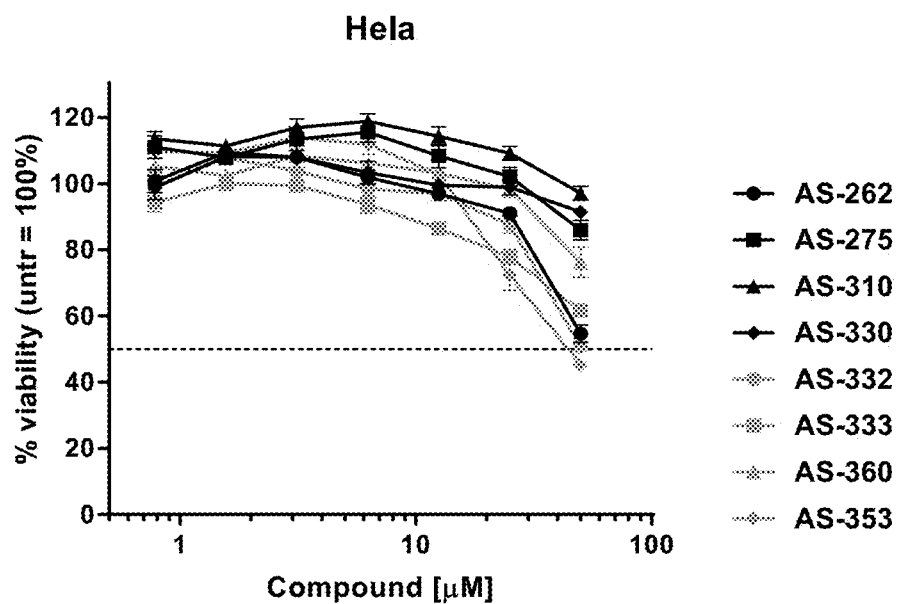
FIG. 8A shows substrate effects on viability of Hela cells.
Figure 8B:
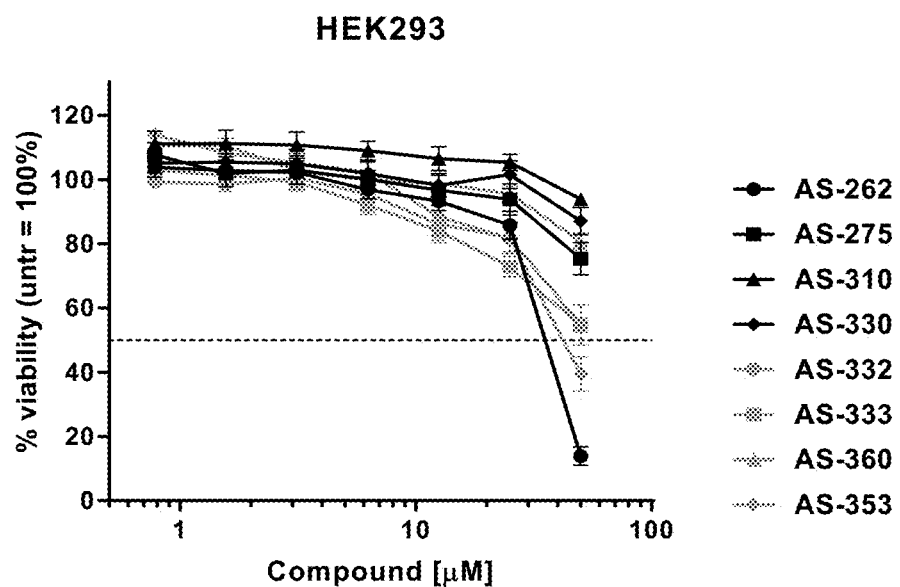
FIG. 8B shows substrate effects on viability of HEK293 cells.

Assay Procedure: HEK293 or HeLa cells were plated into wells of a white, 96-well tissue culture plate in 100 ml DMEM+10% FBS and incubated for 24 h at 37° C. The medium was then replaced with 100 ml DMEM+10% FBS supplemented with a serial titration of the indicated substrate followed by 6 h incubation at 37° C. Cell viability was assessed using CellTiter Glo (Promega) following manufacturer's instructions. FIGS. 8A-8B show the means±SEM of 3 independent experiments performed in triplicate.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method for in vivo bioluminescent imaging, the method comprising:
  contacting a live cell with a compound of Formula I or Formula II:

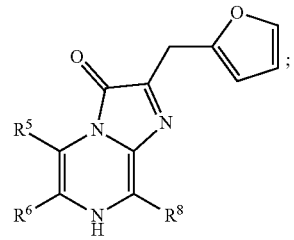

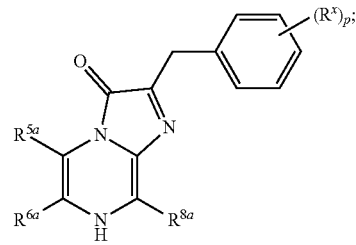

wherein $R^5$ and $R^{5a}$ are hydrogen;

$R^6$ and $R^{6a}$ are aryl optionally substituted with 1, 2, 3, 4, or 5 substituents independently selected from the group consisting of halogen, hydroxy, cyano, nitro, amino, alkylamino, dialkylamino, acyl amino, aminoalkyl, alkyl, fluoroalkyl, alkoxyfluoroalkyl, fluoroalkoxy, alkenyl, alkynyl, haloalkyl, haloalkoxy, heteroalkyl, alkoxy, sulfonylamino, sulfonyl, alkylsulfonyl, amide, carbamate, silyl, substituted silyl, acyl, or aminosulfonyl;

$R^8$ and $R^{8a}$ are optionally substituted aryl, heteroaryl, alkyl substituted with aryl, or alkyl substituted with heteroaryl;

$R^x$ is halogen, hydroxy, cyano, nitro, amino, alkylamino, dialkylamino, alkyl, alkenyl, alkynyl, alkoxy, or heteroalkyl; and p is 0, 1, 2, 3, 4, or 5;

provided that the following compounds are excluded from formula (I): 8-benzyl-2-(furan-2-ylmethyl)-6-phenylimidazo[1,2-a]pyrazin-3(7H)-one; and 8-benzyl-2-(furan-2-ylmethyl)-6-(4-hydroxyphenyl)imidazo[1,2-a]pyrazin-3(7H)-one; and $R^x$ is not 4-hydroxy when p is 1, $R^{5a}$ is not hydrogen, or $R^{8a}$ is not benzyl, or any combination thereof;

and detecting luminescence; wherein the live cell expresses a coelenterazine-utilizing luciferase.

2. The method of claim 1, wherein:

$R^6$ and $R^{6a}$ are phenyl optionally substituted with 1, 2, 3, 4, or 5 substituents independently selected from the group consisting of halogen, hydroxy, cyano, nitro, amino, alkylamino, dialkylamino, acyl amino, aminoalkyl, alkyl, fluoroalkyl, alkoxyfluoroalkyl, fluoroalkoxy, alkenyl, alkynyl, haloalkyl, haloalkoxy, heteroalkyl, alkoxy, sulfonylamino, sulfonyl, alkylsulfonyl, amide, carbamate, silyl, substituted silyl, acyl, or aminosulfonyl.

3. The method of claim 1, wherein $R^6$ and $R^{6a}$ are

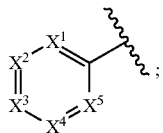

$X^1$-$X^5$ are each independently $CR^{11}$; and
$R^{11}$, at each occurrence, is independently selected from the group consisting of hydrogen, halogen, hydroxy, cyano, amino, nitro, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkylamino, $C_1$-$C_6$-dialkylamino, and $C_1$-$C_6$-heteroalkyl.

4. The method of claim 3, wherein $R^8$ and $R^{8a}$ are selected from the group consisting of:

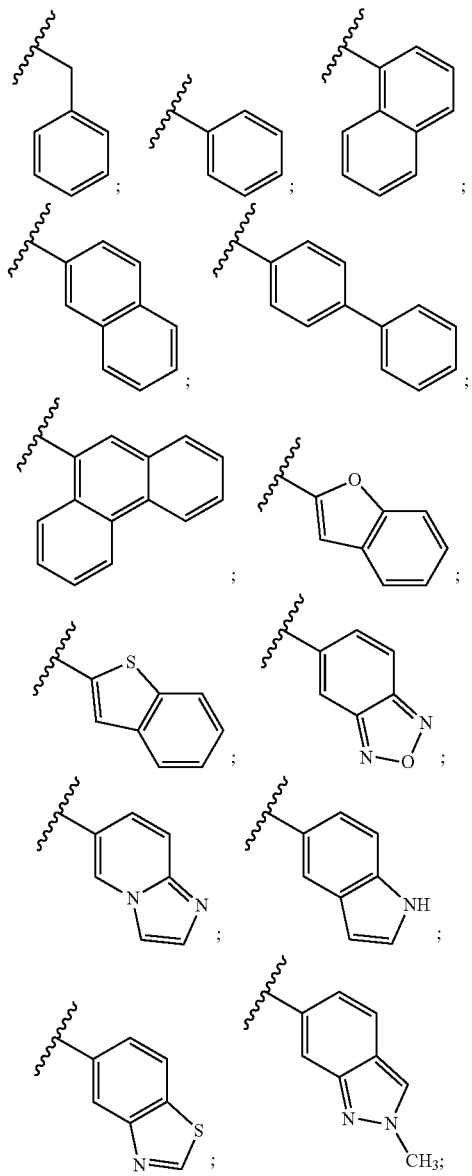

-continued

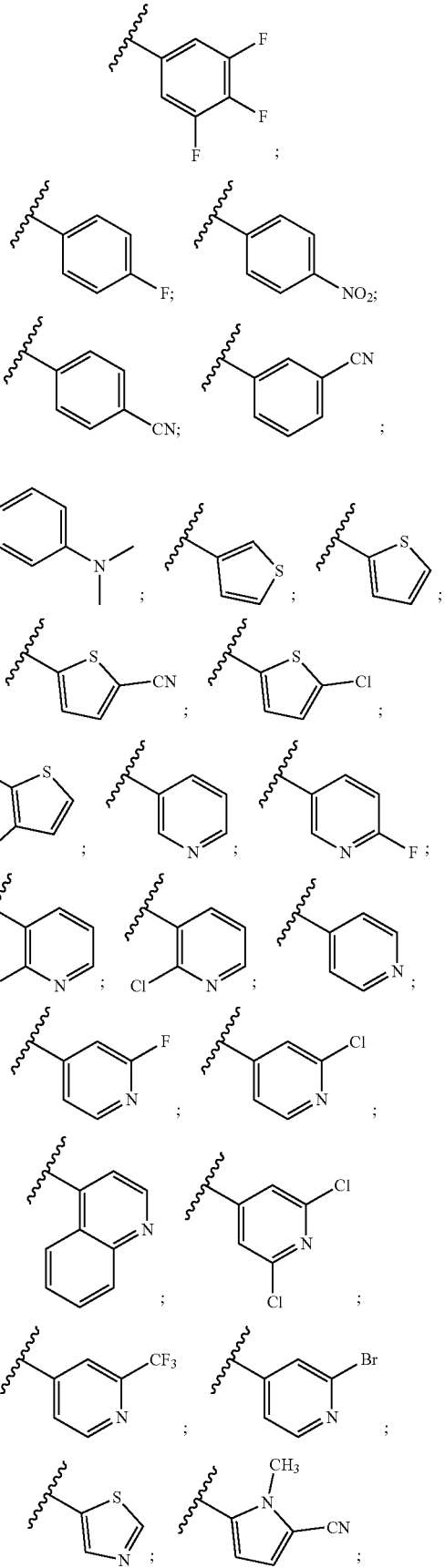

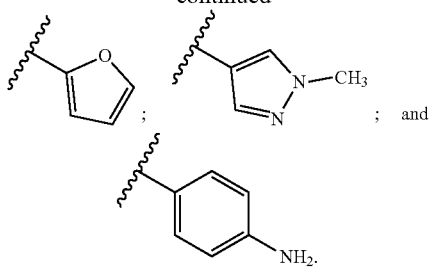

5. The method of claim 3, wherein the compound is of formula (I); $R^{11}$ at $X^1$, $X^3$, $X^4$, and $X^5$ is hydrogen; and the $R^{11}$ at $X^2$ is hydrogen, hydroxy, amino, $C_1$-$C_6$-alkoxy, $C_1$-$C_6$-haloalkoxy, $C_1$-$C_6$-alkylamino, $C_1$-$C_6$-dialkylamino, or $C_1$-$C_6$-heteroalkyl.

6. The method of claim 3, wherein the compound is of formula (I); and $R^6$ is selected from the group consisting of:

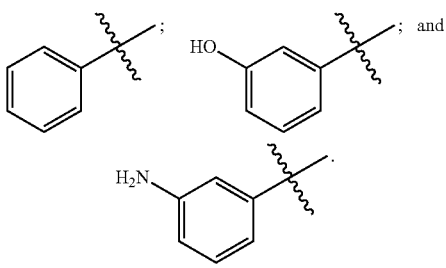

7. The method of claim 5, wherein $R^8$ is selected from the group consisting of:

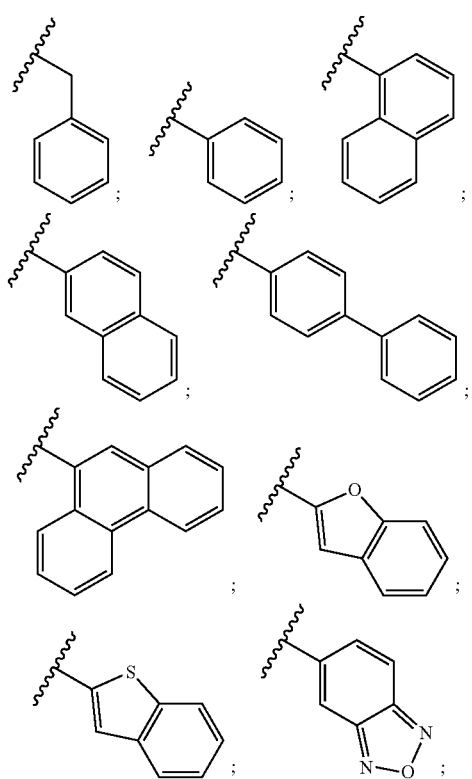

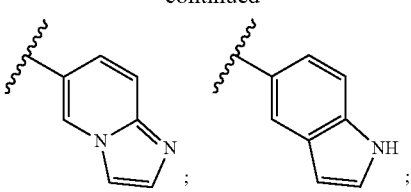

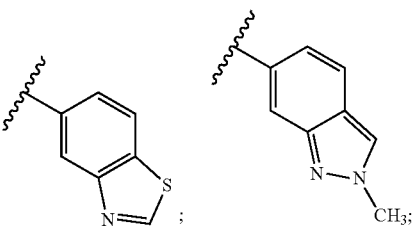

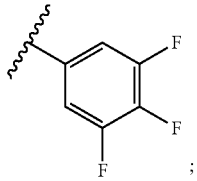

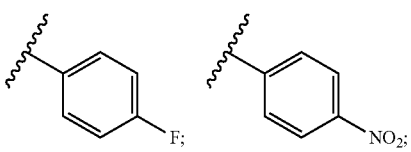

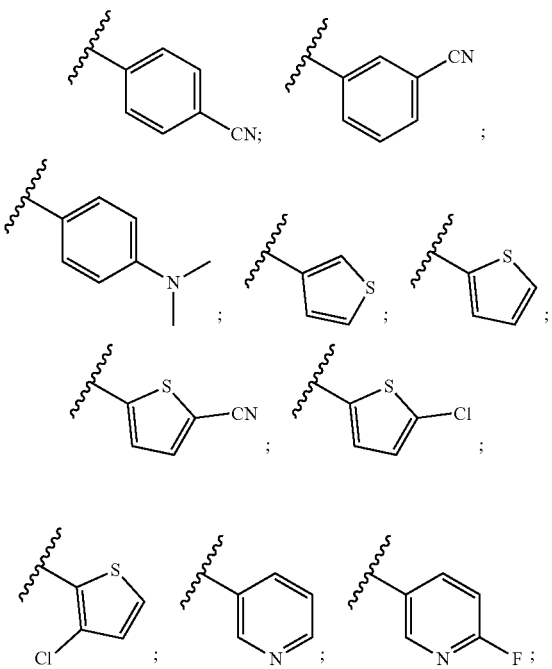

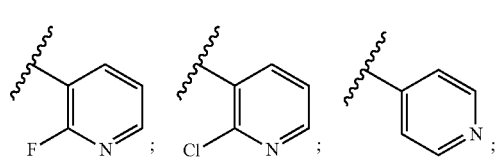

-continued

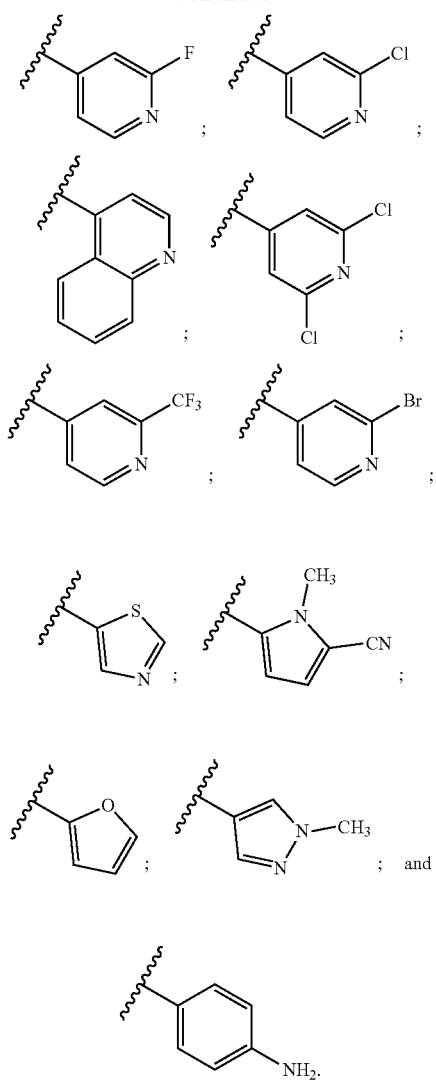

8. The method of claim 5, wherein R⁸ is

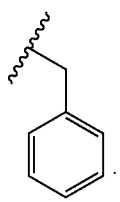 [SMILES: *Cc1ccccc1]

9. The method of claim 7, wherein the compound is

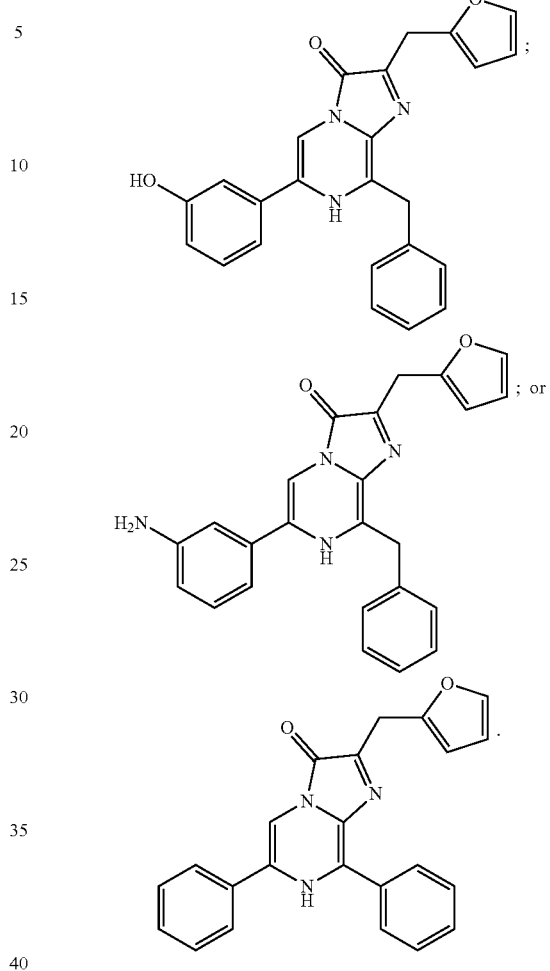

10. The method of claim 1, wherein the live cell is in an animal.

11. The method of claim 1, wherein the coelenterazine-utilizing luciferase is selected from the group of a *Oplophorus* luciferase or variant thereof and a *Renilla* luciferase or a variant thereof.

12. The method of claim 1, wherein the coelenterazine-utilizing luciferase is expressed as a fusion protein.

13. The method of claim 12, wherein the fusion protein comprises the coelenterazine-utilizing luciferase and a protein of interest.

14. The method of claim 13, wherein the coelenterazine-utilizing luciferase is selected from the group of a *Oplophorus* luciferase or variant thereof and a *Renilla* luciferase or a variant therof.

* * * * *